United States Patent
Pierce et al.

(10) Patent No.: US 11,623,953 B2
(45) Date of Patent: Apr. 11, 2023

(54) ANTIBODY CONSTRUCTS AND METHODS OF TREATING CANCER

(71) Applicants: CAERUS THERAPEUTICS, INC., Manassas, VA (US); UNIVERSITY OF GEORGIA RESEARCH FOUNDATION, INC., Athens, GA (US)

(72) Inventors: J. Michael Pierce, Athens, GA (US); Cohava Gelber, Nokesville, VA (US)

(73) Assignees: Caerus Therapeutics, Inc., Manassas, VA (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/489,038

(22) PCT Filed: Feb. 27, 2018

(86) PCT No.: PCT/US2018/020050
§ 371 (c)(1),
(2) Date: Aug. 27, 2019

(87) PCT Pub. No.: WO2018/157169
PCT Pub. Date: Aug. 30, 2018

(65) Prior Publication Data
US 2021/0371516 A1    Dec. 2, 2021

Related U.S. Application Data

(60) Provisional application No. 62/463,868, filed on Feb. 27, 2017.

(51) Int. Cl.
*C07K 16/28* (2006.01)
*C07K 16/30* (2006.01)
*A61K 35/17* (2015.01)
*G01N 33/574* (2006.01)
*A61K 38/00* (2006.01)

(52) U.S. Cl.
CPC .......... *C07K 16/2803* (2013.01); *A61K 35/17* (2013.01); *C07K 16/303* (2013.01); *C07K 16/3046* (2013.01); *G01N 33/57419* (2013.01); *G01N 33/57438* (2013.01); *G01N 33/57473* (2013.01); *A61K 38/00* (2013.01); *C07K 2317/24* (2013.01); *C07K 2317/33* (2013.01); *C07K 2317/565* (2013.01); *G01N 2333/70596* (2013.01)

(58) Field of Classification Search
CPC ............. C07K 16/2803; C07K 16/303; C07K 16/3046; A61K 35/17; A61K 38/00; G01N 33/57419; G01N 33/57438; G01N 33/57473
See application file for complete search history.

(56) References Cited

U.S. PATENT DOCUMENTS

| | | | |
|---|---|---|---|
| 4,518,584 A | 5/1985 | Mark et al. | |
| 4,737,462 A | 4/1988 | Mark et al. | |
| 5,225,539 A | 7/1993 | Winter | |
| 5,530,101 A | 6/1996 | Queen et al. | |
| 5,585,089 A | 12/1996 | Queen et al. | |
| 5,693,761 A | 12/1997 | Queen et al. | |
| 5,693,762 A | 12/1997 | Queen et al. | |
| 7,427,605 B2 | 9/2008 | Davis et al. | |
| 8,329,660 B2 | 12/2012 | Kuchroo et al. | |
| 9,828,423 B2 * | 11/2017 | Chen .................. | A61P 37/02 |
| 2013/0272958 A1 | 10/2013 | Zhang et al. | |

FOREIGN PATENT DOCUMENTS

| CN | 101607985 A | 12/2009 |
|---|---|---|
| WO | WO 1990/07861 | 7/1990 |
| WO | WO 1992/22653 | 12/1992 |
| WO | WO 2003/063792 | 8/2003 |
| WO | WO 2012/040824 | 4/2012 |
| WO | WO 2015/184207 | 12/2015 |
| WO | 2016-150899 | 9/2016 |

OTHER PUBLICATIONS

Malia et al, Proteins, 2016, 84:427-434. (Year: 2016).*
Barthelemy et al, Journal of Biological Chemistry, 2008, 283:3639-3654. (Year: 2008).*
Beiboer et al, Journal of Molecular Biology, 2000, 296:833-849. (Year: 2000).*
Choi et al, 2011, Molecular Biosystems, 2011, 7:3327-3334. (Year: 2011).*
De Genst et al, Developmental and Comparative Immunology, 2006, 30:187-98. (Year: 2006).*
Griffiths et al, The EMBO Journal, 1993, 12:725-734. (Year: 1993).*
Klimka et al, British Journal of Cancer, 2000, 83:252-260. (Year: 2000).*
Ward et al, Nature, 1989, 341:544-546. (Year: 1989).*
Lee, O.J. et al., "CEACAM6 as detected by AP11 antibody is a marker notable for mucin-producing adenocarcinomas" Virchows Arch, 2015, vol. 466, pp. 151-159.
Hong, K.P. et al., "Therapeutic effect of anti CEACAM6 monoclonal antibody against lung adenocarcinoma by enhancing anoikis sensitivity" Biomaterials, 2015, vol. 67, pp. 32-41.
NCBI, Genbank accession No. EAW5706.1 (Mar. 23, 2015).
International Search Report and Written Opinion dated Jun. 7, 2018 for corresponding PCT/US2018/020050.

(Continued)

*Primary Examiner* — Julie Wu
*Assistant Examiner* — Cheom-Gil Cheong
(74) *Attorney, Agent, or Firm* — Mark. S. Cohen; Pearl Cohen Zedek Latzer Baratz LLP

(57) ABSTRACT

Provided herein are antibodies and related polypeptides that bind specifically to CEACAM6. The antibodies and/or polypeptides can be configured as bispecific T cell engagers. The antibodies and/or polypeptides can also be configured as chimeric antigen receptors. Also provided are methods of detection and treatment of cancer, for example, pancreatic cancer, using the antibodies and related polypeptides herein.

20 Claims, 58 Drawing Sheets

Specification includes a Sequence Listing.

(56) References Cited

OTHER PUBLICATIONS

Suzuki et al, "Heterogeneity of Circulating Carcinoembryonic Antigen Analyzed by Sandwich-Enzyme Immunoassays with Different Specificities," *Cancer Research* 1987, vol. 47, No. 18, pp. 4782-4787.
Leung, K. K. et al., "Broad and thematic remodeling of the surfaceome and glycoproteome on isogenic cells transformed with driving proliferative oncogenes", *PNAS* 2020, 117(14): 7764-7775.
Jiang, H. & Rugo, H. S., "Human epidermal growth factor receptor 2 positive (HER2+) metastatic breast cancer: how the latest results are improving therapeutic options", *Ther Adv Med Oncol* 2015, 7(6): 321-339.
Sterner, E. et al., "Perspectives on Anti-Glycan Antibodies Gleaned from Development of a Community Resource Database", *ACS Chem. Biol.* 2016, 11, 1773-1783.
Strickland, L. A. et al., "Preclinical evaluation of carcinoembryonic cell adhesion molecule (CEACAM) 6 as potential therapy target for pancreatic adenocarcinoma", *J Pathol* 2009; 218: 380-390.
Dolezal, S.J., "A unique glycan is a specific marker for pancreatic adenocarcinoma, University of Georgia Theses and Dissertations," 2015, 1-129.
Holderness, Jeff, et al., *Cancer Research*, "Novel monoclonal antibody targeting cancel stem cells," 2015, vol. 75, No. 15 Suppl 1, Abstract 2485.
Dolezal, Sam et al., *Glycoconjugate Journal*, "An unusual, protein-specific N-glycan with high sensitivity and specificity for pancreatic adenocarcinoma," 2015, vol. 32, No. 5, p. 316, Abstract 321.
European Search Report from EP 18758526 dated Sep. 10, 2020.
Chien et al. "Novel cationic cardiolipin analogue-based liposome for efficient DNA and small interfering RNA delivery in vitro and in vivo." Cancer gene therapy 12.3 (2005): 321-328.
Chothia, Cyrus, and Arthur M. Lesk. "Canonical structures for the hypervariable regions of immunoglobulins." *Journal of molecular biology* 196.4 (1987): 901-917.
Chothia, Cyrus, et al. "Conformations of immunoglobulin hypervariable regions." *Nature* 342.6252 (1989): 877-883.
Durcy et al., "Antibody-drug conjugates: linking cytotoxic payloads to monoclonal antibodies." Bioconjugate chemistry 21.1 (2010): 5-13.
Fessart et al., "Three-dimensional culture model to distinguish normal from malignant human bronchial epithelial cells." *European Respiratory Journal* 42.5 (2013): 1345-1356.
Gorman, Cornelia M., et al. "The Rous sarcoma virus long terminal repeat is a strong promoter when introduced into a variety of eukaryotic cells by DNA-mediated transfection." *Proceedings of the National Academy of Sciences* 79.22 (1982): 6777-6781.
Hamer, Philip C. De, Witt, et al. "Quantification of viability in organotypic multicellular spheroids of human malignant glioma using lactate dehydrogenase activity: a rapid and reliable automated assay." *Journal of Histochemistry & Cytochemistry* 53.1 (2005): 23-34.
Huston, et al. "Protein engineering of antibody binding sites: recovery of specific activity in an anti-digoxin single-chain Fv analogue produced in *Escherichia coli*." *Proceedings of the National Academy of Sciences* 85.16 (1988): 5879-5883.
Kipriyanov, Sergey M., et al. "Recombinant single-chain Fv fragments carrying C-terminal cysteine residues: production of bivalent and biotinylated miniantibodies." Molecular immunology 31.14 (1994): 1047-1058.
Kipriyanov, Sergey M., et al. "Single-chain antibody streptavidin fusions: tetrameric bifunctional scFv-complexes with biotin binding activity and enhanced affinity to antigen." *Human Antibodies* 6.3 (1995): 93-101.
Li, Zhong. "CD133: a stem cell biomarker and beyond." *Experimental hematology & oncology* 2.1 (2013): 1-8.
Maher et al., "CAR mechanics: driving T cells into the MUC of cancer." Cancer research 69.11 (2009): 4559-4562.
Oberst, Michael D., Stacy Fuhrmann, Kathy Mulgrew, Maria Amann, Lily Cheng, Petra Lutterbuese, Laura Richman, Steve Coats, Patrick A. Baeuerle, and Scott A. Hammond. "CEA/CD3 bispecific antibody MEDI-565/AMG 211 activation of T cells and subsequent killing of human tumors is independent of mutations commonly found in colorectal adenocarcinomas." In MAbs, vol. 6, No. 6, pp. 1571-1584. Taylor & Francis, 2014.
Poljak, Roberto J. "Production and structure of diabodies." *Structure* 2.12 (1994): 1121-1123.
Queen, Cary, et al. "A humanized antibody that binds to the interleukin 2 receptor." *Proceedings of the National Academy of Sciences* 86.24 (1989): 10029-10033.
Reardon et al., "Immunotherapy advances for glioblastoma." Neuro-oncology 16.11 (2014): 1441-1458.
Sorensen et al., "Gene silencing by systemic delivery of synthetic siRNAs in adult mice." Journal of molecular biology 327.4 (2003): 761-766.
Soutschek, Jürgen, et al. "Therapeutic silencing of an endogenous gene by systemic administration of modified siRNAs." *Nature* 432.7014 (2004): 173-178.
Tamada, et al. "Redirecting gene-modified T cells toward various cancer types using tagged antibodies." Clinical Cancer Research 18.23 (2012): 6436-6445.
Tomalia et al., "Dendrimers as multi-purpose nanodevices for oncology drug delivery and diagnostic imaging." (2007): 61-67.
Zimmerman et al., "Unleashing the clinical power of T cells: CD19/CD3 bi-specific T cell engager (BiTE®) antibody construct blinatumomab as a potential therapy." International immunology 27.1 (2014): 31-37.
Zimmerman et al. "RNAi-mediated gene silencing in non-human primates." Nature 441.7089 (2006): 111-114.

\* cited by examiner

Fig. 4

PTA-2357 Variable Heavy Chain Nucleotide (SEQ ID NO: 29) and Amino Acid (SEQ ID NO: 13) Sequences VH Variant 1

```
          10         20         30         40         50         60         70         80         90        100
CAGGTCCAGCTGGTGCAGTCTGGGCCTGAGCTGAAGAAGCCTGGGGCCTCAGTGAAGGTGTCCTGCAAGGTTCCGGCTACCCATTCACTGATTATACTA
 Q  V  Q  L  V  Q  S  G  P  E  L  K  K  P  G  A  S  V  K  V  S  C  K  V  P  A  T  H  S  L  I  I  Y
                            10                          20                          30

110        120        130        140        150        160        170        180        190        200
TACACTGGGTGAGGCAGGCCCAGGGACAAATCCACCAGCACAGCCTATATGGAACTTAGGAGCTTGAGGTCTGACGATTCTACCGTGTATTACTGTGCAAGAGGGGAT
  T  L  G  E  A  G  P  G  T  N  P  P  A  Q  P  I  W  N  L  G  A  *  G  L  T  I  L  P  C  I  T  V  Q  E  G  M
           40                          50                          60                          70

210        220        230        240        250        260        270        280        290        300
GGCCACAATGACTGTAGACAAATCCACCAGCACAGCCTATATGGAACTTAGGAGCTTGAGGTCTGACGATTCTACCGTGTATTACTGTGCAAGAGGGGAT
 A  T  M  T  V  D  K  S  T  S  T  A  Y  M  E  L  R  S  L  R  S  D  D  S  T  V  Y  Y  C  A  R  G  D
              70                          80  82                       90
                                               A B C
```

Fig. 4 (cont.)

```
        310        320        330        340        350        360
TACTACGGTAGTTACTACAAATGGAATTTGAATACTGGGGCCAAGGCACCACTGTGACAGTCTCCTCA
 Y  Y  G  S  Y  Y  K  W  N  L  N  Y  W  G  Q  G  T  T  V  T  V  S  S
    100 A  B  C  D                                     110
```

CDR definitions and protein sequence numbering according to Kabat. CDR nucleotide and protein sequences are highlighted in red. Variant 1 amino acids changed from the original hybridoma sequence are highlighted in green.

Fig. 5

PTA-2357 Variable Heavy Chain Nucleotide (SEQ ID NO: 30) and Amino Acid (SEQ ID NO: 14) Sequences VH Variant 2

```
           10        20        30        40        50        60        70        80        90       100
CAGGTCCAGCTGGTGCAGTCTGGGGCCGAGGTGAAGAAGCCTGGGGCCTCAGTGAAGGTGTCCTGCAAGGTTCCGGCTACCCATTCACTGATTATACTA
Q  V  Q  L  V  Q  S  G  A  E  V  K  K  P  G  A  S  V  K  V  S  C  K  G  S  G  Y  P  F  T  D  Y  T
                          10                        20                        30

110       120       130       140       150       160       170       180       190       200
TACACTGGGTGAGGCAGGCCCATGGCCAGGGGCCTAGAGTGGATTGGACATATTAGTACCTACTCTGGTAACACCAACTACAACCAGAAGTTTAAGGGCAG
I  H  W  V  R  Q  A  H  G  Q  G  L  E  W  I  G  H  I  S  T  Y  S  G  N  T  N  Y  N  Q  K  F  K  G  R
                40                        50  52 A                        60
                                              A B C 210       220       230       240       250       260       270       280       290       300
GGCCACAATGACTGTAGACAAATCCACCAGCACAGCCTATATGGAACTTAGGAGCTTGACGAGTCTGACGATTCTACCGTGTATTACTGTGCAAGAGATTCAG
A  T  M  T  V  D  K  S  T  S  T  A  Y  M  E  L  R  S  L  R  S  D  D  S  T  V  Y  Y  C  A  R  D
   70                        80  82 A                        90
                                  A B C
```

Fig. 5 (cont.)

```
        310       320       330       340       350       360
TACTACGGTAGTAGCTACTTCTACTACAAATTTGAAATACTGGGGCCAAGGCACCACTGTGACAGTCTCCTCA

Y  Y  G  S  S  Y  F  Y  Y  K  F  E  Y  W  G  Q  G  T  T  V  T  V  S  S
       100  A  B  C  D                                    110
```

CDR definitions and protein sequence numbering according to Kabat. CDR nucleotide and protein sequences are highlighted in red. Variant 2 amino acids changed from the original hybridoma sequence are highlighted in green.

Fig. 6

PTA-2357 Variable Heavy Chain Nucleotide (SEQ ID NO: 31) and Amino Acid (SEQ ID NO: 15) Sequences VH Variant 3

```
         10         20         30         40         50         60         70         80         90        100
CAGGTCCAGCTGGTGCAGTCTGGGGCCGAGGTGAAGAAGCCTGGGGCCTCAGTGAAGGTGTCCTGCAAGGGTTCCGGCTACCCATTCACTGATTATACAA

Q  V  Q  L  V  Q  S  G  A  E  V  K  K  P  G  A  S  V  K  V  S  C  K  G  S  G  Y  P  F  T  D  Y  T
                                10                          20                          30

110        120        130        140        150        160        170        180        190        200
TACACTGGGTGAGGCAGGCCCCTGGCCAAGGGCTAGAGTGGATTGGACATATTAGTTACTCTGGTAACACTAACTACAACCAGAAGTTTAAGGGCCAG

I  H  W  V  R  Q  A  P  G  Q  G  L  E  W  I  G  H  I  S  Y  S  G  N  T  N  Y  N  Q  K  F  K  G  Q
                          40                          50 52                         60
                                                          A 210        220        230        240        250        260        270        280        290        300
GGCCACAATGACTGTAGACAAATCCACCAGCACAGCCTATATGGAACTTAGGAGCTTGAGGTCTGACGATACCACCGTGTATTACTGTGCAAGAGGGGAT

```
       310       320       330       340       350       360
TACTACGGTAGTAGCTACTACAAATTTGAAATACTGGGGCCAAGGCACCACTGTGACAGTCTCCTCA
 Y  Y  G  S  S  Y  Y  K  F  E  Y  W  G  Q  G  T  T  V  T  V  S  S
           100  A  B  C  D                          110
```

CDR definitions and protein sequence numbering according to Kabat. CDR nucleotide and protein sequences are highlighted in green. Variant 3 amino acids changed from the original hybridoma sequence are highlighted in red.

Fig. 7

PTA-2357 Variable Heavy Chain Nucleotide (SEQ ID NO: 32) and Amino Acid (SEQ ID NO: 16) Sequences VH Variant 4

```
          10         20         30         40         50         60         70         80         90        100
CAGGTTCCAGTCTGGTGGTGCAGTCTGGGGCCGAGGTGAAGAAGCCTGGGGCCTCAGTGAAGGTGTCCTGCAAGGTTCCGGCTACCCATTCACTGA????AC??A

Q  V  Q  L  V  Q  S  G  A  E  V  K  K  P  G  A  S  V  K  V  S  C  K  G  S  G  Y  P  F  T  ?  ?  ?
                            10                         20                                30

110        120        130        140        150        160        170        180        190        200
???C?CTGGGTGAGGCAGGCCCCTGGCCAGGGGCCTAGAGTGGATTGGACA?A??A.?????A.C?????C??G?TA?C?C?G???A.CACCAACAACAA.C???CA?G?AAG?T?A?GG??CAG

I  ?  W  V  R  Q  A  P  G  Q  ?  L  E  W  I  G  ?  I  ?  ?  Y  ?  G  ?  T  ?  ?  Q  K  F  K  ?  R
                       40                              50                           60
                                                       52 A 210        220        230        240        250        260        270        280        290        300
GGCCACAATGACTGTAGACAAATCCACCAGCACAGCCTATATGGAACTTAGGAGCTTGAGGTCTGACGATACCGCCGTGTATTACTGTGCAAGAG??????A?

```
       310        320        330        340        350        360
TACTACGGTAGTTCTACAAATTGAATTACTGGGGCCAAGGCACCACTGTGACAGTCTCCTCA
 Y  Y  G  S  F  Y  K  F  E  Y  W  G  Q  G  T  T  V  T  V  S  S
    100  A  B  C  D                           110
```

CDR definitions and protein sequence numbering according to Kabat. CDR nucleotide and protein sequences are highlighted in red. Variant 4 amino acids changed from the original hybridoma sequence are highlighted in green.

Fig. 8

PTA-2357 Variable Heavy Chain Nucleotide (SEQ ID NO: 33) and Amino Acid (SEQ ID NO: 17) Sequences VH Variant 5

```
         10        20        30        40        50        60        70        80        90        100
CAGGTCCAGCTGGTGCAGTCTGGGGCCGAGGTGAAGAAGCCTGGGGCCTCAGTGAAGGTGTCCTGCAAGGGTTCCGGCTACCCATTCACTGATTATACTAT
 Q  V  Q  L  V  Q  S  G  A  E  V  K  K  P  G  A  S  V  K  V  S  C  K  G  S  G  Y  P  F  T  D  Y  T  M
                                    10                      20                      30

110       120       130       140       150       160       170       180       190       200
TCACTGGGTGAGGCAGGCCCCTGGCCAAGGGCCTAGAGTGGATTGGACATATTAATCCTACTAGTGGTAACACTAACTACAACCAGAAGTTTAAGGGCCAG
 I  H  W  V  R  Q  A  P  G  Q  G  L  E  W  I  G  H  I  N  P  T  S  G  N  T  N  Y  N  Q  K  F  K  G  R
                 40                      50                      60
                                         52
                                          A 210       220       230       240       250       260       270       280       290       300
GGTGACAATGACTGTAGACAAATCCACCAGCACAGCCTATATGGAACTTAGGAGCTTGAGGTCTGACGATACCGCCGTGTATTACTGTGCAAGAGATGGAT
 V  T  M  T  V  D  K  S  T  S  T  A  Y  M  E  L  R  S  L  R  S  D  D  T  A  V  Y  Y  C  A  R  D  G
         70                      80                      90
                                  82
                                   A  B  C
```

Fig. 8 (cont.)

```
       310       320       330       340       350       360
TACTACGGTAGTAGTTACTACAAATTTGAATACTGGGGCCAAGGCACCACTGTGACAGTCTCCTCA
 Y  Y  G  S  S  Y  Y  K  F  E  Y  W  G  Q  G  T  T  V  T  V  S  S
       100 A  B  C  D                                110
```

CDR definitions and protein sequence numbering according to Kabat. CDR nucleotide and protein sequences are highlighted in red. Variant 5 amino acids changed from the original hybridoma sequence are highlighted in green.

Fig. 9

PTA-2357 Variable Light Chain Nucleotide (SEQ ID NO: 34) and Amino Acid
(SEQ ID NO: 18) Sequences VK Variant 1

```
         10        20        30        40        50        60        70        80        90       100
GACATCAAGATGACTCAGTCTCCAAGCTCACTGTCTGCATCTGTGGGAGACAGGGTCACCATCACATGTGGTGCAAGTGAAAATATTTACAGTGCTTTAA
 D  I  K  M  T  Q  S  P  S  S  L  S  A  S  V  G  D  R  V  T  I  T  C  G  A  S  E  N  I  Y  G  A  L
                                  10                        20                        30

110       120       130       140       150       160       170       180       190       200
AATGGTTCCAGCGGAAACAGGGAAAAGGGAAACCCCCTAAGCTCCTGATCTATGGTGCAACTTGGCTAGCAGATGGCATGCCTTCGAGGTTCAGTGGCAGTGGATC
 N  W  F  Q  R  K  Q  G  K  G  K  P  P  K  L  L  I  Y  G  A  T  W  L  A  D  G  M  P  S  R  F  S  G  S  G  S
                   40                        50                        60

210       220       230       240       250       260       270       280       290       300
TGGTAGAGACTTCACCCTCACCATCAGCAGCCTGCAGCCTGAGGATTTCGCAACGTATTTCTGTCAAAATGTGTTAAGTATCCCTTACACTTTTGGCCAG
 G  R  D  F  T  L  T  I  S  S  L  Q  P  E  D  F  A  T  Y  F  C  Q  N  V  L  S  I  P  Y  T  F  G  Q
          70                        80                        90                       100
```

Fig. 9 (cont.)

```
          310        320
GGGACCCAGCTGGAGATCAAA G        T
    Q   L   E   I   K
                   106 A
```

CDR definitions and protein sequence numbering according to Kabat. CDR nucleotide and protein sequences are highlighted in red. Variant 1 amino acids changed from the original hybridoma sequence are highlighted in green.

Fig. 10

*PTA-2357 Variable Light Chain Nucleotide(SEQ ID NO: 35) and Amino Acid (SEQ ID NO: 19) Sequences VK Variant 2*

```
         10        20        30        40        50        60        70        80        90       100
GACATCAAGATGACTCAGTCTCCAAGCTCACTGTCTGCATCTGTGGGAGACAGGGTCACCATCACATGTGCAAGTGAAGATATATACAATGCCTTTAA
 D  I  K  M  T  Q  S  P  S  S  L  S  A  S  V  G  D  R  V  T  I  T  C  G  A  S  E  W  I  Y  G  A  L
                                            10                      20                      30

110       120       130       140       150       160       170       180       190       200
ATGGTTCCAGCGGAAACCTGGAAAAGCCCCTAAGCTCCTGATCTATGGTGCAACTTGGCTAGCAGATGGCATGCCTTCGAGGTTCAGTGGCAGTGGATC
 W  F  Q  R  K  P  G  K  A  P  K  L  L  I  Y  G  A  T  W  L  A  D  G  M  P  S  R  F  S  G  S  G  S
                40                      50                      60

210       220       230       240       250       260       270       280       290       300
TGGTAGAGACTTCACCCTCACCATCAGCAGCCTGCAGCCTGAGGATTTCGCAACGTATTTCTGTCAAAATGTTTAAGTATCCTTATACATTTTGGCCAG
 G  R  D  F  T  L  T  I  S  S  L  Q  P  E  D  F  A  T  Y  F  C  Q  N  V  L  S  I  P  Y  T  F  G  Q
        70                      80                      90                     100
```

Fig. 10 (cont.)

```
        310       320
GGGACCAAGCTGGAGATCAAA
  G   T   K   L   E   I   K
                    106 A
```

CDR definitions and protein sequence numbering according to Kabat. CDR nucleotide and protein sequences are highlighted in red. Variant 2 amino acids changed from the original hybridoma sequence are highlighted in green.

Fig. 11

*PTA-2357 Variable Light Chain Nucleotide (SEQ ID NO: 36) and Amino Acid (SEQ ID NO: 20) Sequences VK Variant 3*

```
         10        20        30        40        50        60        70        80        90       100
GACATCCAGATGACTCAGTCTCCAAGCTCTCTGTCTGCATCTGTGGGAGACAGGGTCACCATCACATGTGGAGCAAGTGAGAATATTTACAGTGCTTTAA
 D  I  Q  M  T  Q  S  P  S  S  L  S  A  S  V  G  D  R  V  T  I  T  C  G  A  S  E  N  I  Y  G  A  L
                                              10                      20                      30
```

```
        110       120       130       140       150       160       170       180       190       200
ATTGGTTCCAGCGGAAACCTGGAAAAGCCCCTAAGCTCCTGATCTATGGTGCAACTTGGTTAGCAGATGGCATGCCTTCGAGGTTCAGTGGCAGTGGATC
  W  F  Q  R  K  P  G  K  A  P  K  L  L  I  Y  G  A  T  W  L  A  D  G  M  P  S  R  F  S  G  S  G  S
                    40                      50                      60
```

```
        210       220       230       240       250       260       270       280       290       300
TGGTAGAGACTTCACCCTCACCATCAGCAGCCTGCAGCCTGAGGATTTCGCAACGTATTTCTGTCAAAATGTGTTAAGTATACCTTATACACTTTTGGCCAG
  G  R  D  F  T  L  T  I  S  S  L  Q  P  E  D  F  A  T  Y  F  C  Q  N  V  L  S  I  P  Y  T  L  L  A
                    70                      80                      90                     100
```

Fig. 11 (cont.)

```
        310       320
GGGACCAAGCTGGAGATCAAA
 G  T  K  L  E  I  K
              106 A
```

CDR definitions and protein sequence numbering according to Kabat. CDR nucleotide and protein sequences are highlighted in red. Variant 3 amino acids changed from the original hybridoma sequence are highlighted in green.

Fig. 12

PTA-2358 Variable Heavy Chain Nucleotide (SEQ ID NO: 37) and Amino Acid (SEQ ID NO: 21) Sequences VH Variant 1

```
         10        20        30        40        50        60        70        80        90       100
GAGGTTCAGCTGGTGCAGTCTGGGGCAGAGCTTAAGAAGCCTGGGGCCTCAGTCAAGTTGTCCTGCACAGCTTCTGGCTTCAACATTAAAGACTACTATA
  E  V  Q  L  V  Q  S  G  A  E  L  K  K  P  G  A  S  V  K  L  S  C  T  A  S  G  F  N  I  K  D  Y  Y
                             10                        20                        30

110       120       130       140       150       160       170       180       190       200
TGCACTGGGTGAAGCAGGCCCCTGGCCAGGGCCTGGAGTGGATTGGATGGATTGATCCTGAAAATGGTGATACTGAATATGCCCCTAAGTTCCAGGGCAG
  M  H  W  V  K  Q  A  P  G  Q  G  L  E  W  I  G  W  I  D  P  G  N  G  D  T  E  A  P  K  F  Q  G  R
                 40                        50  52                        60
                                                  A 210       220       230       240       250       260       270       280       290       300
GGCCACTTTGACTGCAGACACATCCATCAACACAGCCTACCTGGAGCTCAGCAGCCTGAGGTCTGAGGACACTGCCGTCTATTACTGTAATGCTCCTTAC
  A  T  L  T  A  D  T  S  I  N  T  A  Y  L  E  L  S  S  L  K  S  E  D  T  A  V  Y  Y  C  N  A  P  Y
              70                        80 82                                      90
                                              A B C
```

Fig. 12 (cont.)

```
        310       320       330       340       350       360
TACTGCGGTAGTAGTAACTTTGACTACTGGGGCCAAGGCACCACTGTGACAGTCTCCTCA
  Y  C  G  S  S  N  F  D  Y  W  G  Q  G  T  T  V  T  V  S  S
       100 A  B  C                            110
```

CDR definitions and protein sequence numbering according to Kabat. CDR nucleotide and protein sequences are highlighted in red. Variant 1 amino acids changed from the original hybridoma sequence are highlighted in green.

Fig. 13

PTA-2358 Variable Heavy Chain Nucleotide (SEQ ID NO: 38) and Amino Acid (SEQ ID NO: 22) Sequences VH Variant 2

```
          10         20         30         40         50         60         70         80         90        100
GAGGTTCAGTTGGTGCAGTCTGGGGCAGAGGTGAAGAAGCCTGGGGCCTCAGTCAAGTTGTCCTGCACAGCTTCTGGCTTCAACATTAAAGACTACTAAA
 E  V  Q  L  V  Q  S  G  A  E  V  K  K  P  G  A  S  V  K  L  S  C  T  A  S  G  F  N  I  K  D  Y  Y
                                 10                      20                      30

110        120        130        140        150        160        170        180        190        200
ATGCACTGGGTGAAGCAGGCCCCTGGCCAGGGCCTGGAGTGGATTGGATGGATTGATCCTGAAAATGGTGATACTGAATATGCCCCGAAGTTCCAGGGCAG
 M  H  W  V  K  Q  A  P  G  Q  G  L  E  W  I  G  W  I  D  P  G  W  G  D  T  E  C  A  P  K  F  Q  G  R
                  40                      50  52 A                              60
                                              A  B  C 210        220        230        240        250        260        270        280        290        300
GGCCACTTTGACTGCAGACACATCCATCAACACAGCCTACCTGGAGCTCAGCAGGCTGAGGTCTGACGACACTGCCGTCTATTACTGTAATGCTCCTTAT
 A  T  L  T  A  D  T  S  I  N  T  A  Y  L  E  L  S  R  L  R  S  D  D  T  A  V  Y  Y  C  N  A  P  Y
 70                      80  82 A                          90
                             A  B  C
```

Fig. 13 (cont.)

```
         310        320        330        340        350        360
TACTCCGGTAGTAGTTACTACTTTGACTACTGGGGCCAAGGCACCACTGTGACAGTCTCCTCA
 Y  S  G  S  S  Y  Y  F  D  Y  W  G  Q  G  T  T  V  T  V  S  S
       100 A  B  C                                110
```

CDR definitions and protein sequence numbering according to Kabat. CDR nucleotide and protein sequences are highlighted in red. Variant 2 amino acids changed from the original hybridoma sequence are highlighted in green.

Fig. 14

PTA-2358 Variable Heavy Chain Nucleotide (SEQ ID NO: 39) and Amino Acid (SEQ ID NO: 23) Sequences VH Variant 3

```
          10        20        30        40        50        60        70        80        90       100
GAGGTTCAGCTGGTGCAGTCTGGGGGAGAGGTGAAGAAGCCTGGGGCCTCAGTCAAGTTGTCCTGCACAGCTTCTGGCTTCAACATTAAAGACTACTATA
 E  V  Q  L  V  Q  S  G  A  E  V  K  K  P  G  A  S  V  K  L  S  C  T  A  S  G  F  N  I  K  D  Y  Y
                           10                        20                        30

110       120       130       140       150       160       170       180       190       200
ATGCACTGGGTGAGGCAGGCCCCTGGCCAGGGCCTGGAGTGGATTGGATGGATTGATCCTGAAAATGGTGATACTGAATATGCTCCGAAGTTCCAGGGCAG
 M  H  W  V  R  Q  A  P  G  Q  G  L  E  W  I  G  W  I  D  P  E  N  G  D  T  E  Y  A  P  K  F  Q  G
                 40                        50                        60
                                           52 A 210       220       230       240       250       260       270       280       290       300
GGCCACTTTGACTGCAGACACATCCATCAACACAGCCTACCTGGAGCTCAGCAGTCTGAGGTCTGACGACACTGCCGTCTATTACTGTAATGCTCCCTAT
 A  T  L  T  A  D  T  S  I  N  T  A  Y  L  E  L  S  S  L  R  S  D  D  T  A  V  Y  Y  C  N  A  P  Y
    70                        80                        82 A  B  C         90
```

Fig. 14 (cont.)

```
          310       320       330       340       350       360
TACTGCGGGTAGTAGCCACTTTGACTACTGGGGCCAAGGCACCACTGTGACAGTCTCCTCA
 Y  C  G  S  S  H  F  D  Y  W  G  Q  G  T  T  V  T  V  S  S
    100  A  B  C                                   110
```

CDR definitions and protein sequence numbering according to Kabat. CDR nucleotide and protein sequences are highlighted in red. Variant 3 amino acids changed from the original hybridoma sequence are highlighted in green.

Fig. 15

PTA-2358 Variable Heavy Chain Nucleotide (SEQ ID NO: 30) and Amino Acid (SEQ ID NO: 24) Sequences VH Variant 4

```
         10        20        30        40        50        60        70        80        90       100
GAGGTTCAGTTGGTGGAGTCTGGGGGAGAGGTGAAGAAGCCTGGGGCCTCAGTCAAGTTGTCCTGCACAGCTTCTGGCTTCAACATTAAAGACTACTAAA
 E  V  Q  L  V  Q  S  G  A  E  V  K  K  P  G  A  S  V  K  L  S  C  T  A  S  G  F  N  I  K  D  Y  Y
                            10                        20                        30

110       120       130       140       150       160       170       180       190       200
ATGCACTGGGTGAGGCAGGCCCCTGGCCAGGGCCTGGAGTGGATTGGATGGATTGATCCTGAAAATGGTGATACTGAATACGCCCCGAAGTTCCAGGGCAG
 M  H  W  V  R  Q  A  P  G  Q  G  L  E  W  I  G  W  I  D  P  E  N  G  D  T  E  Y  A  P  K  F  Q  G  R
                   40                        50  52 A                        60

210       220       230       240       250       260       270       280       290       300
GGCCACTTTGACTGCAGACACATCCATCAGCACAGCCTACCTGGAGCTCAGCAGCCTGAGACGCTGACGACACTGCCGTCTATTACTGTAATGCTCTTTAT
 A  T  L  T  A  D  T  S  I  S  T  A  Y  L  E  L  S  R  L  R  S  D  D  T  A  V  Y  Y  C  N  A  F  Y
          70                        80  82 A B C                        90
```

Fig. 15 (cont.)

```
        310       320       330       340       350       360
TACTCCGGTAGTAGTAGTAGTTACGACTTTGACTACTGGGGCCAAGGCACCACTGTGACAGTCTCCTCA
 Y  S  G  S  S  S  S  Y  D  F  D  Y  W  G  Q  G  T  T  V  T  V  S  S
        100 A  B  C                                110
```

CDR definitions and protein sequence numbering according to Kabat. CDR nucleotide and protein sequences are highlighted in red. Variant 4 amino acids changed from the original hybridoma sequence are highlighted in green.

Fig. 16

PTA-2358 Variable Heavy Chain Nucleotide (SEQ ID NO: 41) and Amino Acid (SEQ ID NO: 25) Sequences VH Variant 5

```
         10         20         30         40         50         60         70         80         90        100
GAGGTTCAGCTGGTGGTGCAGTCTGGGGCAGAGGTTGAAGAAGCCTGGGGCCTCAGTGAAGGTGTCCTGCACAGCTTCTGGCTTCAACATTAAAXACXACTATA
 E  V  Q  L  V  Q  S  G  A  E  V  K  K  P  G  A  S  V  K  V  S  C  T  A  S  G  F  N  I  K  D  Y  Y
                                 10                        20                        30

110        120        130        140        150        160        170        180        190        200
XXXACTGGGTGAGGCAGGCCCCTGGACAGGGCCTGGAGTGGATTGGATGGAXXXXXXXXXXXAXXXXXATGXXGAAXACTGAATGCXXXCCCXAAGTTCCAGGGCAG
 M  X  W  V  R  Q  A  P  G  Q  G  L  E  W  I  G  W  I  D  P  X  Q  G  D  T  E  C  A  P  K  F  Q  G  X
                40                        50 52                        60
                                              A 210        220        230        240        250        260        270        280        290        300
GGCCACTATCACTGCAGACACATCCATCAGCACAGCCTACATGGAGCTCAGCAGGCTGAGGTCTGACGACACTGCCGTCTATTACTGTAATGCTCCXXAT
 A  X  T  A  D  T  S  I  S  T  A  Y  M  E  L  S  R  L  R  S  D  D  T  A  V  Y  Y  C  N  A  P  Y
    70                        80 82                             90
                                 A  B  C
```

Fig. 16 (cont.)

```
       310       320       330       340       350       360
TACTCCGGTAGTAGCCACTTTGACTACTGGGGCCAAGGCACCACTGTGACAGTCTCCTCA
 Y  S  G  S  S  H  F  D  Y  W  G  Q  G  T  T  V  T  V  S  S
        100  A  B  C                                110
```

CDR definitions and protein sequence numbering according to Kabat. CDR nucleotide and protein sequences are highlighted in green. Variant 5 amino acids changed from the original hybridoma sequence are highlighted in red.

Fig. 17

PTA-2358 Variable Light Chain Nucleotide (SEQ ID NO: 42) and Amino Acid
(SEQ ID NO: 26) Sequences VK Variant 1

```
         10        20        30        40        50        60        70        80        90       100
GACATTGTGCTGACACAGTCTCCTGACTCTCTTAGCTGTATCTCTGGGGAGAGGGCCACCATCAACTGCAGGGCCAGCAAAAGTGTCAGTGCACACTGGCT
 D  I  V  L  T  Q  S  P  D  S  L  A  V  S  L  G  E  R  A  T  I  N  C  R  A  S  K  S  V  S  A  S  G
                              10                       20                       27 A  B  C  D 110       120       130       140       150       160       170       180       190       200
AAACTATTTGGCACTGGTACCAACAGAAACCAGGACAGCCACCCAAACTCCTCATCTATCTTGCATCCAACTGGAATCTGGGGTCCCTGACAGGTTCAG
  N  Y  L  H  W  Y  Q  Q  K  P  G  Q  P  P  K  L  L  I  Y  L  A  S  N  L  E  S  G  V  P  D  R  F  S
 30                       40                                  50                       60

210       220       230       240       250       260       270       280       290       300
TGGCAGTGGGTCTGGGACAGACTTCACCCTCACCATCAGCAGCCTGCAGGAGGAGGATGTGGCAACCTATTACTGTCAGCAGAGTAGAGAGCTTCGGACG
  G  S  G  S  G  T  D  F  T  L  T  I  S  S  L  Q  E  E  D  V  A  T  Y  Y  C  Q  Q  S  R  E  L  R  T
                 70                            80                            90             94  96
```

Fig. 17 (cont.)

```
          310       320       330
TTCGGTCAGGGCACCAAGCTGGAAATCAAA

F  G  Q  G  T  K  L  E  I  K
   100                    106  A
```

CDR definitions and protein sequence numbering according to Kabat. CDR nucleotide and protein sequences are highlighted in red. Variant 1 amino acids changed from the original hybridoma sequence are highlighted in green.

Fig. 18

*PTA-2358 Variable Light Chain Nucleotide(SEQ ID NO: 43) and Amino Acid (SEQ ID NO: 27)Sequences VK Variant 2*

```
         10         20         30         40         50         60         70         80         90        100
GACATTGTGCTGACACAGTCTCCTGACTCTCTTAGCTGTGTATCTCTGGGGAGAGGGCCACCATCAACTGCAGGGCCAGTGAAAGTGTTCAGTGACAATGGCT
 D  I  V  L  T  Q  S  P  D  S  L  A  V  S  L  G  E  R  A  T  I  N  C  R  A  S  K  S  V  S  A  S  G
                               10                          20                         27 A  B  C  D 110        120        130        140        150        160        170        180        190        200
ATAGTTTTATGCACTGGTACCAACAGAAACCAGGACAGCCACCCAAACTCCTCATCTATCTTGCATCCAACCTGGAATCTGGGGTCCCTGACAGGTTCAG
 Y  S  F  M  H  W  Y  Q  Q  K  P  G  Q  P  P  K  L  L  I  Y  L  A  S  N  L  E  S  G  V  P  D  R  F  S
 30                        40                         50                          60

210        220        230        240        250        260        270        280        290        300
TGGCAGTGGGTCTGGGACAGACTTCACCCTCACCATCAGCAGCCTGCAGGCCGAGGATGTGGCAACCTATTACTGTCAGCAGAGTAGGGAAGTACTTCCGGACG
 G  S  G  S  G  T  D  F  T  L  T  I  S  S  L  Q  A  E  D  V  A  T  Y  Y  C  Q  Q  S  R  E  L  R  T
                  70                         80                         90                    94 96
```

Fig. 18 (cont.)

```
       310       320       330
TTCGGTCAGGGCACCAAGCTGGAAATCAAA

F  G  Q  G  T  K  L  E  I  K
   100                106  A
```

CDR definitions and protein sequence numbering according to Kabat. CDR nucleotide and protein sequences are highlighted in red. Variant 2 amino acids changed from the original hybridoma sequence are highlighted in green.

Fig. 19

*PTA-2358 Variable Light Chain Nucleotide (SEQ ID NO: 44) and Amino Acid (SEQ ID NO: 28) Sequences VK Variant 3*

```
         10        20        30        40        50        60        70        80        90       100
GACATTGTGATGACACAGTCTCCTGACTCCTTAGCTGTATCTCTGGGGGAGAGGGCCACCATCAACTGCAGGGCCAGTAAAAGTGTCAGTACATCTGGCT

D  I  V  M  T  Q  S  P  D  S  L  A  V  S  L  G  E  R  A  T  I  N  C  R  A  S  K  S  V  S  T  S  G
                      10                    15                    20                    27 A B C D 110       120       130       140       150       160       170       180       190       200
ATAGTTTTATGCACTGGTACCAACAGAAACCAGGACAGCCACCCAAACTCCTCATCTATCTTGCATCCAACCTGGAATCTGGGGTCCCTGACAGGTTCAG

Y  S  F  M  H  W  Y  Q  Q  K  P  G  Q  P  P  K  L  L  I  Y  L  A  S  N  L  E  S  G  V  P  D  R  F  S
   30                    35                    40                    45                    50                    60

210       220       230       240       250       260       270       280       290       300
TGGCAGTGGGTCTGGGACAGACTTCACCCTCACCATCAGCAGCCTGCAGGCCGAGGATGTGGCAGTGTATTACTGTCAGCAGAGTAGGGAAGTTCCGGACC

```
         310       320       330
TTCGGTCAGGGCACCAAGCTGGAAATCAAA
 F  G  Q  G  T  K  L  E  I  K
    100              106    A
```

CDR definitions and protein sequence numbering according to Kabat. CDR nucleotide and protein sequences are highlighted in red. Variant 3 amino acids changed from the original hybridoma sequence are highlighted in green

C6f1-pFUSE construct (SEQ ID NO: 51)

```
128 LVNEEATGQFHVYPELPKPSISSNHSNPVE
158 DKDAVAFTCEPEVQNTTYLWWVNGQSLPVS
188 PRLQLSNGNMTLTLLSVKRNDAGSYECEIQ
218 NPASANHSDPVTLNVLYGPDGPTISPSKAN
248 YRPGENINLSCHAASNPPAQYSWFINGTFQ
278 QSTQELFIPNITVNNSGSYMCQAHNSATGL
308 NRTTVTMITV 317
```

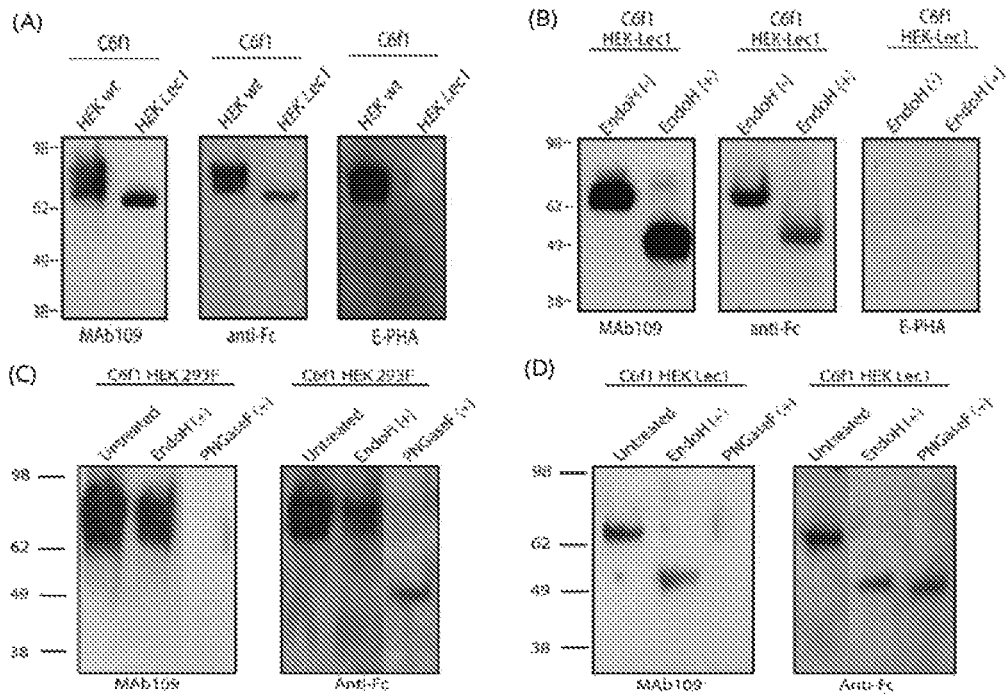

MAb109 epitope expressed in HEK Lec1 cells is EndoH resistant. (A) Immunoblots of recombinantly expressed C6f1 in HEK wild-type (wt) and HEK Lec1 cell lines (B) MAb109 epitope is sensitive to EndoH in HEK Lec1 cells, which lack bisected glycans as demonstrated by absence of E-PHA staining. (C) MAb109 epitope expressed in HEK-293F is EndoH resistant and PNGaseF sensitive (D) Addition of the MAb109 glycoepitope causes resistance to cleavage by EndoH on high-mannose glycans of HEK Lec1 expressed C6f1.

Fig. 28

CEACAM6 fragment 1 glycans expressed in HEK Lec1 AFTER endo H treatment

LVNEEATGQFHVYPELPKPSISSNNSNPVEDKDAVAFTCEPEVQNTTYLWWVNGQSLPVSPRLQ
(SEQ ID NO: 52)

LSNGNMTLTLLSVKRNDAGSYECEIQNPASANRSDPVTLNVLYGPDGPTISPSKANYRPGENL
(SEQ ID NO: 53)

NLSCHAASNPPAQYSWFINGTFQQSTQELFIPNITVNNSGSYMCQAHNSATGLNRTTVTMITV
(SEQ ID NO: 54)

Fig. 29

Sequence alignment of C-termini for CEACAM5 (SEQ ID NO: 55), 6 (SEQ ID NO: 56), and 8 (SEQ ID NO: 57)

```
CEACAM5  194  LQLSNGNRTLTLFNVTRNDSASYKCETQ  228
CEACAM6  131  LQLSNGNMTLTLLSVKRNDAGSYECEIQ  218
CEACAM8  191  LQLSNGNRTLTLLSVTRNDVGPYECEIQ  218

CEACAM5  229  NPVSARRSDSVILNVLYGPDAPTISPLNTS  248
CEACAM6  219  NPASANRSDPVTLNVLYGPDGPTISPSKAN  248
CEACAM8  219  NPASANFSDPVTLNVLYGPDAPTISPSDTY  248

CEACAM5  249  YRSGENLNLSCHAASNPPAQYSWFVNGTFQ  278
CEACAM6  249  YRPGENLNLSCHAASNPPAQYSWRINGTFQ  278
CEACAM8  249  YHAGVNLNLSCHAASNPPSYYSWSVNGTFQ  278

CEACAM5  279  QSTQELFIPNITVNNSGSYTCQAHNSDTGL  308
CEACAM6  279  QSTQELFIPNITVNNSGSYMCQAHNSATGL  308
CEACAM8  279  QYTQKLFIPRITKNSGSYACHTINGATGR  308

CEACAM5  309  NRTTVTTITV  318
CEACAM6  309  NRTTVTMITV  318
CEACAM8  309  NRTTVRMITV  318
```

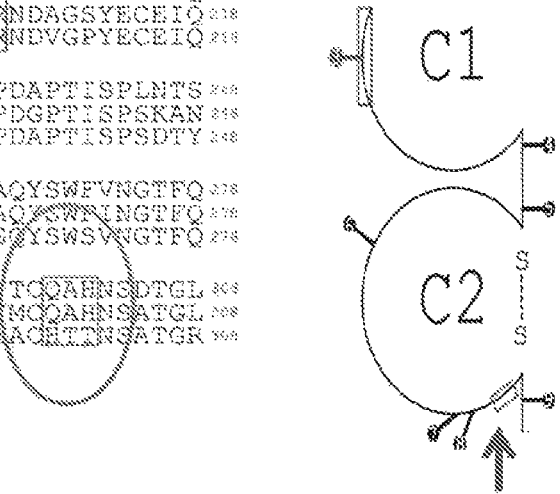

Fig. 30

Site-directed mutagenesis of C6f1
$^{300}$QAH$^{302}$ → $^{300}$HTT$^{302}$ abolishes MAb109 reactivity

- Three amino acids from CEACAM6 sequence were mutated to CEACAM8 sequence

- MAb109 reactivity was essentially abolished–(overnight over-exposure of film)

Fig. 31

When three amino acids of CEACAM8 are mutated, the MAb109 glycoepitope becomes expressed

- CEACAM8 contains the necessary N-linked site for glycoepitope expression but does not express it when transiently expressed in HEK-293 cells

- Mutation of amino acids 300-302 of CEACAM8, HTT to QAH, leads to positive reactivity for the MAb109 glycoepitope

Fig. 32

Mutation of CEACAM8 amino acids downstream of CEACAM6 epitope glycosylation site leads to MAb109 epitope expression

| Mr(K) | pFUSE | C8f1 H300Q | C8f1 T302H | C8f1 H300Q/T302H | C8f1 HTT to QAH | C6f1 (QAH)* | |
|---|---|---|---|---|---|---|---|
| 98 — | | | | ▬ | ▬ | ▬ | MAb109 |
| 62 — | | | | | | | |

Fig. 33

Deletion of each N-linked sequon in C6f1 (N to Q) (SEQ ID NO: 51)

```
129 LVNEEATGQFHVYPELPKPSISSNNSNPVE     (N152)
159 DKDAVAFTCEPEVQNTTYLWWVNGQSLPVS     (N173)
189 PRLQLSNGNMTLTLLSVKRNDAGSYECEIQ     (N197)
219 NPASANRSDPVTLNVLYGPDGPTISPSKAN     (N224)
249 YRPGENLNLSCHAASNPPAQYSWFINGTFQ     (N256...N274)
279 QSTQELFIPNITVNNSGSYMCQAHNSATGL     (N288..N292)
309 NRTTVTMITV                          (N309)
```

wt  152  173  197  224  256  274  288  292  309

Loss of CT109 binding when 309N is mutated

⇐ Probed with CT109

⇐ Probed with an

Mutation of only one AsnXSer/Thr sequon eliminates MAb109 binding activity (SEQ ID NO: 51)

$^{129}$LVNEEATGQFHVYPELPKPSISSNNSNPVE
$^{153}$DKDAVAFTCEPEVQNTTYLWWVNGQSLPVS
$^{189}$PRQLSNGNMTLTLLSVKRNDAGSYECEIQ
$^{219}$NPASANRSDPVTLNVLYGPDGPTISPSKAN
$^{249}$YRPGENLNLSCHAASNPPAQYSWFINGTFQ
$^{279}$QSTQELFIPNITVNNSGSYMCQAHNSATGL
$^{309}$NRTVTMITV$^{318}$ 152, 173, 197, 224, 256, 274, 288, 292, 309

| SEQ ID NOS 77-151, respectively, in order of appearance | |
|---|---|
| | QAHNSATGLNPTTVTMITV |
| | QAHNSATGLQRTTVTMITV |
| | QAHNSATGLARTTVTMITV |
| | HAHNSATGLNPTTVTMITV |
| | QATNSATGLNPTTVTMITV |
| | QAHQSATGLNRTTVTMITV |
| | QAHNAATGLNPTTVTMITV |
| | (illegible) |
| | QAHNSATGPNRTTVTMITV |
| | QAHNSATGLNPTTVTMITV |
| | QAHNSATGLNRTTVTMITV |
| | QAHNSATGLNRATVTMITV |
| | QAHNSATGLNPTTVAMITV |
| | QAHNSATGLNRTAAMITV |
| | QAHNSATGLNRTVPATTV |
| | QAHNSATGLNPTTVTMATV |
| | QAHNSATGLNRTTVTMIAV |
| | QAHNSATGLNRTTVTMITA |
| | HITNSATGLNRTTVTMITV |
| | CQAHNSATGLNRTTVTMITV |
| | AQAHNSATGLNPTTVTMITV |
| | MCQAHNSATGLNRTTVTMITV |
| | ACQAHNSATGLNRTTVTMITV |
| | (illegible) |
| | YMCQAHNSATGLNPTTVTMITV |

Mutations of 300-318 peptide segment and measurement of MAb109 binding

```
                GlcNAc
                  |
       YMCQAHNSATGLNRTTVTMITV
        300    305    309      318
       (SEQ ID NO: 101)
```

Red = No 109 binding
Green = 109 binding
Orange = reduced 109 binding

Thr 311 changed to Ser311 still yields active epitope, while A311 is inactive, presumably because of lack of GlcNAc on Asn309

Fig. 37

Synthetic peptide and glycopeptide did not inhibit at 30 μM

Q A H N S A T G L N R T T V T M I T V S G S A P V L R (SEQ ID NO: 102)

$$\text{GlcNAc}$$
$$|$$
Q A H N S A T G L N R T T V T M I T V S G S A P V L R R (SEQ ID NO: 102)

Fig. 38

Synthesis of cDNAs encoding C-terminal peptides and expression in Lec 1 HEK cells

At the C-terminus there is a short linker, TEV cleavage site, and GFP.

GPTISPSKANYRPGENLNLSQHAASNPPAQYSWFNGTFQQSTQELFIPNITVNNSGSYMCQAHNSATGLNRTTVTMITV----
(SEQ ID NO: 103)                                                    #6   ACTIVE

GPTISPSKANYRPGENLNLSAHAASNPPAQYSWFNGTFQQSTQELFIPNITVNNSGSYMCQAHNSATGLNRTTVTMITV----
(SEQ ID NO: 104)                                                    #12  NOT ACTIVE

GTFQQSTQELFIPNITVNNSGSYMCQAHNSATGLNRTTVTMITV---
                         (SEQ ID NO: 105)                           #10  NOT ACTIVE

QAHNSATGLNRTTVTMITV----
                                              (SEQ ID NO: 77)       #11  NOT ACTIVE

Fig. 39

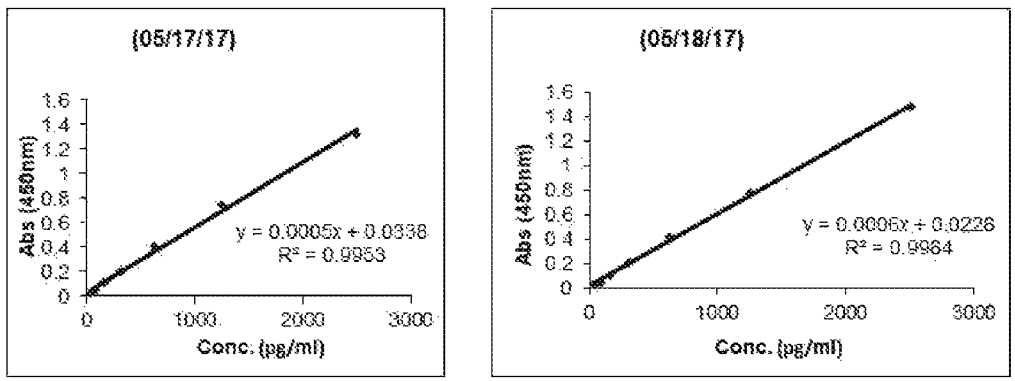

ELISA was set up for detecting serum CEACAM6. A sandwich ELISA method was established using Mab109 (2 ug/ml) as capture Ab and biotinylated rabbit anti-CEACAM6 polyclonal antibody (1:3000) that showed very little cross-reactivity with rCEACAM5 as detection Ab. Full length human CEACAM6 was expressed, purified, and used as a standard. Avidin–HRP was from abcam (1:10,000).

The results were calculated based on these standard curves. A normal serum and pancreatic cancer serum (from Tgen long time ago) were set up along with clinical trial samples and used as control:
Normal serum: 1.0 and 3.5 ng/ml
Cancer serum: 154.34 and 146.64 ng/ml

Fig. 40

Establishing ELISA to detect serum CEACAM6 glycoepitope using MAb109

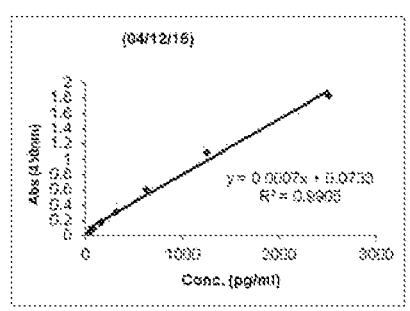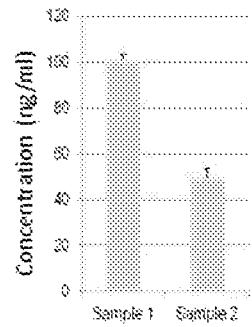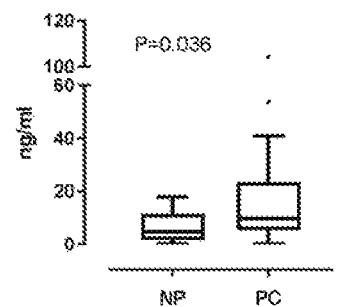

The minimum detectable amount: 39.1 pg/ml

Sample 1: rCEACAM6 (0.1ug/ml) (n=8)
Sample 2: diluted sample1 (1:2) (n=7)

NP: median: 4.88 (range: 0.2-17.8 ng/ml, n= 20)
PC: median: 9.92 (range: 0.2-104.1 ng/ml, n= 29)

ELISA was set up for detecting serum CEACAM6. A sandwich ELISA method was established using Mab109 (2 ug/ml) as capture Ab and biotinylated rabbit anti-CEACAM6 polyclonal antibody (1:3000) that showed very little cross-reactivity with rCEACAM5 as detection Ab. Full length human CEACAM6 was expressed, purified, and used as a standard. Avidin –HRP was from abcam (1:10,000)

Fig. 41

First Test (4/15/16 and 4/27/16):

1. NP: median: 4.88 (range: 0.2-17.8 ng/ml, n= 20)
2. CP: median: 7.79 (range: 1.21-30.5 ng/ml, n= 8)
3. PC: median: 9.92 (range: 0.2-104.1 ng/ml, n= 29)

NP, Non-diseased Patients; CP, Chronic Pancreatitis; PC, Pancreatic Carcinoma

Second time test (all samples 05/27/16):

1. NP: median: 11.4 (range: 2.90-29.5 ng/ml, n=20)
2. CP: median: 13.0 (range: 1.4-36.0 ng/ml, n=19)
3. PC: median: 15.5 (range: 2.90-113.0 ng/ml, n=29)

NP, Non-diseased Patients; CP, Chronic Pancreatitis; PC, Pancreatic Carcinoma

… # ANTIBODY CONSTRUCTS AND METHODS OF TREATING CANCER

CROSS-REFERENCE TO RELATED APPLICATIONS

This application is a U.S. national phase application filed under 35 U.S.C. § 371 of International Application No. PCT/US18/200500, which was filed Feb. 27, 2018, and which claims the benefit of the filing date of U.S. Provisional Application No. 62/463,868, which was filed Feb. 27, 2017. The entire content of these applications is hereby incorporated by reference herein.

SEQUENCE LISTING

The instant application contains a Sequence Listing which has been submitted electronically in ASCII format and is hereby incorporated by reference in its entirety. Said ASCII copy, created on Feb. 27, 2018, is named G6527-00300_SL.txt and is 74,291 bytes in size.

BACKGROUND

Antibodies are a well-established therapeutic modality. Initially, murine antibodies were used as therapeutics but their utility was hampered by human immune responses to mouse-specific sequences. This response was ameliorated by the use of humanized antibodies, in which the mouse specific sequences were replaced with human ones. Later modifications included the covalent attachment of toxic molecules to form antibody-drug conjugates (ADC), two different binding sites to form bivalent antibodies, as well as truncated antibodies that have one binding site for antigen and the other to the CD3 molecule on T cells (bispecific T cell engager or BITE antibodies). The antibody combining site has been used to form chimeric antigen receptors (CARs) that can be introduced into T cells, and other immune cells such as Natural Killer (NK) cells or Natural Killer T (NKT) cells permitting the transfected cells to recognize a desired antigen. This approach equips the transfected cells with an immune receptor that does not require recognition of the major histocompatibility complex (MHC), which tumors can modify to avoid immune recognition. Moreover, upon engagement of the antibody with the targeted cancer cells, the transfected cells (T cells, NK or NKT) get activated and their killing capabilities are enhanced.

SUMMARY

Described herein are antibody reagents, e.g., humanized antibodies, BITEs and CARs, that specifically bind to antigens present on the surface of cancer cells. When expressed by T cells, such CARs permit the recognition and targeting of cancer cells by the immune system. Accordingly, provided herein are compositions and methods relating to the use of these modified antibodies and CAR-T therapy in the treatment of cancer.

In one aspect, described herein is an isolated antibody, antigen-binding portion thereof, or chimaeric antigen receptor (CAR), the antibody, antigen-binding portion thereof, or CAR comprising one or more heavy and light chain complimentarity determining regions (CDRs) selected from the group consisting of:
  a. a light chain CDR1 having the amino acid sequence of SEQ ID NO: 4 or 10;
  b. a light chain CDR2 having the amino acid sequence of SEQ ID NO: 5 or 11;
  c. a light chain CDR3 having the amino acid sequence of SEQ ID NO: 6 or 12;
  d. a heavy chain CDR1 having the amino acid sequence of SEQ ID NO: 1 or 7;
  e. a heavy chain CDR2 having the amino acid sequence of SEQ ID NO: 2 or 8; and
  f. a heavy chain CDR3 having the amino acid sequence of SEQ ID NO: 3 or 9.

In some embodiments, the isolated antibody, antigen-binding portion thereof, or CAR can comprise the light chain complimentarity determining regions (CDRs):
  a. a light chain CDR1 having the amino acid sequence of SEQ ID NO: 4;
  b. a light chain CDR2 having the amino acid sequence of SEQ ID NO: 5; and
  c. a light chain CDR3 having the amino acid sequence of SEQ ID NO: 6.

In some embodiments, the isolated antibody, antigen-binding portion thereof, or CAR can comprise the light chain complimentarity determining regions (CDRs):
  a. a light chain CDR1 having the amino acid sequence of SEQ ID NO: 10;
  b. a light chain CDR2 having the amino acid sequence of SEQ ID NO: 11; and
  c. a light chain CDR3 having the amino acid sequence of SEQ ID NO: 12.

In some embodiments, the isolated antibody, antigen-binding portion thereof, or CAR can comprise the heavy chain complimentarity determining regions (CDRs):
  a. a heavy chain CDR1 having the amino acid sequence of SEQ ID NO: 1;
  b. a heavy chain CDR2 having the amino acid sequence of SEQ ID NO: 2; and
  c. a heavy chain CDR3 having the amino acid sequence of SEQ ID NO: 3.

In some embodiments, the isolated antibody, antigen-binding portion thereof, or CAR can comprise the heavy chain complimentarity determining regions (CDRs):
  d. a heavy chain CDR1 having the amino acid sequence of SEQ ID NO: 7;
  e. a heavy chain CDR2 having the amino acid sequence of SEQ ID NO: 8; and
  f. a heavy chain CDR3 having the amino acid sequence of SEQ ID NO: 9.

In some embodiments, the isolated antibody, antigen-binding portion thereof, or CAR can comprise the complimentarity determining regions (CDRs):
  a. a light chain CDR1 having the amino acid sequence of SEQ ID NO: 4;
  b. a light chain CDR2 having the amino acid sequence of SEQ ID NO: 5;
  c. a light chain CDR3 having the amino acid sequence of SEQ ID NO: 6;
  d. a heavy chain CDR1 having the amino acid sequence of SEQ ID NO: 1;
  e. a heavy chain CDR2 having the amino acid sequence of SEQ ID NO: 2; and
  f. a heavy chain CDR3 having the amino acid sequence of SEQ ID NO: 3.

In some embodiments, the isolated antibody, antigen-binding portion thereof, or CAR can comprise the complimentarity determining regions (CDRs):
  a. a light chain CDR1 having the amino acid sequence of SEQ ID NO: 10;

b. a light chain CDR2 having the amino acid sequence of SEQ ID NO: 11;
c. a light chain CDR3 having the amino acid sequence of SEQ ID NO: 12;
d. a heavy chain CDR1 having the amino acid sequence of SEQ ID NO: 7;
e. a heavy chain CDR2 having the amino acid sequence of SEQ ID NO: 8; and
f. a heavy chain CDR3 having the amino acid sequence of SEQ ID NO: 9.

In some embodiments, the isolated antibody, antigen-binding portion thereof, or CAR can comprise a heavy chain having a sequence selected from SEQ ID NOs: 13-17 and 21-25. In some embodiments, the isolated antibody, antigen-binding portion thereof, or CAR can comprise a light chain having a sequence selected from SEQ ID NOs: 18-20 and 26-28. In some embodiments, the isolated antibody, antigen-binding portion thereof, or CAR can comprise a heavy chain having a sequence selected from SEQ ID NOs: 13-17 and a light chain having a sequence selected from SEQ ID NOs: 18-20. In some embodiments, the isolated antibody, antigen-binding portion thereof, or CAR can comprise a heavy chain having a sequence selected from SEQ ID NOs: 21-25 and a light chain having a sequence selected from SEQ ID NOs: 26-28. In some embodiments, the isolated antibody, antigen-binding portion thereof, or CAR can comprise a conservative substitution in a sequence not comprised by a CDR.

In some embodiments the antibody or polypeptide can be selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a bispecific T-cell engager (BiTE).

In some embodiments, the isolated antibody, antigen-binding portion thereof, or CAR can specifically bind to an antigen on the surface of a cancer cell. In some embodiments, the isolated antibody, antigen-binding portion thereof, or CAR can specifically bind to an antigen on the surface of a cancer stem cell and does not specifically bind to normal intestinal cells.

In one aspect, described herein is a bispecific T-cell engager (BiTE) comprising two binding sites, the first binding site comprising an antigen-binding portion as described herein and the second binding site comprising an antigen-binding portion of an antibody that specifically binds to a T cell. In some embodiments, the antigen-binding portion of an antibody that specifically binds to a T cell can be an anti-CD3 antigen-binding portion of an antibody. In some embodiments, at least one antigen-binding portion can be an scFv.

In one aspect, described herein is a pharmaceutical composition comprising an isolated antibody, antigen-binding portion thereof, CAR, or BiTE as described herein and a pharmaceutically acceptable carrier.

In one aspect, described herein is a nucleic acid encoding an isolated antibody, antigen-binding portion thereof, CAR, or BiTE as described herein. In some embodiments, the nucleic acid can comprise a sequence selected from SEQ ID NOs: 29-44. In some embodiments, the nucleic acid can be a cDNA.

In one aspect, described herein is a cell comprising the isolated antibody, antigen-binding portion thereof, CAR, or BiTE as described herein. In some embodiments, the cell can be an immune cell. In some embodiments, the cell can be selected from the group consisting of a T cell; a NK cell; and a NKT cell. In some embodiments, the isolated antibody, antigen-binding portion thereof, or CAR can be expressed on the cell surface.

In one aspect, described herein is a method of treating cancer in a subject in need thereof, the method comprising administering a cell as described herein to the subject. In one aspect, described herein is a method of treating cancer in a subject in need thereof, the method comprising administering a nucleic acid as described herein to the subject, wherein the subject's T-cells are caused to express the polypeptide encoded by the nucleic acid. In some embodiments, the cancer can be selected from the group consisting of: pancreatic cancer; lung cancer; non-small cell lung cancer; colon cancer; breast cancer; liver cancer; and prostate cancer.

Also provided are methods of detecting CEACAM6 in a biological sample from a patient. The method can include contacting the biological sample from the patient with a first antibody that specifically binds to a first epitope comprising a glycopeptide to form a first complex between the first antibody and the CEACAM6; contacting the first complex with a second antibody that specifically binds to a second epitope, wherein the first and second epitopes are different, to form a second complex, wherein the second complex comprises the first antibody, CEACAM6, and the second antibody; and detecting the second complex, thereby detecting CEACAM6. The biological sample can be a serum, blood, or plasma sample. The first epitope comprises can include SEQ ID NO. 51 or a fragment thereof, SEQ ID NO. 101 or a fragment thereof, or SEQ ID NO. 77 or a fragment thereof. The second antibody can comprise the detectable label. The detectable label can be selected from the group consisting of biotin group, an enzyme, a dye, a luminescent group, and a fluorescent group. In some embodiments, the first antibody can be immobilized on a solid support. The first antibody can be a humanized antibody. The humanized antibody can an amino acid sequence of any of SEQ ID NOs. 1-28. The patient can be a patient having or at risk for pancreatic cancer. In some embodiments, the patient can be a patient having pancreatitis.

1.0 µg PTA-2358 VH3/VK1 IgG1 antibody Lane 7: 1.0 µg PTA-2358 VH4/VK1 IgG1 antibody Lane 8: 1.0 µg PTA-2358 VH4/VK2 IgG1 antibody Lane 9: 1.0 µg PTA-2358 VH5/VK1 IgG1 antibody Lane 10: 1.0 µg PTA-2358 VH5/VK2 IgG1 antibody.

Figure 3A:
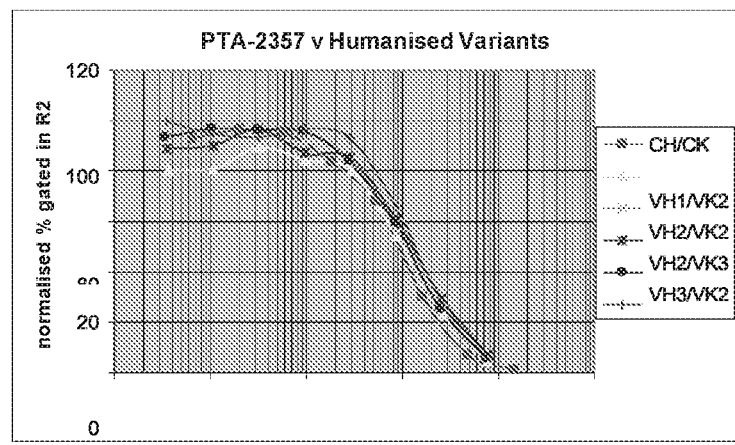
Figure 3B:
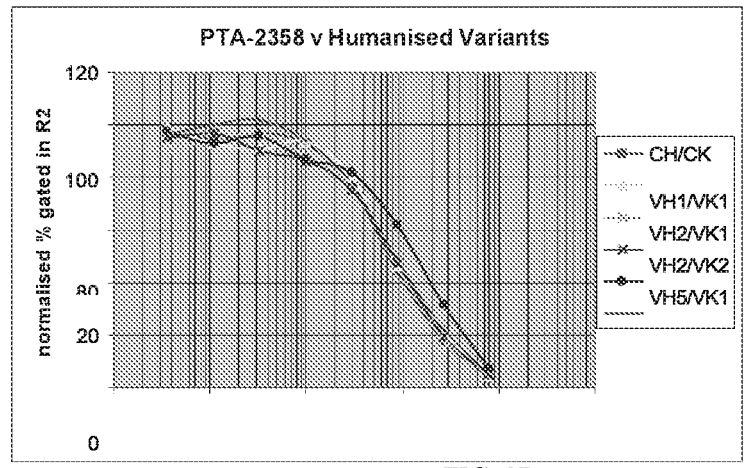
Figure 3C:
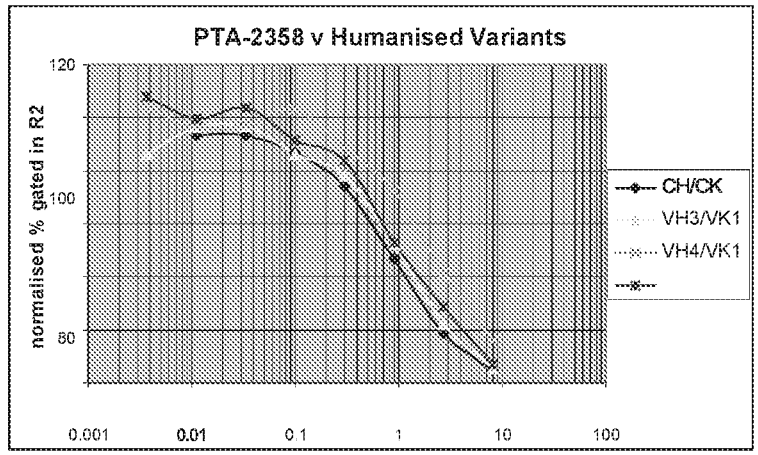

FIGS. 3A-3C depict competition assay and flow cytometry analysis using NS0-derived humanized variant antibodies binding to Small Cell Lung Cancer (CSCLC) cells. Varying concentrations of each humanized antibody were mixed with a fixed concentration of mouse antibody (0.1 µg/ml PTA-2357 or 0.3 µg/ml PTA-2358) and incubated with CSCLC cells. Binding was detected via FITC conjugated goat anti-mouse Fc. Data was plotted as normalized % positive events (gated in R2). (FIG. 3A) PTA-2357 lead humanized antibodies. (FIG. 3B) and (FIG. 3C) PTA-2358 lead humanized antibodies.

FIG. 4 depicts the PTA-2357 Variable Heavy Chain Nucleotide and Amino Acid Sequences VH Variant 1.

FIG. 5 depicts the PTA-2357 Variable Heavy Chain Nucleotide and Amino Acid Sequences VH Variant 2.

FIG. 6 depicts the PTA-2357 Variable Heavy Chain Nucleotide and Amino Acid Sequences VH Variant 3.

FIG. 7 depicts the PTA-2357 Variable Heavy Chain Nucleotide and Amino Acid Sequences VH Variant 4.

FIG. 8 depicts the PTA-2357 Variable Heavy Chain Nucleotide and Amino Acid Sequences VH Variant 5.

FIG. 9 depicts the PTA-2357 Variable Heavy Chain Nucleotide and Amino Acid Sequences VK Variant 1.

FIG. 10 depicts the PTA-2357 Variable Heavy Chain Nucleotide and Amino Acid Sequences VK Variant 2.

FIG. 11 depicts the PTA-2357 Variable Heavy Chain Nucleotide and Amino Acid Sequences VK Variant 3.

FIG. 12 depicts the PTA-2358 Variable Heavy Chain Nucleotide and Amino Acid Sequences VH Variant 1.

FIG. 13 depicts the PTA-2358 Variable Heavy Chain Nucleotide and Amino Acid Sequences VH Variant 2.

FIG. 14 depicts the PTA-2358 Variable Heavy Chain Nucleotide and Amino Acid Sequences VH Variant 3.

FIG. 15 depicts the PTA-2358 Variable Heavy Chain Nucleotide and Amino Acid Sequences VH Variant 4.

FIG. 16 depicts the PTA-2358 Variable Heavy Chain Nucleotide and Amino Acid Sequences VH Variant 5.

FIG. 17 depicts the PTA-2358 Variable Heavy Chain Nucleotide and Amino Acid Sequences VK Variant 1.

FIG. 18 depicts the PTA-2358 Variable Heavy Chain Nucleotide and Amino Acid Sequences VK Variant 2.

FIG. 19 depicts the PTA-2358 Variable Heavy Chain Nucleotide and Amino Acid Sequences VK Variant 3.

Figure 20:
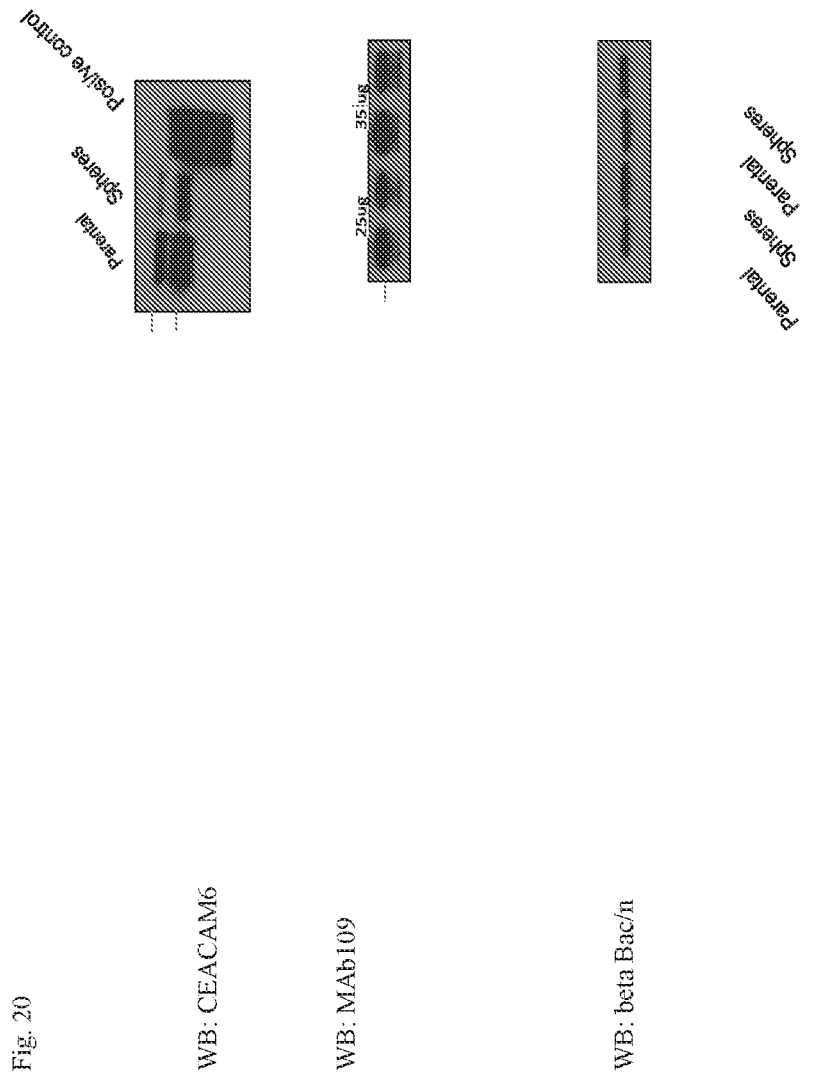

FIG. 20 demonstrates that tumorspheres grown from HTK29 cells show binding by MAb 109. HT29 human colorectal carcinoma cells were grown in stem cell culture media for 10 days and tumorspheres (enriched with cancer stem cells) were formed. Parental and tumorspheres were collected for Western blotting. Top, blotting of total HT.29 cell lysates and tumorspheres (and Capan.1 cell lysates expressing CEACAM6 as a positive control) after SDS.PAGE using anti.CEACAM6 polypeptide antibody (control; clone 9A6 (Santa Cruz #sc. 59899); Bottom, two protein concentrations of HT29 cell lysates or tumorspheres grown for 10 days (25 mg and 35 mg) were subjected to SDS PAGE and blotted with MAb 109 or beta actin.

Figure 21:
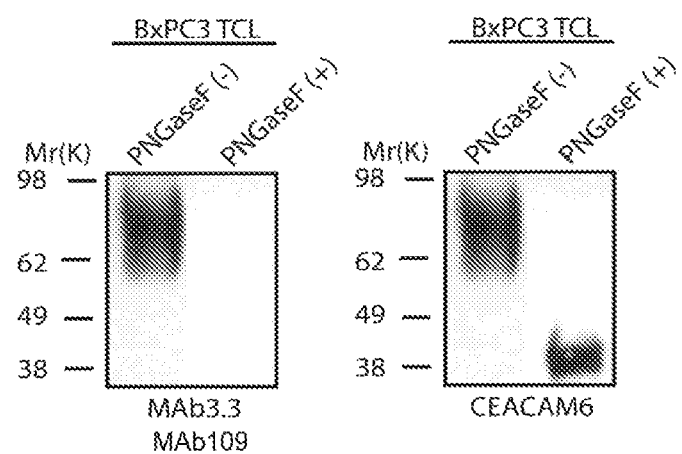

FIG. 21 depicts the results of an immunoblot analyzing the reactivity of MAb 109 against the pancreatic carcinoma cell line, BxPC3 TCL, following treatment with PNGaseF.

Figure 22:
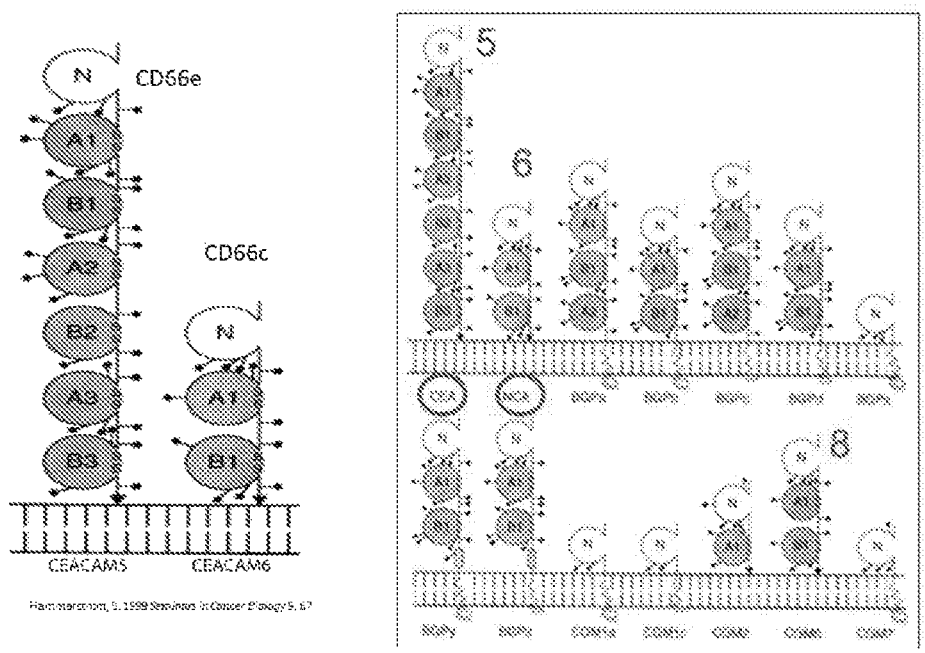

FIG. 22 depicts the structures of the Carcinoembryonic Antigen (CEA) family.

Figure 23:
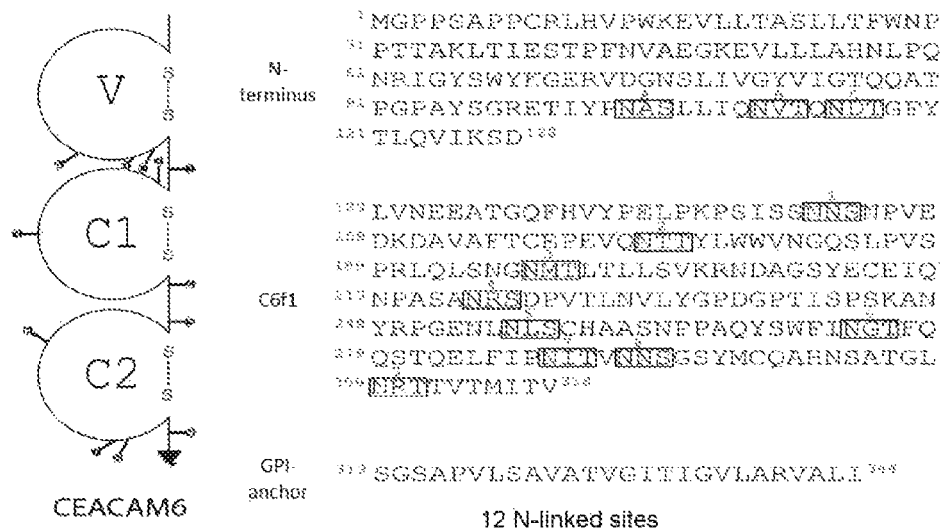

FIG. 23 depicts the structure of CEACAM6, the amino acid sequence of CEACAM6, and the 12 potential N-linked glycosylation sites within the amino acid sequence.

Figure 24:
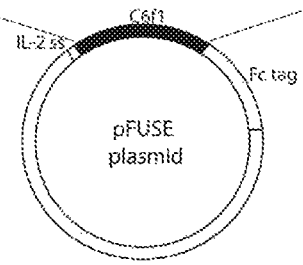

FIG. 24 depicts the C6f1-pFUSE construct (SEQ ID NO: 51).

Figure 25:
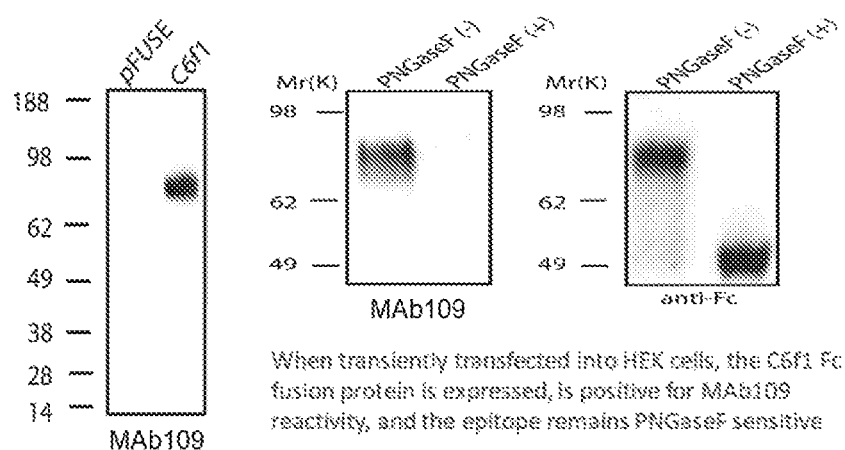

FIG. 25 depicts results of an immunoblotting experiment showing that HEK-293 cells contain the biosynthetic machinery to synthesize the MAb 109 glycoepitope.

Figure 26:
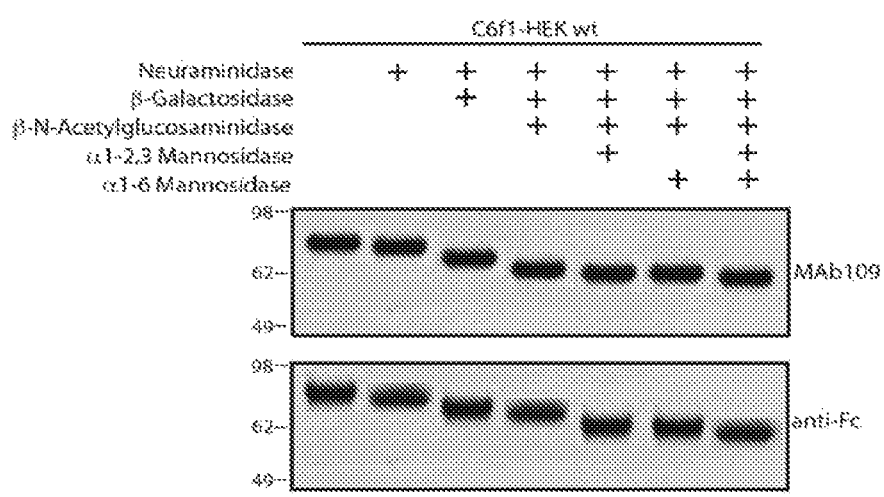

FIG. 26 depicts the results of an immunoblotting experiment showing the treatment of HEK wild type C6f1 with various glycosidases.

Figure 27:
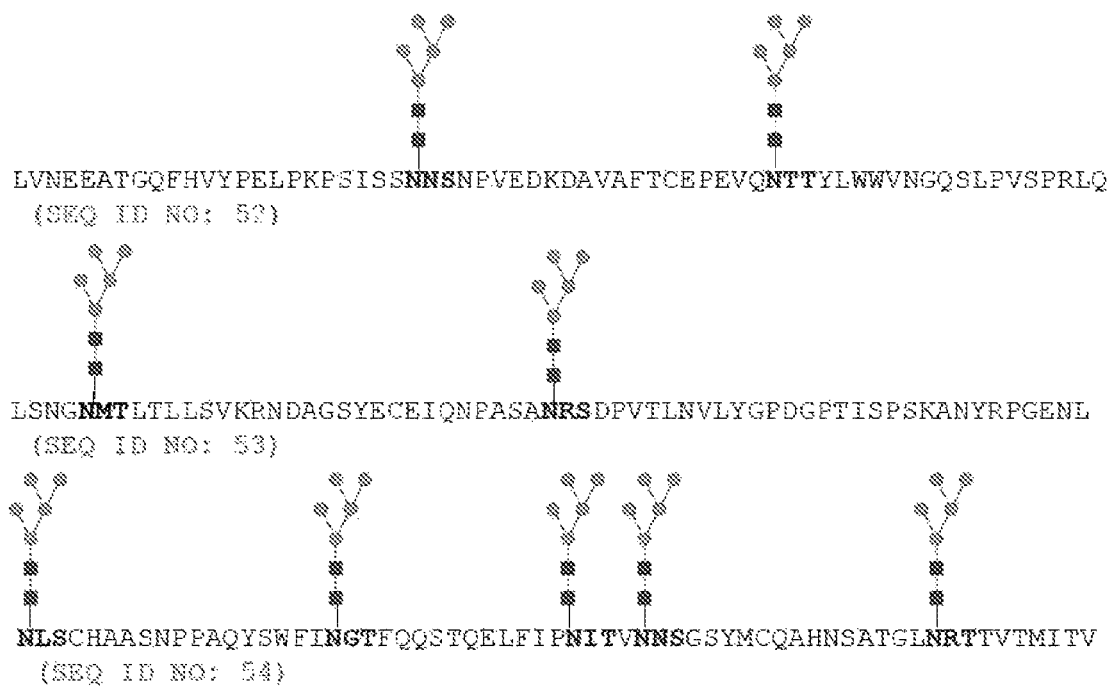

FIG. 27 depicts CEACAM6 fragment 1 glycans expressed in HEK Lec1 cells.

FIG. 28 depicts an immunoblotting experiment showing that the MAb 109 epitope expressed in HEK Lec1 cells is EndoH resistant.

FIG. 29 depicts CEACAM6 fragment 1 glycans expressed in HEK Lec1 cells after Endo H treatment.

FIG. 30 depicts a sequence alignment of the C-termini for CEACAM5 (SEQ ID NO: 55) CEACAM6 (SEQ ID NO: 56) and CEACAM8 (SEQ ID NO: 57).

FIG. 31 depicts the results of an immunoblotting experiment showing that site-directed mutagenesis of C6f1 $^{300}$QAH$^{302}$ to $^{300}$HTT$_{302}$ abolishes MAb 109 reactivity.

FIG. 32 depicts the results of an immunoblotting experiment showing that when three amino acids of CEACAM8 are mutated, the MAb 109 glycoepitope becomes expressed.

FIG. 33 depicts the results of an immunoblotting experiment showing that mutation of CEACAM8 amino acids downstream of the CEACAM6 epitope glycosylation site leads to MAb 109 epitope expression.

FIG. 34 depicts the results of an immunoblotting experiment showing the effect of deletion of each N-linked sequon in C6f1 (N to Q) (SEQ ID NO: 51).

FIG. 35 depicts a structural analysis showing that mutation of only one AsnXSer/Thr sequon eliminates MAb 109 binding activity (SEQ ID NO: 51).

FIG. 36 summarizes additional mutations in SEQ ID NO: 51.

FIG. 37 summarizes mutations of 300-318 peptide segment and measurements of MAb 109 binding.

FIG. 38 summarizes the results of an experiment showing that a synthetic peptide (SEQ ID NO: 102) and a synthetic glycopeptide (SEQ ID NO: 102) did not inhibit MAb 109 binding at 30 micromolar.

FIG. 39 summarizes the results of an experiment showing effect of C-terminal peptides on MAb 109 binding activity.

FIG. 40 depicts the results of an ELISA for detection of CEACAM6 in human serum.

FIG. 41 depicts the results of an ELISA for detection of CEACAM6 glycoepitope in human serum using MAb 109.

Figure 42:
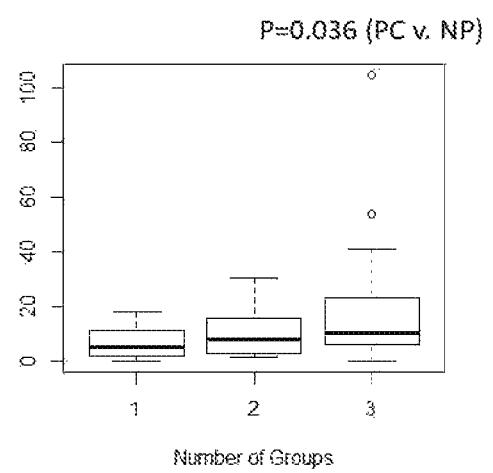

FIG. 42 depicts the results of an ELISA for detection of CEACAM6 glycoepitope using MAb 109 in a first set of sera from nondiseased patients, patients with chronic pancreatitis, and patients with pancreatic carcinoma.

Figure 43:
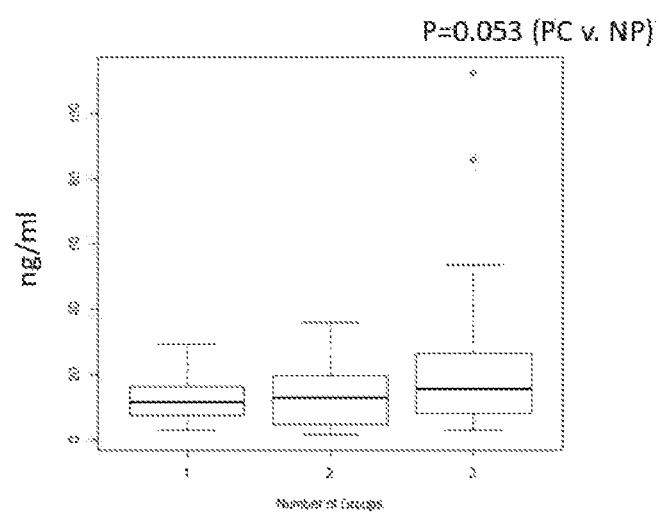

FIG. 43 depicts the results of an ELISA for detection of CEACAM6 glycoepitope using MAb 109 in a second set of sera from nondiseased patients, patients with chronic pancreatitis, and patients with pancreatic carcinoma.

DETAILED DESCRIPTION

Described herein are antibodies and related polypeptides that bind specifically to an antigen present on cancer cells, e.g., on lung cancer cells, colon cancer cells, or pancreatic cancer cells. The antigen, CEACAM6 (also known as CD66c, "Cluster of Differentiation 66c," carcinoembryonic antigen related cell adhesion molecule 6, CEAL, and NCA) is a transmembrane glycoprotein belonging the immunoglobulin superfamily. An exemplary CEACAM6 amino acid sequence can be GenBank NP_002474.4. An exemplary mRNA sequence encoding CEACAM6 can be GenBank NM_002483.6. An exemplary antibody that specifically binds to CEACAM6 can be the mouse antibody MAb 109. In some embodiments, an exemplary humanized antibody that specifically binds to CEACAM6 can be based on the mouse monoclonal antibody, MAb 109. Such antibodies and polypeptides can permit, e.g., the diagnosis, prognosis, and/or treatment of cancer. In some embodiments, the technology described herein relates to bispecific T cell engager (BITE) antibodies. In some embodiments, the technology described herein relates to chimeric antigen receptors (CARs) and CAR-T therapy for cancer.

In some embodiments, the technology described herein relates to antibodies and/or polypeptides comprising an antigen-binding portion of an antibody that binds an antigen such as a cancer cell surface antigen and another antigen-binding portion of the same antibody that binds a. "bispecific T cell engager" or "BITE" refers to an antibody that simultaneously binds a cancer antigen and an activating antigen on an immune effector cell. As used herein, "bispecific T cell engager" or "BITE" refers to an antibody that simultaneously binds a cancer antigen and an activating antigen on an immune effector cell. As used herein, "chimeric antigen receptor" or "CAR" refers to an artificially constructed hybrid polypeptide comprising an antigen-binding domain (e.g. an antigen-binding portion of an antibody (e.g. a scFV)) linked to a cell signaling and/or cell activation domain. In some embodiments the cell-signaling domain can be a T-cell signaling domain. In some embodiments, the cell activation domain can be a T-cell activation domain. CARs have the ability to redirect the specificity and reactivity of T cells and other immune cells toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fabs (instead of from an antibody, e.g., obtained from Fab libraries), in various embodiments, this scFv is fused to a transmembrane domain and then to an intracellular signaling domain. "First-generation" CARs include those that solely provide CD3zeta signals upon antigen binding, "Second-generation" CARs include those that provide both costimulation (e.g. CD28 or CD 137) and activation (CD3Q. "Third-generation" CARs include those that provide multiple costimulation (e.g. CD28 and CD 137) and activation (CO3Q). In various embodiments, the CAR is selected to have high affinity or avidity for the antigen. Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. See, e.g., Freshney, CULTURE ANIMAL CELLS: MANUAL BASIC TECH. (3rd ed., 1994). As used herein, the term "cancer" refers to an uncontrolled growth of cells that interferes with the normal functioning of the bodily organs and systems. A subject who has a cancer or a tumor is a subject having objectively measurable cancer cells present in the subject's body. Included in this definition are benign and malignant cancers, as well as dormant tumors or micrometastases. Cancers that migrate from their original location and seed vital organs can eventually lead to the death of the subject through the functional deterioration of the affected organs.

In one aspect, described herein is an isolated antibody, antigen-binding portion thereof, or chimaeric antigen receptor (CAR) that specifically binds to an antigen on the surface of a cancer cell, the antibody, antigen-binding portion thereof, or CAR comprising one or more heavy and light chain complimentarity determining regions (CDRs) selected from the group consisting of:
  a. a light chain CDR1 having the amino acid sequence of SEQ ID NO: 4 or 10;
  b. a light chain CDR2 having the amino acid sequence of SEQ ID NO: 5 or 11;
  c. a light chain CDR3 having the amino acid sequence of SEQ ID NO: 6 or 12;
  d. a heavy chain CDR1 having the amino acid sequence of SEQ ID NO: 1 or 7;
  e. a heavy chain CDR2 having the amino acid sequence of SEQ ID NO: 2 or 8; and
  f. a heavy chain CDR3 having the amino acid sequence of SEQ ID NO: 3 or 9.

In some embodiments, the isolated antibody, antigen-binding portion thereof, or CAR comprises the light chain complimentarity determining regions (CDRs):
  a. a light chain CDR1 having the amino acid sequence of SEQ ID NO: 4;
  b. a light chain CDR2 having the amino acid sequence of SEQ ID NO: 5; and
  c. a light chain CDR3 having the amino acid sequence of SEQ ID NO: 6.

In some embodiments, the isolated antibody, antigen-binding portion thereof, or CAR comprises the light chain complimentarity determining regions (CDRs):
  a. a light chain CDR1 having the amino acid sequence of SEQ ID NO: 10;
  b. a light chain CDR2 having the amino acid sequence of SEQ ID NO: 11; and
  c. a light chain CDR3 having the amino acid sequence of SEQ ID NO: 12.

In some embodiments, the isolated antibody, antigen-binding portion thereof, or CAR comprises the heavy chain complimentarity determining regions (CDRs):
a. a heavy chain CDR1 having the amino acid sequence of SEQ ID NO: 1;
b. a heavy chain CDR2 having the amino acid sequence of SEQ ID NO: 2; and
c. a heavy chain CDR3 having the amino acid sequence of SEQ ID NO: 3.

In some embodiments, the isolated antibody, antigen-binding portion thereof, or CAR comprises the heavy chain complimentarity determining regions (CDRs):
a. a heavy chain CDR1 having the amino acid sequence of SEQ ID NO: 7;
b. a heavy chain CDR2 having the amino acid sequence of SEQ ID NO: 8; and
c. a heavy chain CDR3 having the amino acid sequence of SEQ ID NO: 9.

In some embodiments, the isolated antibody, antigen-binding portion thereof, or CAR comprises the complimentarity determining regions (CDRs):
a. a light chain CDR1 having the amino acid sequence of SEQ ID NO: 4;
b. a light chain CDR2 having the amino acid sequence of SEQ ID NO: 5;
c. a light chain CDR3 having the amino acid sequence of SEQ ID NO: 6;
d. a heavy chain CDR1 having the amino acid sequence of SEQ ID NO: 1;
e. a heavy chain CDR2 having the amino acid sequence of SEQ ID NO: 2; and
f. a heavy chain CDR3 having the amino acid sequence of SEQ ID NO: 3.

In some embodiments, the isolated antibody, antigen-binding portion thereof, or CAR comprises the complimentarity determining regions (CDRs):
a. a light chain CDR1 having the amino acid sequence of SEQ ID NO: 10;
b. a light chain CDR2 having the amino acid sequence of SEQ ID NO: 11;
c. a light chain CDR3 having the amino acid sequence of SEQ ID NO: 12;
d. a heavy chain CDR1 having the amino acid sequence of SEQ ID NO: 7;
e. a heavy chain CDR2 having the amino acid sequence of SEQ ID NO: 8; and
f. a heavy chain CDR3 having the amino acid sequence of SEQ ID NO: 9.

In some embodiments, the isolated antibody, antigen-binding portion thereof, or CAR comprises a heavy chain having a sequence selected from SEQ ID NOs: 13-17 and 21-25. In some embodiments, the isolated antibody, antigen-binding portion thereof, or CAR comprises a light chain having a sequence selected from SEQ ID NOs: 18-20 and 26-28. In some embodiments, the isolated antibody, antigen-binding portion thereof, or CAR comprises a heavy chain having a sequence selected from SEQ ID NOs: 13-17 and a light chain having a sequence selected from SEQ ID NOs: 18-20. In some embodiments, the isolated antibody, antigen-binding portion thereof, or CAR comprises a heavy chain having a sequence selected from SEQ ID NOs: 21-25 and a light chain having a sequence selected from SEQ ID NOs: 26-28. In some embodiments, the isolated antibody, antigen-binding portion thereof, or CAR comprises a conservative substitution in a sequence not comprised by a CDR.

In some embodiments, the isolated antibody, antigen-binding portion thereof, or CAR specifically binds to an antigen on the surface of a cancer cell. In some embodiments, the isolated antibody, antigen-binding portion thereof, or CAR specifically binds to an antigen on the surface of a cancer cell, e.g. as compared to binding to normal cells. In some embodiments, the isolated antibody, antigen-binding portion thereof, or CAR specifically binds to an antigen on the surface of a cancer stem cell. In some embodiments, the isolated antibody, antigen-binding portion thereof, or CAR specifically binds to an antigen on the surface of a cancer stem cell and does not bind specifically to normal intestinal cells.

In some embodiments, the isolated antibody, antigen-binding portion thereof, or CAR is selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

In some embodiments, described herein is a Bi-specific T cell Engager (BiTE™) comprising an antigen-binding portion of an antibody as described herein. A BiTE is a construction of a moab with 2 distinct binding sites (e.g., 2 arms=2 distinct binding sites). Usually one site (e.g., arm) is directed against a tumor antigen and other site (e.g., arm) is directed against CD3 antigen. Thus, a BiTE can be conceived of as a chimera of 2 monoclonal antibodies where each is contributing an arm or a binding site. When the BiTE binds it is bridging between tumor cells and T cells. BiTE molecules can comprise at least two scFv domains, each of which has a different epitope specificity. BiTEs engage 1) any T cell, and 2) a specific antigen-expressing tumor cell to redirect tumor cell killing. In some embodiments, the scFv domain that engages, e.g., binds to any T cell can be an anti-CD3 scFv. A non-limiting example of a BiTE is blinatumomab. BiTEs are further described in the art, e.g. in Oberst et al. mAbs 2014 6:1571-1584; Zimmerman et al. International Immunology 2014 27:31-37; and Wickramasinghe Discov Med 2013 16:149-152; each of which is incorporated by reference herein in its entirety.

In some embodiments, the antibody, antigen-binding fragment thereof, and/or CAR is an isolated polypeptide. In some embodiments, the antibody, antigen-binding fragment thereof, and/or CAR is a purified polypeptide. In some embodiments, the antibody, antigen-binding fragment thereof, and/or CAR is an engineered polypeptide.

Figure 1:
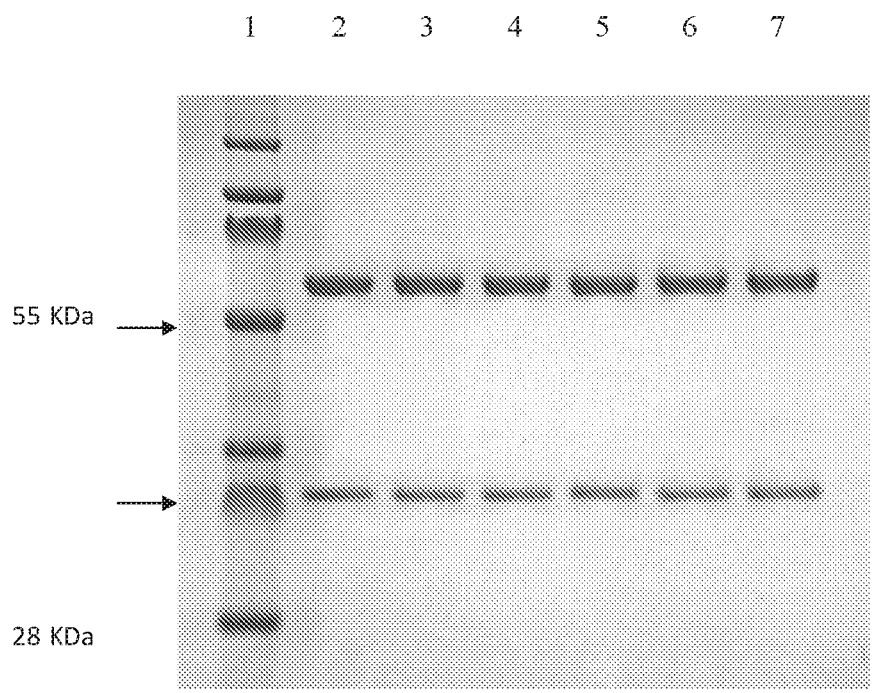
FIG. 1 depicts Coomassie blue stained SDS-PAGE gels of protein-A purified PTA-2357 humanized variant antibodies. Samples were loaded on a NuPage 4-12% Bis-Tris gel (Invitrogen Cat. No. NP0322BOX) and run at 200 V for 30 min Gels were prepared and run as recommended by the manufacturer. Lanes as indicated below: Lane 1: PageRuler Plus Prestained Protein Ladder (Fermentas; Waltham, Mass.; #SM1811) Lane 2: 1.0 µg PTA-2357 chimeric IgG1 antibody Lane 3: 1.0 µg PTA-2357 VH1/VK2 IgG1 antibody Lane 4: 1.0 µg PTA-2357 VH2/VK2 IgG1 antibody Lane 5: 1.0 µg PTA-2357 VH2/VK3 IgG1 antibody Lane 6: 1.0 µg PTA-2357 VH3/VK2 IgG1 antibody Lane 7: 1.0 µg PTA-2357 VH4/VK2 IgG1 antibody.
Figure 2:
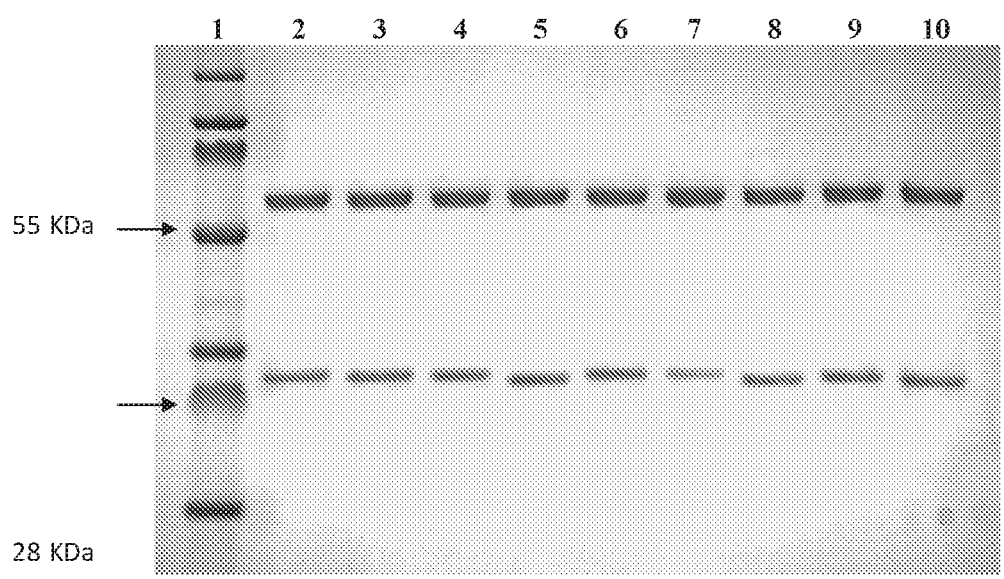
FIG. 2 depicts Coomassie blue stained SDS-PAGE gels of protein-A purified PTA-2358 humanized variant antibodies. Samples were loaded on a NuPage 4-12% Bis-Tris gel (Invitrogen; Grand Island, N.Y.; Cat. No. NP0322BOX) and run at 200 V for 30 min. Gels were prepared and run as recommended by the manufacturer. Lanes as indicated below: Lane 1: PageRuler Plus Prestained Protein Ladder (Fermentas #SM1811) Lane 2: 1.0 µg PTA-2358 chimeric IgG1 antibody Lane 3: 1.0 µg PTA-2358 VH1/VK1 IgG1 antibody Lane 4: 1.0 µg PTA-2358 VH2/VK1 IgG1 antibody Lane 5: 1.0 µg PTA-2358 VH2/VK2 IgG1 antibody Lane 6.

In embodiments wherein an antibody, antigen-binding fragment thereof, or CAR as described herein comprises at least one CDR which is not identical to the sequence of SEQ ID NOs: 1-12, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding fragment thereof as described herein, will result in an antigen or antigen-binding fragment thereof which will bind a cancer cell surface antigen. In some embodiments, the antibody or antigen-binding fragment thereof can bind specifically to a cancer cell. The method described in Fujii et al. also permits one of ordinary skill in the art to screen for a light chain sequence that will give the desired binding behavior when combined with a known heavy chain fragment and vice versa.

In some embodiments, an antibody, antigen-binding portion thereof, and/or CAR as described herein can be comprised by an antibody-drug conjugate. The drug can be, e.g., a chemotherapeutic molecule as described elsewhere herein. In some embodiments, an antibody and/or the antigen-binding portion thereof and the chemotherapeutic agent can be directly conjugated and/or bound to each other, e.g. an antibody-drug conjugate. In some embodiments, binding can be non-covalent, e.g., by hydrogen bonding, electrostatic, or van der Waals interactions; however, binding may also be covalent. By "conjugated" is meant the covalent linkage of at least two molecules.

Linkers for use in antibody-drug conjugates, and methods of making antibody-drug conjugates are known in the art and can be adapted to the compositions described herein. Exemplary antibody-drug conjugates can include, but are not limited to mertansine conjugates (e.g. bivatuzumab mertansine; cantuzumab mertansine; and lorvotuzumab mertansine) in which the antibody and mertansine are linked via 4-mercaptovaleric acid and momomethyl auristatin E (MMAE) conjugates (e.g., brentuximab MMAE and glembatumumab MMAE) in which the antibody and MMAE are linked by a cathepsin-cleavable linker comprising valine and citrulline, a paraaminobenzoic acid spacer, and a maleimide and caproic acid attachment group. Further discussion of antibody-drug conjugates, including suitable linker technologies can be found, e.g., in "Antibody-Drug Conjugates and Immunotoxins" Ed. Phillips, Gail Lewis. Humana Press; 2013; Zolot et al. Nature Reviews Drug Discovery 2013 12:259-260; and Ducry and Stump. Bioconjugate Chem 2010 21:5-13; each of which is incorporated by reference herein in its entirety.

In some embodiments, the technology described herein relates to a nucleic acid encoding an antibody, antigen-binding portion thereof, or CAR as described herein. In some embodiments, the nucleic acid comprises a sequence selected from SEQ ID NOs: 29-44. In some embodiments, the nucleic acid is a cDNA.

As used herein, the term "nucleic acid" or "nucleic acid sequence" refers to a polymeric molecule incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. In some embodiments, the nucleic acid can be a cDNA, e.g., a nucleic acid lacking introns.

In some embodiments, a nucleic acid encoding an antibody, antigen-binding portion thereof, or CAR as described herein is comprised by a vector. In some of the aspects described herein, a nucleic acid sequence encoding an antibody, antigen-binding portion thereof, or CAR as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence that is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody, antigen-binding portion thereof, or CAR as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In one aspect, described herein is a cell comprising an isolated antibody, antigen-binding portion thereof, or CAR as described herein. In some embodiments, the isolated antibody, antigen-binding portion thereof, or CAR as described herein is expressed on the cell surface. In some embodiments, the cell comprises a nucleic acid encoding an isolated antibody, antigen-binding portion thereof, or CAR as described herein.

In some embodiments, the cell is an immune cell. As used herein, "immune cell" refers to a cell that plays a role in the immune response Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the cell is a T cell; an NK cell; an NKT cell; a lymphocyte, such as a B cell or a T cells; in some embodiments the cell is a myeloid cell, such as a monocyte, macrophage, eosinophil, mast cell, basophil, or granulocyte.

Aspects of the technology described herein relate to compositions comprising an antibody, antigen-binding portion thereof, or CAR as described herein or a nucleic acid encoding an antibody, antigen-binding portion thereof, or CAR as described herein or a cell as described herein. In some embodiments, the composition is a pharmaceutical composition. As used herein, the term "pharmaceutical composition" refers to the active agent in combination with a pharmaceutically acceptable carrier accepted for use in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients that are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, the composition comprising an antibody, antigen-binding portion thereof, or CAR as described herein or a nucleic acid encoding an antibody, antigen-binding portion thereof, or CAR as described herein can be a lyophilisate.

In some embodiments, the technology described herein relates to a syringe comprising a therapeutically effective amount of a composition described herein. In some embodiments, the technology described herein relates to a container, e.g. a bag and/or sterile container comprising a therapeutically effective amount of a composition described herein.

As used herein, the phrase "therapeutically effective amount", "effective amount" or "effective dose" refers to an amount that provides a therapeutic or aesthetic benefit in the treatment, prevention, or management of a tumor or malignancy, e.g. an amount that provides a statistically significant decrease in at least one symptom, sign, or marker of a tumor or malignancy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents In one aspect, the technology described herein relates to a method comprising administering an antibody, antigen-binding portion thereof, or CAR as described herein or a nucleic acid encoding an antibody, antigen-binding portion thereof, or CAR as described herein to a subject. In some embodiments, the subject is in need of treatment for a cancer and/or malignancy. In some embodiments, the subject is in need of treatment for pancreatic cancer; lung cancer; non-small cell lung cancer; colon cancer; breast cancer; liver cancer; and prostate cancer.

In some embodiments, the method is a method of treating a subject. In some embodiments, the method is a method of treating a cancer in a subject.

In one aspect, described herein is a method of treating cancer in a subject in need thereof, the method comprising administering a cell as described herein, e.g. a cell comprising an antibody, antigen-binding portion thereof, or CAR as described herein. In some embodiments, the cell is an immune cell.

In one aspect, described herein is a method of treating cancer in a subject in need thereof, the method comprising administering a nucleic acid as described herein (e.g. one encoding an antibody, antigen-binding portion thereof, or CAR) to the subject, wherein the subject's immune cells are caused to express the polypeptide encoded by the nucleic acid. In some embodiments, the immune cell is a T cell. Nucleic acids can be targeted to particular cell types by, e.g., use of a cell-type specific promoter and/or a composition that selectively binds to the desired cell type. For example, conjugation of a nucleic acid to an aptamer can permit targeted delivery (McNamara, J O., et al (2006) Nat. Biotechnol. 24:1005-1015). In an alternative embodiment, the nucleic acid can be delivered using drug delivery systems such as a nanoparticle, a dendrimer, a polymer, liposomes, or a cationic delivery system. Positively charged cationic delivery systems facilitate binding of a nucleic acid molecule (negatively charged) and also enhance interactions at the negatively charged cell membrane to permit efficient uptake of a nucleic acid by the cell. Cationic lipids, dendrimers, or polymers can either be bound to a nucleic acid, or induced to form a vesicle or micelle (see e.g., Kim S H., et al (2008) Journal of Controlled Release 129(2):107-116) that encases a nucleic acid. The formation of vesicles or micelles further prevents degradation of the nucleic acid when administered systemically. Methods for making and administering cationic-inhibitory nucleic acid complexes are well within the abilities of one skilled in the art (see e.g., Sorensen, D R., et al (2003) J. Mol. Biol 327:761-766; Verma, U N., et al (2003) Clin. Cancer Res. 9:1291-1300; Arnold, A S et al (2007) J. Hypertens. 25:197-205, which are incorporated herein by reference in their entirety). Some non-limiting examples of drug delivery systems useful for systemic delivery of nucleic acids include DOTAP (Sorensen, D R., et al (2003), supra; Verma, U N., et al (2003), supra), Oligofectamine, "solid nucleic acid lipid particles"

(Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, a nucleic acid forms a complex with cyclodextrin for systemic administration. Methods for administration and pharmaceutical compositions of nucleic acids and cyclodextrins can be found in U.S. Pat. No. 7,427,605, which is herein incorporated by reference in its entirety. Targeted delivery of nucleic acids is described, for example in Ikeda and Taira Pharmaceutical Res 2006 23:1631-1640; Soutschek et al., Nature 2004 432:173-8 and Lorenze et al. Bioorg. Med. Chem. Lett. 14, 4975-4977 (2004); each of which is incorporated by reference herein in its entirety. By way of example, the nucleic acid can be targeted to immune cells by encapsulating the inhibitor in a liposome comprising ligands of receptors expressed on immune cells, e.g. TCRs. In some embodiments, the liposome can comprise aptamers specific for immune cells.

A "tumor" as used herein refers to an uncontrolled growth of cells tumor interferes with the normal functioning of the bodily organs and systems. The terms "cancer" and "malignancy" refer to a tumor that is metastatic, i.e. that is it has become invasive, seeding tumor growth in tissues remote from the original tumor site. A subject that has a cancer or a tumor is a subject having objectively measurable cancer cells present in the subject's body. Included in this definition are benign tumors and malignant cancers, as well as potentially dormant tumors or micrometastatses. Cancers that migrate from their original location and seed other vital organs can eventually lead to the death of the subject through the functional deterioration of the affected organs. Hematopoietic cancers, such as leukemia, are able to outcompete the normal hematopoietic compartments in a subject, thereby leading to hematopoietic failure (in the form of anemia, thrombocytopenia and neutropenia) ultimately causing death.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, the methods described herein relate to CAR-immune cell therapies such as CAR-T therapy. CAR-T and related therapies relate to adoptive cell transfer of immune cells (e.g. T cells) expressing a CAR that binds specifically to a targeted cell type (e.g. cancer cells) to treat a subject. In some embodiments, the cells administered as part of the therapy can be autologous to the subject. In some embodiments, the cells administered as part of the therapy are not autologous to the subject. In some embodiments, the cells are engineered and/or genetically modified to express the CAR. Further discussion of CAR-T therapies can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

As used herein, a "subject" means a human or animal. Usually the animal is a vertebrate such as a primate, rodent, domestic animal or game animal Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, various cancers. In addition, the methods described herein can be used to treat domesticated animals and/or pets. A subject can be male or female.

A subject can be one who has been previously diagnosed with or identified as suffering from or having a condition in need of treatment (e.g. a cancer) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. A "subject in need" of treatment for a particular condition can be a subject having that condition, diagnosed as having that condition, or at risk of developing that condition.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment. As used herein, the term "administering," refers to the placement of an antibody, antigen-binding portion thereof, or CAR as described herein or a nucleic acid encoding an antibody, antigen-binding portion thereof, or CAR, or a cell comprising such a reagent, as described herein into a subject by a method or route which results in at least partial localization of the agents at a desired site. The pharmaceutical composition comprising an antibody, antigen-binding portion thereof, or CAR as described herein or a nucleic acid encoding an antibody, antigen-binding portion thereof, or CAR, or a cell comprising such a reagent as described herein disclosed herein can be administered by any appropriate route which results in an effective treatment in the subject.

The dosage ranges for the agent depend upon the potency, and encompass amounts large enough to produce the desired effect e.g., slowing of tumor growth or a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments, the dosage ranges from 0.001 mg/kg body weight to 0.5 mg/kg body weight. In some embodiments, the dose range is from 5 µg/kg body weight to 100 µg/kg body weight. Alternatively, the dose range can be titrated to maintain serum levels between 1 µg/mL and 1000 µg/mL. For systemic administration, subjects can be administered a therapeutic amount, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments (e.g., when an antibody-drug conjugate is administered), the dose can be from about 2 mg/kg to about 15 mg/kg. In some embodiments, the dose can be about 2 mg/kg. In some embodiments, the dose can be about 4 mg/kg. In some embodiments, the dose can be about 5 mg/kg. In some embodiments, the dose can be about 6 mg/kg. In some embodiments, the dose can be about 8 mg/kg. In some embodiments, the dose can be about 10 mg/kg. In some embodiments, the dose can be about 15 mg/kg.

In some embodiments (e.g. when an antibody or antigen-binding portion thereof is administered), the dose can be from about 100 mg/m$^2$ to about 700 mg/m$^2$. In some embodiments, the dose can be about 250 mg/m$^2$. In some embodiments, the dose can be about 375 mg/m$^2$. In some embodiments, the dose can be about 400 mg/m$^2$. In some embodiments, the dose can be about 500 mg/m$^2$.

In some embodiments (e.g. when a BiTE is administered), the dose can be from about 0.5 to about 90 ug/m$^2$ per day. In some embodiments (e.g. when a BiTE is administered), the dose can be from about 5 to about 60 ug/m$^2$ per day. In some embodiments the dose can be about 5 ug/m$^2$ per day. In some embodiments the dose can be about 15 ug/m$^2$ per day. In some embodiments the dose can be about 60 ug/m$^2$ per day.

In some embodiments (e.g. when a cell as described herein is administered), the dosage can be from about $1\times10^5$ cells to about $1\times10^8$ cells per kg of body weight. In some embodiments, the dosage can be from about $1\times10^6$ cells to about $1\times10^7$ cells per kg of body weight. In some embodiments, the dosage can be about $1\times10^6$ cells per kg of body weight. In some embodiments, one dose of cells can be administered. In some embodiments, the dose of cells can be repeated, e.g., once, twice, or more. In some embodiments, the dose of cells can be administered on, e.g., a daily, weekly, or monthly basis.

Administration of the doses recited above can be repeated. In some embodiments, the doses are given once a day, or multiple times a day, for example but not limited to three times a day. In some embodiments, the doses recited above are administered daily for several weeks or months. The duration of treatment depends upon the subject's clinical progress and responsiveness to therapy.

In some embodiments, the dose can be administered intravenously. In some embodiments, the intravenous administration can be an infusion occurring over a period of from about 10 minutes to about 3 hours. In some embodiments, the intravenous administration can be an infusion occurring over a period of from about 30 minutes to about 90 minutes.

In some embodiments the dose can be administered about weekly. In some embodiments, the dose can be administered weekly. In some embodiments, the dose can be administered weekly for from about 12 weeks to about 18 weeks. In some embodiments the dose can be administered about every 2 weeks. In some embodiments the dose can be administered about every 3 weeks. In some embodiments, the dose can be from about 2 mg/kg to about 15 mg/kg administered about every 2 weeks. In some embodiments, the dose can be from about 2 mg/kg to about 15 mg/kg administered about every 3 weeks. In some embodiments, the dose can be from about 2 mg/kg to about 15 mg/kg administered intravenously about every 2 weeks. In some embodiments, the dose can be from about 2 mg/kg to about 15 mg/kg administered intravenously about every 3 weeks. In some embodiments, the dose can be from about 200 mg/m$^2$ to about 400 mg/m$^2$ administered intravenously about every week. In some embodiments, the dose can be from about 200 mg/m$^2$ to about 400 mg/m$^2$ administered intravenously about every 2 weeks. In some embodiments, the dose can be from about 200 mg/m$^2$ to about 400 mg/m$^2$ administered intravenously about every 3 weeks. In some embodiments, a total of from about 2 to about 10 doses are administered. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, the administration occurs for a total of from about 4 weeks to about 12 weeks. In some embodiments, the administration occurs for a total of about 6 weeks. In some embodiments, the administration occurs for a total of about 8 weeks. In some embodiments, the administration occurs for a total of about 12 weeks. In some embodiments, the initial dose can be from about 1.5 to about 2.5 fold greater than subsequent doses.

In some embodiments, the dose can be from about 1 mg to about 2000 mg. In some embodiments, the dose can be about 3 mg. In some embodiments, the dose can be about 10 mg. In some embodiments, the dose can be about 30 mg. In some embodiments, the dose can be about 1000 mg. In some embodiments, the dose can be about 2000 mg. In some embodiments, the dose can be about 3 mg given by intravenous infusion daily. In some embodiments, the dose can be about 10 mg given by intravenous infusion daily. In some embodiments, the dose can be about 30 mg given by intravenous infusion three times per week.

A therapeutically effective amount is an amount of an agent that is sufficient to produce a statistically significant, measurable change in tumor size, tumor growth etc. (efficacy measurements are described below herein). Such effective amounts can be gauged in clinical trials as well as animal studies.

An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having cancer. Local administration directly to a tumor mass is also specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In some embodiments, the methods further comprise administering the pharmaceutical composition described herein along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, gemcitabine, cisplastin, paclitaxel, carboplatin, bortezomib, AMG479, vorinostat, rituximab, temozolomide, rapamycin, ABT-737, PI-103 and checkpoint inhibitors including, but not limited to, ipilimumab, tremelimumab, Nivolumab, and pembrolizumab.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology $2^{nd}$ Edition, 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The bispecific and multispecific polypeptide agents described herein can be used in conjunction with additional chemotherapeutic agents.

In some embodiments of the methods described herein, the methods further comprise administering one or more chemotherapeutic agents to the subject being administered the pharmaceutical composition described herein. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

In some embodiments, the methods described herein can further comprise administering an additional immunotherapy to the subject. As used herein, "immunotherapy" refers to a diverse set of therapeutic strategies designed to induce the patient's own immune system to fight the tumor, and include, but are not limited to, intravesical BCG immunotherapy for superficial bladder cancer, vaccines to generate specific immune responses, such as for malignant melanoma and renal cell carcinoma, the use of Sipuleucel-T for prostate cancer, in which dendritic cells from the patient are loaded with prostatic acid phosphatase peptides to induce a specific immune response against prostate-derived cells, administration of cytokines, growth factors and/or signaling molecules that stimulate one or more immune cell type (e.g. interleukins), ex vivo expansion and/or stimulation of lymphocytes and/or dendritic cell specific for a tumor antigen prior to reintroduction to the patient, imiquimod, adoptive cell transfer, and/or the methods described, e.g., in International Patent Publication WO 2003/063792 and U.S. Pat. No. 8,329,660. In some embodiments, the immunotherapy stimulates NK responses. In some embodiments, the immunotherapy is an adoptive cell transfer approach.

The efficacy of a given treatment for cancer can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statistically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e g, a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more.

As used herein, "engineered" refers to the aspect of having been manipulated by the hand of man. For example, an antibody, antigen-binding portion thereof, or CAR is considered to be "engineered" when the sequence of the antibody, antigen-binding portion thereof, or CAR is manipulated by the hand of man to differ from the sequence of an antibody as it exists in nature. As is common practice and is understood by those in the art, progeny and copies of an engineered polynucleotide and/or polypeptide are typically still referred to as "engineered" even though the actual manipulation was performed on a prior entity.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof as described in Kabat et al. (1971) Ann. NY Acad, Sci. 190:382-391 and/or Kabat, E. A., et al. (1991) Sequences of Proteins of Immunological Interest, Fifth Edition, U.S. Department of Health and Human Services, NIH Publication No. 91-3242.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics.

"Avidity" is the measure of the strength of binding between an antigen-binding molecule (such as an antibody or antibody fragment thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant (KA) of $10^5$ to $10^{12}$ liter/moles or more, such as $10^7$ to $10^{12}$ liter/moles or $10^8$ to $10^{12}$ liter/moles). Any KD value greater than $10^{-4}$ mol/liter (or any KA value lower than $10^4$ $M^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of a peptide (e.g., an antibody, CAR or portion thereof) described herein to bind to a target, such as an antigen present on the cell-surface of a cancer cell, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody, antigen-binding portion thereof, or CAR is said to specifically bind an antigen when it preferentially recognizes its target antigen in a complex mixture of proteins and/or macromolecules.

In some embodiments, a reagent that binds specifically to cancer cells binds specifically to cancer cells as compared to non-cancerous cells. In some embodiments, a reagent that binds specifically to cancer cells binds specifically to cancer cells as compared to non-cancerous cells of the same cell type.

In some embodiments, an antibody, antigen-binding portion thereof, and/or CAR as described herein binds to a cancer cell with a dissociation constant (KD) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an antibody, antigen-binding portion thereof, and/or CAR as described herein binds to a cancer cell with a dissociation constant (KD) of from about $10^{-5}$ M to $10^{-6}$ M. In some embodiments, an antibody, antigen-binding portion thereof, and/or CAR as described herein binds to a cancer cell with a dissociation constant (KD) of from about $10^{-6}$ M to $10^{-7}$ M. In some embodiments, an antibody, antigen-binding portion thereof, and/or CAR as described herein binds to a cancer cell with a dissociation constant (KD) of from about $10^{-7}$ M to $10^{-8}$ M. In some embodiments, an antibody, antigen-binding portion thereof, and/or CAR as described herein binds to a cancer cell with a dissociation constant (KD) of from about $10^{-8}$ M to $10^{-9}$ M. In some embodiments, an antibody, antigen-binding portion thereof, and/or CAR as described herein binds to a cancer cell with a dissociation constant (KD) of from about $10^{-9}$ M to $10^{-10}$ M. In some embodiments, an antibody, antigen-binding portion thereof, and/or CAR as described herein binds to a cancer cell with a dissociation constant (KD) of from about $10^{-10}$ M to $10^{-11}$ M. In some embodiments, an antibody, antigen-binding portion thereof, and/or CAR as described herein binds to a cancer cell with a dissociation constant (KD) of from about $10^{-11}$ M to $10^{-12}$ M. In some embodiments, an antibody, antigen-binding portion thereof, and/or CAR as described herein binds to a cancer cell with a dissociation constant (KD) of less than $10^{-12}$ M.

As used herein, the term "antibody" refers to immunoglobulin molecules and immunologically active portions of immunoglobulin molecules, i.e., molecules that contain an antigen-binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference).

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Other boundaries defining CDRs overlapping with the Kabat CDRs have been described by Padlan (FASEB J. 9:133-139 (1995)) and MacCallum (J Mol Biol 262(5):732-45 (1996)) and Chothia (J. Mol. Biol. 196:901-917 (1987) and Nature 342:877-883 (1989)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat defined CDRs.

The terms "antigen-binding fragment" or "antigen-binding portion" of an antibody, used interchangeably herein, refer to one or more fragments of an antibody as described herein, said fragments still having the binding affinities as defined above herein. Fragments of a complete antibody have been shown to be able to carry out the antigen-binding function of an antibody. In accordance with the term "antigen-binding portion" of an antibody, examples of binding fragments include (i) an Fab fragment, i.e. a monovalent fragment composed of the VL, VH, CL and CH1 domains; (ii) an F(ab')2 fragment, i.e. a bivalent fragment comprising two Fab fragments linked to one another in the hinge region via a disulfide bridge; (iii) an Fd fragment composed of the VH and CH1 domains; (iv) an Fv fragment composed of the FL and VH domains of a single arm of an antibody; and (v) a dAb fragment (Ward et al., (1989) Nature 341:544-546) consisting of a VH domain or of VH, CH1, CH2, DH3, or VH, CH2, CH3 (dAbs), or single domain antibodies, comprising only VL domains have also been shown to specifically bind to target eptiopes). Although the two domains of the Fv fragment, namely VL and VH, are encoded by separate genes, they may further be linked to one another using a synthetic linker, e.g. a poly-G4S amino acid sequence ('G4S' disclosed as SEQ ID NO: 46), and recombinant methods, making it possible to prepare them as a single protein chain in which the VL and VH regions combine in order to form monovalent molecules (known as single chain Fv (ScFv); see, for example, Bird et al. (1988) Science 242:423-426; and Huston et al. (1988) Proc. Natl. Acad. Sci. USA 85:5879-5883). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites (see, for example, Holliger, R, et al. (1993) Proc. Natl. Acad. Sci. USA 90:6444-6448; Poljak, R. J, et al. (1994) Structure 2:1121-1123). An immunoglobulin constant domain refers to a heavy or light chain constant domain. Human IgG heavy chain and light chain constant domain amino acid sequences are known in the art.

Furthermore, an antibody, antigen-binding portion thereof, or CAR as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule (Kipriyanov, S. M., et al. (1995) Human Antibodies and Hybridomas 6:93-101) and the use of a cystein residue, a marker peptide and a C-terminal polyhistidinyl, e.g. hexahistidinyl tag ('hexahistidinyl tag' disclosed as SEQ ID NO: 45) in order to produce bivalent and biotinylated scFv molecules (Kipriyanov, S. M., et al. (1994) Mol. Immunol. 31:10471058).

In some embodiments, the antibody, antigen-binding portion thereof, or CAR described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding fragment thereof.

As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g. an epitope present on a cancer cell). Such conservatively modified variants are in addition to and do not exclude polymorphic variants, interspecies homologs, and alleles consistent with the disclosure.

In some embodiments, a conservatively modified variant of an antibody reagent can comprise alterations other than in the CDRs, e.g. a conservatively modified variant of an antibody reagent can comprise CDRs having the sequence of one or more of SEQ ID NOs 1-12.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar:

Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Particular conservative substitutions include, for example; Ala into Gly or into Ser; Arg into Lys; Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the antibody, antigen-binding portion thereof, and/or CAR as described herein can be a variant of a sequence described herein, e.g. a conservative substitution variant of an antibody polypeptide. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity, e.g. antigen-specific binding activity for the relevant target polypeptide, e.g. a cancer cell surface epitope. A wide variety of PCR-based site-specific mutagenesis approaches are also known in the art and can be applied by the ordinarily skilled artisan.

Examples of substitution variants include conservative substitution of amino acids, e.g. in a $V_H$ or $V_L$ domain, that do not alter the sequence of a CDR. A conservative substitution in a sequence not comprised by a CDR can be a substitution relative to a wild-type or naturally-occurring sequence, e.g. human or murine framework and/or constant regions of an antibody sequence.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

The antibodies disclosed herein can include any one of the $V_H$ or $V_L$ regions disclosed herein, for example, any one of SEQ ID NOs. 1-28. Also contemplated are antibodies wherein $V_H$ or $V_L$ regions comprise an amino acid sequence at least 80%, at least 85%, at least 90%, at least 91%, at least 92%, at least 93%, at least 94%, at least 95%, at least 96%, at least 97%, at least 98%, at least 99%, or more, identical to any one of SEQ ID NOs. 1-28.

In some embodiments, the antibody or antigen-binding portion thereof is a fully human antibody. In some embodiments, the antibody, antigen-binding portion thereof, or CAR is a humanized antibody or antibody reagent. In some embodiments, the antibody or antigen-binding portion thereof, or CAR is a chimeric antibody or antibody reagent. In some embodiments, the antibody, antigen-binding portion thereof, or CAR is a recombinant polypeptide.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g. a mouse-antibody, (referred to as the donor immunoglobulin). See, Queen et al., Proc Natl Acad Sci USA 86:10029-10033 (1989) and WO 90/07861, U.S. Pat. Nos. 5,693,762, 5,693,761, 5,585,089, 5,530,101 and Winter, U.S. Pat. No. 5,225,539, which are herein incorporated by reference in their entirety. The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies. See Carter et al., WO 92/22653, which is herein incorporated by reference in its entirety.

As used herein, the term "humanized antibody" refers to an antibody (or antigen-binding portion thereof) comprising a human framework, at least one complementarity determining regions (CDR) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences.

In some embodiments, the antibody reagents (e.g. antibodies or CARs) described herein are not naturally-occurring biomolecules. For example, a murine antibody raised against an antigen of human origin would not occur in nature absent human intervention and manipulation, e.g. manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

Nucleic acid molecules encoding amino acid sequence variants of antibodies are prepared by a variety of methods known in the art. These methods include, but are not limited to preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, N Y, 1982 and 1989), and Ausubel, 1987, 1993, and can be used to construct nucleic acid sequences which encode a monoclonal antibody molecule, antigen binding region thereof, or CAR.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of an antibody, antigen-binding portion thereof, or CAR as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression may be avoided. Sabin et al., 7 Bio/Technol. 705 (1989); Miller et al., 7 Bio/Technol. 698 (1989). Any of a series of yeast gene expression systems incorporating promoter and termination elements from the actively expressed genes coding for glycolytic enzymes produced in large quantities when yeast are grown in mediums rich in glucose can be utilized to obtain recombinant antibodies, antigen-binding portions thereof, or CARs thereof as described herein. Known glycolytic genes can also provide very efficient transcriptional control signals. For example, the promoter and terminator signals of the phosphoglycerate kinase gene can be utilized.

Production of antibodies, antigen-binding portions thereof, or CARs as described herein in insects can be achieved. For example, by infecting the insect host with a baculovirus engineered to express a transmembrane polypeptide by methods known to those of ordinary skill in the art. See Ausubel et al., 1987, 1993.

In some embodiments, the introduced nucleotide sequence is incorporated into a plasmid or viral vector capable of autonomous replication in the recipient host. Any of a wide variety of vectors can be employed for this purpose and are known and available to those of ordinary skill in the art. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli.*, for example. Other gene expression elements useful for the expression of cDNA encoding antibodies, antigen-binding portions thereof, or CARs include, but are not limited to (as) viral transcription promoters and their enhancer elements, such as the SV40 early promoter. (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983) Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene can be assembled in, or inserted into, an expression vector. Alternatively, mRNA or DNA can be used without the use of an expression vector ("naked mRNA" or "naked DNA"). Recipient cells capable of expressing the chimeric immunoglobulin chain gene product are then transfected singly with an antibody, antigen-binding portion thereof, or CAR, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the fused genes encoding the antibody, antigen-binding fragment thereof, CAR, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively, the fused genes encoding chimeric H and L chains can be assembled on the same expression vector.

For transfection of the expression vectors, naked mRNA or naked DNA and production of the chimeric, humanized, or composite human antibodies described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or inter-species heterohybridoma cells.

An expression vector or naked mRNA or naked DNA carrying a chimeric, humanized, or composite human antibody construct, antibody, antigen-binding portion thereof, and/or CAR as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector that incorporates a said DNA sequence; and a host transformed with a said expression vector.

Usually the CDR regions in humanized antibodies and human antibody variants are substantially identical, and more usually, identical to the corresponding CDR regions in the mouse or human antibody from which they were derived. Although not usually desirable, it is sometimes possible to make one or more conservative amino acid substitutions of CDR residues without appreciably affecting the binding affinity of the resulting humanized immunoglobulin or human antibody variant. Occasionally, substitutions of CDR regions can enhance binding affinity.

In addition, techniques developed for the production of "chimeric antibodies" (see Morrison et al., Proc. Natl. Acad. Sci. 81:851-855 (1984); Neuberger et al., Nature 312:604-608 (1984); Takeda et al., Nature 314:452-454 (1985); which are incorporated by reference herein in their entireties) by splicing genes from a mouse, or other species, antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies.

The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody, antigen-binding portion thereof, or CAR as described herein. Such functional activities include binding to cancer cells and/or anti-cancer activity. Additionally, a polypeptide having functional activity means the polypeptide exhibits activity similar, but not necessarily identical to, an activity of a reference antibody, antigen-binding portion thereof, or CAR as described herein, including mature forms, as measured in a particular assay, such as, for example, a biological assay, with or without dose dependency. In the case where dose dependency does exist, it need not be identical to that of the reference antibody, antigen-binding portion thereof, or CAR, but rather substantially similar to the dose-dependence in a given activity as compared to the reference antibody, antigen-binding portion thereof, or CAR as described herein (i.e., the candidate polypeptide will exhibit greater activity, or not more than about 25-fold less, about 10-fold less, or about 3-fold less activity relative to the antibodies, antigen-binding fragments, and/or CARs described herein).

The materials and methods disclosed herein are generally and variously useful for detecting CEACAM6 in a biological sample from a patient. In some embodiments, the detecting step can include contacting the biological sample from the patient with a first antibody that specifically binds to a first epitope comprising a glycopeptide to form a first complex between the first antibody and the CEACAM6 followed by contacting the first complex with a second antibody that specifically binds to a second epitope, wherein the first and second epitopes are different, to form a second complex, wherein the second complex comprises the first antibody, CEACAM6, and the second antibody, and then detecting the second complex, thereby detecting CEACAM6.

In some embodiments, the biological sample can be a blood, serum, plasma, urine, stool, sputum, or biopsy sample. In some embodiments, the first antibody can be immobilized on a solid support, for example, a solid matrix such as a polystyrene or polycarbonate microwell or dipstick, a membrane, or a glass support (e.g., a glass slide). In certain embodiments, the second antibody can contain a detectable reporter moiety or label such as an enzyme, dye, radionuclide, luminescent group, fluorescent group or biotin. The amount of the second antibody that remains bound to the complex can be determined using a method appropriate for the specific detectable reporter moiety or label. For radioactive groups, scintillation counting or autoradiographic methods are generally appropriate. Spectroscopic method can be used to detect dyes (including, for example, colorimetric products of enzyme reactions), luminescent groups and fluorescent groups. Biotin can be detected using avidin or streptavidin, coupled to a different reporter group (commonly a radioactive or fluorescent group or an enzyme). Enzyme reporter groups can generally be detected by the addition of substrate (generally for a specific period of time), followed by spectroscopic, spectrophotometric or other analysis of the reaction products. Standards and standard additions can be used to determine the level of antigen in a sample.

As used herein, the term "administering," refers to the placement of a compound as disclosed herein into a subject by a method or route that results in at least partial delivery of the agent at a desired site. Pharmaceutical compositions comprising the compounds disclosed herein can be administered by any appropriate route that results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

EXAMPLES

Example 1

Design of Humanized Antibody Variable Region Sequences

Structural models of the PTA-2357 and PTA-2358 V regions were produced using Swiss-PDB and analysed in order to identify important amino acids in the mouse V regions that were likely to be essential for the binding properties of the antibody. Residues contained within the CDRs (using both Kabat and Chothia definitions), together with a number of framework residues, were considered to be important. Both the VH and VK sequences of PTA-2357 and PTA-2358 contain typical framework residues (see FIGS. 4-19), especially in the VH where the antibody has very common sequence configurations at critical positions e.g. Kabat residues 45-49 (LEWIG (SEQ ID NO: 47) for both PTA-2357 and PTA-2358) and 90-94 (YYCAR (SEQ ID NO: 48) for PTA-2357 and YYCNA (SEQ ID NO: 49) for PTA-2358). The CDR motifs of PTA-2357 and PTA-2358 are comparable to many mouse antibodies.

For the humanization of PTA-2357, the human VH1-18*01 germline framework was selected as a template for the heavy chain, and the VK1-39*01 germline framework selected as a template for the light chain (both 62% identity to the mouse VH and VK). For the humanization of PTA-2358, the human VH1-f*01 germline framework was selected as a template for the heavy chain, and the VK7-3*01 germline framework selected as a template for the light chain (64% and 77% identity to the mouse VH and VK respectively). For both antibodies a number of mouse framework residues were identified as being important for the conformation of the CDRs, and varying numbers of these were included in the variants.

For the humanization of PTA-2357, five VH variants and three VK variants were designed; likewise, for PTA-2358, five VH and three VK variants were designed (see FIGS. 4-19).

Cloning and Expression of Humanized Variable Regions

All VH and VK region genes were synthesised using a series of overlapping oligonucleotides that were annealed, ligated and PCR amplified to give full length synthetic V regions. The assembled variants were then cloned directly into the expression vectors pANTVhG1 and pANTVk (Antitope) for IgG1 heavy chain and kappa light chain respectively.

For PTA-2357 and PTA-2358, all combinations of humanized heavy and light chains (i.e. a total of 15 pairings for each antibody) were stably transfected into NS0 cells via electroporation. For each combination, the electroporated cells were distributed into 5×96 well tissue culture plates and selected using 200 nM methotrexate (Sigma #M8407). Wells containing methotrexate resistant colonies for each construct were sampled and tested for IgG1 expression levels, and the best expressing lines were selected, expanded continuously to T175 flasks and frozen under liquid nitrogen. Cell lines were generated that expressed antibody for all 15 combinations.

In addition, to provide an initial assessment, CHO-K1 cells were transiently transfected with all combinations of humanized heavy and light chains for both PTA-2357 and PTA-2358 using Lipofectamine 2000 (Invitrogen #11668). 96 hours post transfection, cell media was harvested for antibody purification. Briefly, humanized antibody variants from stable and transient transfections were purified from cell culture supernatants on 1 ml Protein A sepharose columns (GE Healthcare #11-0034-93) and quantified by $OD_{280nm}$ using an extinction coefficient, $E_{c(0.1\%)}$ based on the predicted amino acid sequence. The $E_{c(0.1\%)}$ values for PTA-2357 and PTA-2358 are 1.40 and 1.44 respectively.

Binding of Variant Antibodies to NCI-H187 Classic Small Cell Lung Carcinoma Cells The binding of CHO-K1 transiently expressed humanized variants of PTA-2357 and PTA-2358 antibodies to NCI-H187 classic small cell lung carcinoma cells (ATCC Number: CRL-5804) was assessed by a competition assay and subsequent flow cytometry analysis. NCI-H187 cells were harvested, washed in cold PBS, resuspended in cell dissociation buffer (Gibco #13151-014) and then filtered through a 70 micron cell strainer (BD Biosciences #352350) to break down multicellular aggregates. Cells were diluted into cold FACS buffer (1% FBS/0.01% Sodium Azide/PBS) to $4 \times 10^6$ cells/ml and kept on ice.

Dilution series of each variant-2357 and variant-2358 antibody (8 μg/ml-0.296 μg/ml) were premixed with constant concentrations of the relevant mouse reference antibody (0.1 μg/ml PTA-2357 or 0.3 μg/ml PTA-2358) in V-bottomed 96 well plates (Corning #3894) at 50 μl/well. 50 μl of cell suspension was added to each well to give a final concentration range of 4 μg/ml-0.148 μg/ml in 0.05 μg/ml or 0.15 μg/ml mouse reference antibody. The plates were incubated at 4° C. for 1 hour. Cells were washed with FACS buffer, resuspended in 100 μl of secondary antibody (Sigma #F2772, goat anti-mouse IgG (Fc specific) FITC conjugated) and incubated for 1 hour at 4° C.

Cells were washed twice, resuspended in a final volume of 175 μl FACS buffer and transferred to FACS tubes. Fluorescence was measured by flow cytometry and data curves plotted as normalised % positive events (gated in R2). $IC_{50}$ values were determined for each antibody from the curves, and the relative $IC_{50}$ values calculated by dividing the test antibody result by the chimeric antibody result. (see Tables 1 and 2).

Lead humanized variants for PTA-2357 and PTA-2358 were selected (see Table 3) and retested in the competition flow cytometry assay (as described for the transient material), over an increased concentration range, using the material purified from the stably transfected NS0 cells (see FIGS. 3A-3C). FIG. 3(a) shows the binding curves for the PTA-2357 leads with the relative $IC_{50}$ values summarised in Table 4. All the selected leads bind within 1.5 fold of the chimeric antibody. FIGS. 3(b) and (c) shows the binding curves for the PTA-2358 leads with the relative $IC_{50}$ values again summarised in Table 4. All the selected leads bind within 3 fold of the chimeric antibody, with all but two binding within 1.5 fold.

Discussion

Described herein are humanized antibodies specific for NCI-H187 cells, constructed using CDR-grafting technology. Humanized antibodies were constructed using single human germline framework sequences as templates, incorporating the murine CDRs and some additional framework residues identified as being important for the correct conformation of the CDRs. Variants were designed to minimize the number of mouse residues incorporated into the human sequences. For both PTA-2357 and PTA-2358 fifteen candidate humanized antibodies were initially tested for binding to NCI-H187 cells. Table 4 depicts five variants of the PTA-2357 antibody and eight variants of the PTA-2358 antibody with particularly good performance in the assays described herein.

TABLE 1

Relative $IC_{50}$ values of PTA-2357 CHO-K1-derived humanized antibody variants compared to chimeric PTA-2357

| | | Heavy Chain Variants | | | | |
|---|---|---|---|---|---|---|
| | | VH1 | VH2 | VH3 | VH4 | VH5 |
| Light Chain Variants | VK1 | >3 | >3 | >3 | >3 | >3 |
| | VK2 | 1.2 | 1.36 | 1.57 | 1.5 | 2.43 |
| | VK3 | 2.0 | 0.82 | 1.64 | 2.06 | >3 |

TABLE 2

Relative $IC_{50}$ values of PTA-2358 CHO-K1-derived humanized antibody variants compared to chimeric PTA-2358

| | | Heavy Chain Variants | | | | |
|---|---|---|---|---|---|---|
| | | VH1 | VH2 | VH3 | VH4 | VH5 |
| Light Chain Variants | VK1 | 1.09 | 1.28 | 1.09 | 1.48 | 1.69 |
| | VK2 | 2.38 | 1.29 | 1.81 | 1.68 | 1.68 |
| | VK3 | 2.68 | >3 | 2.43 | >3 | >3 |

TABLE 3

PTA-2357 and PTA-2358 lead humanized variants selected based on the binding data obtained from material purified from transiently transfected CHO-K1 cells

| Lead Variants | |
|---|---|
| PTA-2357 | PTA-2358 |
| VH1/VK2 | VH1/VK1 |
| VH2/VK2 | VH2/VK1 |
| VH2/VK3 | VH2/VK2 |
| VH3/VK2 | VH3/VK1 |
| VH4/VK2 | VH4/VK1 |
| | VH4/VK2 |
| | VH5/VK1 |
| | VH5/VK2 |

TABLE 4

Relative $IC_{50}$ values of PTA-2357 and PTA-2358 NS0-derived humanized antibody variants compared to the relevant chimeric antibodies

| Lead Variants of PTA-2357 | | Lead Variants of PTA-2358 | |
|---|---|---|---|
| Variants | Relative IC50 | Variants | Relative IC50 |
| VH1/VK2 | 1.06 | VH1/VK1 | 1.11 |
| VH2/VK2 | 1.16 | VH2/VK1 | 1.03 |
| VH2/VK3 | 1.23 | VH2/VK2 | 1.03 |
| VH3/VK2 | 1.06 | VH3/VK1 | 1.12 |
| VH4/VK2 | 1.34 | VH4/VK1 | 2.65 |
| | | VH4/VK2 | 1.49 |
| | | VH5/VK1 | 1.65 |
| | | VH5/VK2 | 1.11 |

TABLE 5

CDRs

| Chain Identity | CDR Identity | Sequence | SEQ ID NO: |
|---|---|---|---|
| PTA-2357 Heavy Chain | CDR1 | DYTIH | 1 |
| | CDR2 | HISTYSGNTNNNQKFKG | 2 |
| | CDR3 | GDYYGSFYKFEY | 3 |
| PTA-2357 Light Chain | CDR1 | GASENIYGALN | 4 |
| | CDR2 | GATNLAD | 5 |
| | CDR3 | QNVLSIPYT | 6 |
| PTA-2358 Heavy Chain | CDR1 | DYYMH | 7 |
| | CDR2 | WIDPGNGDTECAPKFQG | 8 |
| | CDR3 | PYYSGSSHFDY | 9 |
| PTA-2358 Light Chain | CDR1 | RASKSVSASGYSFLH | 10 |
| | CDR2 | LASNLES | 11 |
| | CDR3 | QHSRELRT | 12 |

TABLE 6

| Chain Variant | SEQ ID NO: | Comprises CDRs having the sequence of SEQ ID NOs: |
|---|---|---|
| PTA-2357 VH Variant 1 | 13 | 1-3 |
| PTA-2357 VH Variant 2 | 14 | 1-3 |
| PTA-2357 VH Variant 3 | 15 | 1-3 |
| PTA-2357 VH Variant 4 | 16 | 1-3 |
| PTA-2357 VH Variant 5 | 17 | 1-3 |
| PTA-2357 VK Variant 1 | 18 | 4-6 |
| PTA-2357 VK Variant 2 | 19 | 4-6 |
| PTA-2357 VK Variant 3 | 20 | 4-6 |
| PTA-2358 VH Variant 1 | 21 | 7-9 |
| PTA-2358 VH Variant 2 | 22 | 7-9 |
| PTA-2358 VH Variant 3 | 23 | 7-9 |
| PTA-2358 VH Variant 4 | 24 | 7-9 |
| PTA-2358 VH Variant 5 | 25 | 7-9 |
| PTA-2358 VK Variant 1 | 26 | 10-12 |
| PTA-2358 VK Variant 2 | 27 | 10-12 |
| PTA-2358 VK Variant 3 | 28 | 10-12 |

Example 2

Described herein is the development of a monoclonal antibody to a cancer specific glycan epitope uniquely expressed during malignant transformation, enabling the targeting of CD66c on cancer stem cells (CSCs) without cross-reactivity with CD66c on normal cells.

CD66c and the Colorectal Stem Cell Population. Gemei et al. demonstrated that CD66c is a marker for colorectal cancer stem cells (CSC) but is not expressed on the normal stem cell population. They demonstrated that:

(a) CD66c is highly expressed in colorectal cancer but not in contiguous normal tissue;

(b) CD66c expression followed a gradient according to the malignancy of the lesion, increasing from normal tissues to adenoma and from adenoma to carcinoma;

(c) using a validated CSC marker, CD133 (reviewed in Li, Z. 2013. CD133: a stem cell biomarker and beyond. Exp Hematol Oncol. 2:17.25. PMID: 23815814), expression of which has been demonstrated to correlate with patient prognosis and survival, they demonstrated that CD133.positive cells from normal tissues were almost completely CD66c. negative whereas almost all CD133.positive cells from tumors were CD66c positive;

(d) $CD66c^{bright}$ cells (as measured by flow cytometry) were significantly increased in liver metastases of colorectal tumor cells;

(e) $CD66c^{bright}$ cells were enriched in colon spheres grown from primary patient tumors;

(f) only the $CD66c^{bright}$ cells from patients with colorectal cancer formed macroscopic tumors in NOD/SCID mice whereas the $CD66c^{dull}$ cells did not; and (g) siRNA to CD66c in the human Caco.2 cell lines (a high CD66c expressing line) reduced in vitro proliferation, increased apoptosis and necrosis, and prevent tumor formation in NOD.SCID mice, despite robust tumor formation by control cells.

These data validate CD66c as a novel colorectal CSC antigen that is critical for tumor formation and, unlike other markers such as CD133, is absent or expressed at extremely low levels in normal colorectal stem cells.

CD66c and Colorectal Cancer Stem Cells

In addition to its expression in the bulk population of many tumors, CD66c can be an important marker of CSCs and expression of CEACAM6 may even convey CSC properties on tumor cells. Haraguchi et al. characterized the side population (SP) cells from a variety of gastrointestinal tumor cell lines. The SP phenotype is due to high levels of ABC transporters that efflux fluorescent dyes such as Hoechst 33342 and has been shown to correspond to the stem cell population in a variety of normal and malignant tissues. In order to identify markers of the SP population in these tumor lines, they used an oligonucleotide microarray to analyze differentially expressed genes between SP and non. SP cells of human hepatoma HuH7 cells. They identified CD66c as the most differentially up.regulated gene in the SP population compared to non.SP cells.

Chen et al. showed that elevated levels of CD66c in pancreatic cancer cells promoted epithelial.mesenchymal transition (EMT), migration and invasion in vitro and metastasis in vivo, whereas shRNA.mediated CD66c knockdown had the opposite effect. EMT is thought to be one mechanism by which CSCs are generated and has been shown to play an important role in pancreatic metastasis. By promoting EMT, therefore, CD66c can directly induce cancer stem cell properties.

Particularly strong evidence for the role of CD66c in cancer stem cells has been demonstrated in colorectal cancer. Ilantzis et al. found that overexpression of CD66c in human colorectal cell lines induced loss of cell polarization, inhibited their ability to differentiate and increased their tumorigenicity in nude mice. Gemei et al., provided direct evidence that CD66c is a marker of colorectal CSCs, but not of normal intestinal stem cells. These authors examined the correlation between a validated stem cell marker, CD133 and CD66c in normal and cancer tissues. Strikingly, they found that CD66c is not expressed at the base of normal crypts, where the stem cell population resides, but only at the apex, where mature cells are sloughed off; in contrast, CD66c is expressed throughout the crypt in cancer tissue. Further, expression of CD66c and CD133 are mutually exclusive in normal tissues but coexpressed in colorectal tumors. These data are striking as there are very few documented molecular differences between a CSC and its normal stem cell counterpart. Many well documented markers of cancer stem cells (e.g., CD133, CD44, ALDH1A1, LGR5, etc) are also used to isolate their normal stem cell counterparts. In contrast, CD66c is a unique CSC marker that is not present on the normal stem cell population.

The normal stem cell as well as the cancer stem cell has been particularly well described in colorectal cancer, making it an excellent system for identifying drugs and biologics that distinguish the two. As mentioned above, under normal conditions, the colorectal stem cell population is delimited anatomically, being restricted to the crypts. There is constant turnover of cells in the intestine, with the stem cells forming transient amplifying cells that move up the crypt into the villus and are then sloughed off. This process is driven by cells at the base of the crypt that have the Lgr5 marker, which is a receptor for R.spondins and is part of the Wnt signaling receptor complex. Recent data indicate that this population also gives rise to the quiescent population at the +4 position from the base of the crypt that previously was thought to represent the intestinal stem cell population. As with the CD133, CD44 and Adlefluor markers, and unlike CEACAM6, Lrg5 marks both the normal stem cell population and the colorectal cancer stem cell population.

An alternative to using cell surface markers to identify colorectal CSCs is to use a functional assay like the spheroid assay. The spheroid assay makes use of the observation that CSCs, but not more differentiated tumor cells, form spheroids in serum free media. In preliminary studies, we used the colosphere assay to determine if colospheres express the antigen detected by monoclonal antibody 109.12. The antigen detected by monoclonal antibody 109.12 is expressed in colonspheres (FIG. 20). As the antigen is also expressed in the bulk tumor cell population, the amount of antigen is not enriched in the colonspheres relative to the bulk population. These data therefore represent initial evidence that the monoclonal antibody 109.12 antigen is expressed in the colorectal cancer stem cell population.

References

Fessart et al. "Three-dimensional culture model to distinguish normal from malignant human bronchial epithelial cells." Eur Respir J. 2013 42:1245-56.

Witt Hamer Philip C. De, et. al. "Quantification of Viability in Organotypic Multicellular Spheroids of Human Malignant Glioma using Lactate Dehydrogenase Activity: A Rapid and Reliable Automated Assay" Journal of Histochemistry and Cytochemistry 2005 53:23-24.

Example 3

Materials and Methods

C6f1 fragment—A 570 nucleotide fragment of CEACAM6, designated as C6f1, was PCR-amplified using a forward primer containing an EcoRI restriction site and a reverse primer containing a BglII restriction site. The PCR products were run on a 1% agarose gel to check for the product size, and the band of desired size was excised and purified using a Qiagen gel extraction kit according to the manufactures' instructions. The PCR product was then restriction enzyme-digested overnight at 37° C. in a 20 uL reaction containing 1 uL of both EcoRI and BglII enzymes from Promega. The products were once again run on a 1% agarose gel to verify product size, excised from the gel, and purified using a Qiagen gel extraction kit. Ligation of the fragment into the pFUSE vector, which had been previously treated with EcoRI and BglII, was performed using NEB T4 DNA ligase according to the manufactures' instructions. The resulting plasmid was transformed into Top 10F competent E. Coli and plated on an agar plate containing Zeocin. Single colonies were selected and expanded in 5 mL cultures, and the plasmid was purified using a Qiagen mini-prep kit. DNA sequence was verified both by size on an agarose gel and by nucleotide sequencing.

Purification of C6f1 fragment—Purification of C6f1 was performed using a Biologic DuoFlow Chromatography System. A GE Healthcare HiTrap HP Protein A column in combination with 20 mM sodium phosphate pH 7.0 binding/wash buffer (buffer A) and 100 mM citric acid pH 3.0 buffer (buffer B) were used to purify C6f1 from supernatant. The protocol for C6f1 purification with protein A column is listed below in Table 1. Fractions were taken every 5 mLs up until elution with buffer B after which they were collected every 2.5 mL until completion of the protocol.

TABLE 7

PROTOCOL FOR C6F1 PURIFICATION WITH PROTEIN A COLUMN

| Step Number | Buffer or Sample | Percentage or Gradient | Flow rate (mL/min) | Total step time (mins) |
|---|---|---|---|---|
| 1 | Buffer A | 100% | 5 | 50 |
| 2 | Load/inject sample | 100% | 5 | 150 |
| 3 | Buffer A | 100% | 5 | 50 |
| 4 | Buffer B | 100% | 5 | 25 |
| 5 | Buffer A | 100% | 5 | 50 |

Twenty microliters of each fraction from Protein A column was run on polyacrylamide gel, transferred to PVDF, and blotted using MAb109 to identify fractions containing MAb109-reactive C6f1. The reactive fractions were then pooled and concentrated using an Amicon Ultra Ultracel 30 KDa centrifugal filter before being brought up to a volume of 30 mLs with 25 mM MES pH6.5. The sample was then loaded onto the Biologic DuoFlow Chromatography system and further purified/concentrated using a GE Healthcare HiTrap Qff column with 25 mM MES pH6.5 (buffer A) and 25 mM MES pH6.5 with 1M NaCl (buffer B). The protocol for C6f1 purification/concentration using the Qff column is listed below in Table 2. Fractions were taken every 5 mL up until elution with buffer B after which they were collected every 2 mL until completion of the protocol.

TABLE 8

PROTOCOL FOR C6F1 PURIFICATION/CONCENTRATION USING QFF COLUMN

| Step Number | Buffer or Sample | Percentage or Gradient | Flow rate (mL/min) | Total step time (mins) |
|---|---|---|---|---|
| 1 | Buffer A | 100% | 1 | 10 |
| 2 | Load/inject sample | 100% | 1 | 30 |
| 3 | Buffer A | 100% | 1 | 10 |

TABLE 8-continued

PROTOCOL FOR C6F1 PURIFICATION/CONCENTRATION USING QFF COLUMN

| Step Number | Buffer or Sample | Percentage or Gradient | Flow rate (mL/min) | Total step time (mins) |
|---|---|---|---|---|
| 4 | Linear Gradient (A-B) | Gradient | 1 | 20 |
| 5 | Buffer A | 100% | 1 | 20 |

Twenty microliters of each fraction from Off column was run on polyacrylamide gel, transferred to PVDF, and blotted using MAb109 to identify fractions containing MAb109-reactive C6f1. The reactive fractions were then pooled together and concentrated using an Amicon Ultracel 30 KDa centrifugal filter and buffer exchanged into MilliQ water. Once the volume had been concentrated below 1 mL, the purified C6f1 was placed in a microcentrifuge tube and completely dried in a speed-vac. The final sample was resuspended in a desired volume of milliQ and stored at −20° C. until being used.

Expression of C6f1 in HEK Lec1 suspension cells—Cells were propagated and maintained in a 50:50 mix of Ex-Cell/Freestyle media until time of transfection. At the time of transfection, the cells are collected by centrifugation and resuspended in Freestyle™ 293 medium alone at a cell density of $2.5 \times 10^6$ cells/mL. Cells were then transfected using DNA and polyethylenimine (PEI) at final concentrations of 2.5 ug/mL and 0.5 ug/mL, respectively, in Freestyle™ 293 medium. Cells were maintained in Freestyle™ 293 medium for 24 hours post-transfection. After 24 hours, the cultures were diluted 1:1 with Ex-Cell or ESF medium with valproic acid (VPA) added to a final concentration of 2.2 mM. Cultures were then maintained for recombinant glycoprotein production for five days on a platform shaker in a $CO_2$ incubator. After five days, cultures were centrifuged to separate the cells from the suspension media containing the desired C6f1 glycoprotein. Additionally, cell culture media was passed over a 0.42 um vacuum filter before purifying using a BioRad chromatography system with a Protein A column.

MAb109 binding activity: 100 ng of purified C6f1 was spotted in triplicate for each reaction on PVDF membrane using a vacuum manifold. The membrane was blocked in 5% milk solution with TBS-T overnight at 4° C. The stock MAb109 (0.1 ug/uL) was diluted 1:3000 to a final concentration of 0.03 ng/uL in blocking solution before each competitor was added and incubated for 30 minutes at room temperature. The antibody/competitor solution was then incubated with the C6f1 spotted strip for 1 hour at room temperature. After 1 hour, the strips were washed three times with TBS-T for 5 minutes each wash. The secondary antibody was Santa Cruz anti-mouse IgG HRP diluted 1:5000 and incubated at room temperature for 30 minutes. Three TBS-T washes were repeated before adding Perkin-Elmer Western Lightening Plus-ECL according to the manufacturer's instructions. Blots were exposed to x-ray film for 10 minutes before developing. After developing, the film was scanned, and densitometry was performed using ImageJ software.

Cloning and expression of CEACAM6 fragments/mutants— PCR cloning of fragments of C6f1 was performed using HotStarTaq DNA Polymerase by Qiagen according to the manufacturer's instructions using C6f1-pFUSE as the template. The forward and reverse PCR primers were designed with EcoRI and BlgII restriction sites, respectively, in order to facilitate cloning into pFUSE vector. Primer sequences are as follows: Ig1F: GAATTCAAAGCCCTC-CATCTCCAGC (SEQ ID NO:106), Ig1R: AGATCTAT-TCAGGGTGACTGGGTC (SEQ ID NO:107), Ig2F: GAATTCAGATGGCCCCACCATTTGG (SEQ ID NO:108), Ig2R: AGATCTGGTGACTGTGGTCCTATT (SEQ ID NO:109), peptide3F: GAATT-CACTGCAGCTGTCCAATGGC (SEQ ID NO:110), and peptide3R: AGATCTTTTGACGCTGAGTAGAGT (SEQ ID NO:111). PCR products were restriction enzyme digested with EcoRI and BglII transformed using Promega restriction enzymes, ethanol/chloroform-precipitated, and ligated into a prepared pFUSE vector using NEB T4 DNA ligase according to the manufacturers instructions. Top1OF competent cells were transformed and plated on agar plates containing Zeocin. Several clones were selected, grown, and plasmid prepped before inserts being verified using restriction enzyme digests with EcoRI and BglII as well as DNA sequencing.

Site directed mutagenesis of C6f1 and C8f1 was performed using a Stratagene QuikChange site-directed mutagenesis kit according to the manufacturer's protocol. The primers for both the C6f1 $^{300}QAH^{302}$ to $^{300}HTT^{302}$ and C8f1 $^{300}HTT^{302}$ to $^{300}QAH^{302}$ were C6f1 $^{300}HTT^{302}$ forward: GCGGATCCTATATGTGCCACAC-CACTAACTCAGCCACTGGCCTC (SEQ ID NO:112)and reverse: GAGGCCAGTGGCTGAGT-TAGTGGTGTGGCACATATAGGATCCGC (SEQ ID NO:113). C8f1 $^{300}QAH^{302}$ forward: GGATCC-TATGCCTGCCAAGCCCATAACTCAGCCACTGGC (SEQ ID NO:114) and reverse: GCCAGTGGCTGAGT-TATGGGCTTGGCAGGCATAGGATCC (SEQ ID NO:115). PCR products were transformed using XL-1 blue competent cells and plated on agar plates containing Zeocin. Several clones were selected, grown, and plasmid prepped before inserts being verified using restriction enzyme digests with EcoRI and BglII as well as DNA sequencing.

Example 4

Characterization of the MAb 109 Epitope.

We characterized the epitope recognized by MAb 109 using enzymatic treatments. We had shown that MAb 109 reacted with an N-linked glycan quality BxPC3 cells, a human pancreatic adenocarcinoma (PDAC cel) 1 line. Total cell lysates of is that were analyzed by immunoblotting with MAb 109. As shown in the left-hand panel of FIG. 21, MAb 109 reacted with a polypeptide having an approximate molecular weight of 85 kD. Treatment of the lysates with PNGase F (Peptide:N-Glycosidase F) a glycosylated base that removes human N-linked glycans abolished MAb 109 reactivity. When the immunoblotting was probed with a commercially available anti-CEACAM6 polypeptide antibody, a polypeptide of about 45 kD was detected (right hand panel). The shift in molecular weight was consistent with the removal of the N glycans on the polypeptide. These data showed that the MAb 109 epitope was sensitive to treatment of CEACAM6 with PNGase F, which hydrolyzes vertebrate N-linked glycans.

As shown in FIG. 22, CEACAM6 is a member of the CEA family MAb109 reacts with CEACAM5 and 6 but does not react with CEACAM5. CEACAM6 is much smaller than CEACAM5; therefore, the epitope recognized by MAb 109 is unrelated to the sequences common to these two proteins. As shown in FIG. 23, CEACAM6 contains 3 domains, V, C1, and C2, with 12 potential N-linked structures.

The cDNA sequence encoding the V domain was removed from that of the C1 and C2 domains and subcloned into the pFUSE vector as described above. The region of the protein in this vector will be referred to as C6f1. As shown in FIG. 25, when the vector was expressed in HEK-293 cells, it produced a glycoprotein that by immunoblotting using MAb109, after SDS-PAGE, was the molecular weight predicted. The C6f1 109 epitope was sensitive to PNGase F. Using a commercial antibody against CEACAM6 polypeptide, this epitope remained after immunoblotting as expected, but the molecular weight of the treated protein was reduced, which was consistent with the removal of the N-glycans on C6f1 by PNGase F.

Treatment of C6f1 from HEK cells with various glycosidases did not result in a loss of MAb109 binding as shown in FIG. 26. C6f1 was expressed in mutant HEK cells that lacked N-acetylglucosaminyltransferase I activity (Lec1HEK), which results in N-glycans that are not fully processed and contain essentially Mannose and N-acetylglucosamine (Man and GlcNAc); primarily Man5GlcNAc2. These N-glycans are sensitive to both glycosidases, Endo-beta-galactosidase F and H. MAb109 showed strong binding to C6f1 expressed in Lec1HEK. The epitope remains sensitive to PNGase F treatment. The N-glycans on C6f1Lec1 are sensitive to Endo F treatment, but MAb109 still binds to it. Thus, the epitope did not appear to depend on an extended N-glycan structure. The CEACAM 6 fragment 1 N-glycans expressed in Lec1HEK cells are illustrated in FIG. 27.

As shown in FIG. 28, treatment of Lec1C6f1 with endo-beta-galactosidase F or H, resulted in hydrolysis of the Man5GlcNAc2, leaving a single GlcNAc attached to the protein. The CEACAM6 fragment 1 N-glycans expressed in Lec1HEK cells after Endo H treatment are illustrated in FIG. 29.

Example 5

Characterization of the MAb 109 Epitope: Mutagenesis Analysis.

An alignment alignment of the C-terminal amino acid sequences of CEACAM5, CEACAM6, and CEACAM8 is shown in FIG. 30. CEACAM5 and CEACAM6 express the epitope recognized by MAb 109 and CEACAM8 does not. The main difference between the sequences was at the region at aa300 of the C6f1 sequence. Both CEACAM5 and CEACAM6 included the segment QAH. The corresponding segment in CEACAM8 was HTT.

We performed site directed mutagenesis on this region as described above. The results of this experiment are shown in FIG. 31. Mutagenesis experiments in which the QAH of C6f1 was changed to HTT eliminated binding by MAb109. Mutagenesis experiments in which the QAH of C6f1 was changed to HTT eliminated binding by MAb109. Conversely, mutagenesis experiments in which the HTT of CEACAM8 was changed to QAH resulted in MAb109 binding, as shown in FIG. 32. Changing either H300Q or T302H of CEACAM8 did not render it positive for MAb109 binding. Changing both H300Q and T302H (and not A301T) of CEACAM8, however, did cause result in binding as shown in FIG. 33. These experiments suggested that H300 and T302 were needed for either MAb109 binding or the biosynthesis of the epitope.

To determine if an N-linked structure at some other location on C6f1 could be involved in MAb binding, each of the 9 N-linked sequons was mutated sequentially. As shown in FIG. 34, when N309 was mutated to N309A, MAb binding was absent, showing only the glycan on this sequon was involved.

FIG. 35 shows the location of N309 relative to the QAH region. Both of these are in the C2 region. When the Cysteines of C6f1 were reduced by Beta-mercaptoethanol treatment, followed by reductive alkylation with iodoacetamide to block re-association, and the resulting glycoprotein subjected to SDS-PAGE and Western blotting using MAb 109, the antibody still bound. Taken together, these data suggested that secondary protein structure was not likely to be involved in MAb109 binding, although it could be involved in biosynthesis of the epitope. Additional mutagenesis experiments were performed on the peptide segment, as part of C6f1, around Q300 to V318. Results are shown in FIG. 36.

The effect of mutations on MAb109 binding was further analyzed using a dot blot assay. Native C6f1 was spotted on nitrocellulose; after drying, the nitrocellulose was blocked with BSA solution and washed. MAb109 was pre-incubated with a mutated C6f1 for 2 hrs., and then this solution is applied to the dot-blot. After 2 hours, the nitrocellulose was washed and probed with phosphatase-conjugated goat anti-mouse antibody to detect MAb109 binding to the dot-blot. If the mutated C6f1 is active, then it competes efficiently for MAb109 binding; an inactive C6f1 does not compete with MAb109 binding. The results of these experiments are summarized in FIG. 37. Specific residues are shown in either green, red, or orange. Green means the change in this amino acid produced a C6f1 that retains MAb109 binding activity. Red means the change in this amino acid produced a C6f1 that loses MAb109 binding activity. Orange means the change in this amino acid produced a C6f1 that loses most but not all MAb109 binding activity.

Using peptide and glycopeptide synthetic techniques the Q300 to R326 peptide and the same peptide with a single GlcNAc residue at N309 were tested for MAb binding. These sequences are shown in FIG. 38. The additional 8 amino acids C-terminal to V318 were added because the peptide Q300 to R326 is a tryptic peptide produced when C6f1 fused to Fc (in the P-fuse vector) is treated with trypsin. At a concentration of 30 nmicromolar, neither peptide inhibited MAb binding. This result suggested that the epitope does not contain only Q300 to R326 with a single GlcNAc on N309.

In order to simplify the minimal glycopeptide at the C-terminus that is bound by MAb109, synthetic cDNAs were synthesized and inserted into expression vectors, and expressed in HEK-T cells. A TEV cleavage site, a short linker to allow TEV easy access to its cleavage site, an His-tag, and sequences encoding GFP were inserted downstream from the final V318. As shown in FIG. 39, the glycopeptide #6, when expressed in HEK cells and affinity purified showed MAb binding activity. The glycopeptide #10, lacking 27 amino acids at the N-terminus, however, was not active. Glycopeptide #8, Q300-V318, was inactive, agreeing with the synthetic glycopeptide result. A major difference between glycopeptides #6 and #7 is that #7 does not contain the C259, which generally forms a di-sulfide bond with C299.

The mutant C6f1 with C299A also was not active (see above). These results, taken together, suggest that the di-sulfide loop that naturally forms between C259 and C299 is required for biosynthesis of the MAb109 epitope. We next introduced a C259A mutation and expressed this glycopeptide to test this hypothesis. The #6 glycopeptide sequence with C259A mutation was inactive.

These data suggested that MAb109 binding may require a minimum of a single GlcNAc residue attached to N309; it also may require other residues in the vicinity. This binding does not appear to require secondary peptide structure (disulfides) since the glycopeptide after reduction and alkylation and SDS-PAGE, followed by Western blotting on PVDF, shows MAb 109 binding activity. In addition, since mutation of either C299A and 259A results in loss of MAb binding, the disulfide bridge between these cysteines must be present for epitope biosynthesis. So, the following appear to be needed for biosynthesis and/or MAb109 binding on nitrocellulose: a disulfide bridge C259-C299; GlcNAc on N309; Q300 and H302; and S304

Since MAb 109 binds to glycopeptide and C6f1 after beta-mercaptoethanol and iodoacetamide reactions, followed by SDS-PAGE denaturation and transfer to nitrocellulose, Mab 109 binding does not require disulfide bridge C259-C299. Yet by mutation and truncation experiments, this disulfide bridge appears to be needed for epitope expression. Since synthetic glycopeptide Q300 to R326 with GlcNAc on N309 was not bound by MAb109, there must be a modification of the glycopeptide in addition to GlcNAc-N309 that is part of MAb109 epitope; this modification must require disulfide bridge C259-C299.

Example 6

Detection of the Mab 109 Epitope in Pancreatic Cancer Samples.

A capture ELISA assay was developed where MAb109 coated on ELISA wells was used to capture epitope from sera from pancreatic cancer serum and non-diseased control serum. Captured CEACAM6 was then detected using a commercial polyclonal antibody as shown in FIG. 40. Levels of CEACAM6 in normal serum and replicated assays were 1.0 and 3.5 ng/mL. Levels of CEACAM6 in serum from pancreatic cancer patients were 154.34 and 146.64 ng/mL.

The capture ELISA assay was used to detect the CEACAM6 epitope recognized by Mab 109 in a larger cohort of samples. As shown in FIG. 41, there was a statistically significant difference between levels of the CEACAM6 epitope recognized by Mab 109 in sera from pancreatic cancer patients and non-diseased sera, p=0.036. FIGS. 42 and 43 show the results of an ELISA comparing levels of the CEACAM6 epitope recognized by Mab 109 in serum from patients suffering from chronic pancreatitis, pancreatic carcinoma, and non-diseased controls.

SEQUENCE LISTING

```
<160> NUMBER OF SEQ ID NOS: 115

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Thr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Ile Ser Thr Tyr Ser Gly Asn Thr Asn Asn Asn Gln Lys Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Asp Tyr Tyr Gly Ser Phe Tyr Lys Phe Glu Tyr
1               5                   10

<210> SEQ ID NO 4
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Asn Val Leu Ser Ile Pro Tyr Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Tyr Tyr Met His
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ile Asp Pro Gly Asn Gly Asp Thr Glu Cys Ala Pro Lys Phe Gln
1               5                   10                  15

Gly

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Pro Tyr Tyr Ser Gly Ser Ser His Phe Asp Tyr
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Lys Ser Val Ser Ala Ser Gly Tyr Ser Phe Leu His
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Ala Ser Asn Leu Glu Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln His Ser Arg Glu Leu Arg Thr
1               5

<210> SEQ ID NO 13
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Pro Glu Leu Lys Lys Pro Gly Ala
1               5                   10                  15

Ser Val Lys Val Ser Cys Lys Gly Ser Gly Tyr Pro Phe Thr Asp Tyr
                20                  25                  30

Thr Ile His Trp Val Arg Gln Ala His Gly Gln Gly Leu Glu Trp Ile
            35                  40                  45

Gly His Ile Ser Thr Tyr Ser Gly Asn Thr Asn Asn Gln Lys Phe
        50                  55                  60

Lys Gly Arg Ala Thr Met Thr Val Asp Lys Ser Thr Ser Thr Ala Tyr
65                  70                  75                  80

Met Glu Leu Arg Ser Leu Arg Ser Asp Asp Ser Thr Val Tyr Tyr Cys
                85                  90                  95

Ala Arg Gly Asp Tyr Tyr Gly Ser Phe Tyr Lys Phe Gly Tyr Trp Gly
            100                 105                 110
```

```
Gln Gly Thr Thr Val Thr Val Ser Ser
        115                 120

<210> SEQ ID NO 14
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Pro Phe Thr Asp Tyr
            20                  25                  30

Thr Ile His Trp Val Arg Gln Ala His Gly Gln Gly Leu Glu Trp Ile
        35                  40                  45

Gly His Ile Ser Thr Tyr Ser Gly Asn Thr Asn Asn Gln Lys Phe
    50                  55                  60

Lys Gly Arg Ala Thr Met Thr Val Asp Lys Ser Thr Ser Thr Ala Tyr
65                  70                  75                  80

Met Glu Leu Arg Ser Leu Arg Ser Asp Asp Ser Thr Val Tyr Tyr Cys
                85                  90                  95

Ala Arg Gly Asp Tyr Tyr Gly Ser Phe Tyr Lys Phe Glu Tyr Trp Gly
            100                 105                 110

Gln Gly Thr Thr Val Thr Val Ser Ser
        115                 120

<210> SEQ ID NO 15
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Pro Phe Thr Asp Tyr
            20                  25                  30

Thr Ile His Trp Val Arg Gln Ala Pro Gly Gln Gly Leu Glu Trp Ile
        35                  40                  45

Gly His Ile Ser Thr Tyr Ser Gly Asn Thr Asn Asn Asn Gln Lys Phe
    50                  55                  60

Lys Gly Arg Ala Thr Met Thr Val Asp Lys Ser Thr Ser Thr Ala Tyr
65                  70                  75                  80

Met Glu Leu Arg Ser Leu Arg Ser Asp Asp Thr Thr Val Tyr Tyr Cys
                85                  90                  95

Ala Arg Gly Asp Tyr Tyr Gly Ser Phe Tyr Lys Phe Glu Tyr Trp Gly
            100                 105                 110

Gln Gly Thr Thr Val Thr Val Ser Ser
        115                 120

<210> SEQ ID NO 16
<211> LENGTH: 121
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Pro Phe Thr Asp Tyr
                20                  25                  30

Thr Ile His Trp Val Arg Gln Ala Pro Gly Gln Gly Leu Glu Trp Ile
            35                  40                  45

Gly His Ile Ser Thr Tyr Ser Gly Asn Thr Asn Asn Gln Lys Phe
    50                  55                  60

Lys Gly Arg Ala Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Tyr Tyr Gly Ser Phe Tyr Lys Phe Glu Tyr Trp Gly
            100                 105                 110

Gln Gly Thr Thr Val Thr Val Ser Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Pro Phe Thr Asp Tyr
                20                  25                  30

Thr Ile His Trp Val Arg Gln Ala Pro Gly Gln Gly Leu Glu Trp Ile
            35                  40                  45

Gly His Ile Ser Thr Tyr Ser Gly Asn Thr Asn Asn Gln Lys Phe
    50                  55                  60

Lys Gly Arg Val Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Tyr Tyr Gly Ser Phe Tyr Lys Phe Glu Tyr Trp Gly
            100                 105                 110

Gln Gly Thr Thr Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Lys Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala 20                  25                  30

Leu Asn Trp Phe Gln Arg Lys Gln Gly Lys Ala Pro Lys Leu Leu Ile
            35                  40                  45

Tyr Gly Ala Thr Asn Leu Ala Asp Gly Met Pro Ser Arg Phe Ser Gly
        50                  55                  60

Ser Gly Ser Gly Arg Asp Phe Thr Leu Thr Ile Ser Ser Leu Gln Pro
65                  70                  75                  80

Glu Asp Phe Ala Thr Tyr Phe Cys Gln Asn Val Leu Ser Ile Pro Tyr
                85                  90                  95

Thr Phe Gly Gln Gly Thr Gln Leu Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Lys Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Phe Gln Arg Lys Pro Gly Lys Ala Pro Lys Leu Leu Ile
            35                  40                  45

Tyr Gly Ala Thr Asn Leu Ala Asp Gly Met Pro Ser Arg Phe Ser Gly
        50                  55                  60

Ser Gly Ser Gly Arg Asp Phe Thr Leu Thr Ile Ser Ser Leu Gln Pro
65                  70                  75                  80

Glu Asp Phe Ala Thr Tyr Phe Cys Gln Asn Val Leu Ser Ile Pro Tyr
                85                  90                  95

Thr Phe Gly Gln Gly Thr Lys Leu Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Phe Gln Arg Lys Pro Gly Lys Ala Pro Lys Leu Leu Ile
            35                  40                  45

Tyr Gly Ala Thr Asn Leu Ala Asp Gly Met Pro Ser Arg Phe Ser Gly
        50                  55                  60

Ser Gly Ser Gly Arg Asp Phe Thr Leu Thr Ile Ser Ser Leu Gln Pro
65                  70                  75                  80

Glu Asp Phe Ala Thr Tyr Phe Cys Gln Asn Val Leu Ser Ile Pro Tyr
                85                  90                  95

Thr Phe Gly Gln Gly Thr Lys Leu Glu Ile Lys

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 21

Glu Val Gln Leu Val Gln Ser Gly Ala Glu Leu Lys Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Ala Pro Gly Gln Gly Leu Glu Trp Ile
        35                  40                  45

Gly Trp Ile Asp Pro Gly Asn Gly Asp Thr Glu Cys Ala Pro Lys Phe
    50                  55                  60

Gln Gly Arg Ala Thr Leu Thr Ala Asp Thr Ser Ile Asn Thr Ala Tyr
65                  70                  75                  80

Leu Glu Leu Ser Arg Leu Arg Ser Asp Asp Thr Ala Val Tyr Tyr Cys
                85                  90                  95

Asn Ala Pro Tyr Tyr Ser Gly Ser Ser His Phe Asp Tyr Trp Gly Gln
            100                 105                 110

Gly Thr Thr Val Thr Val Ser Ser
        115                 120

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

Glu Val Gln Leu Val Gln Ser Gly Ala Glu Val Lys Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Ala Pro Gly Gln Gly Leu Glu Trp Ile
        35                  40                  45

Gly Trp Ile Asp Pro Gly Asn Gly Asp Thr Glu Cys Ala Pro Lys Phe
    50                  55                  60

Gln Gly Arg Ala Thr Leu Thr Ala Asp Thr Ser Ile Asn Thr Ala Tyr
65                  70                  75                  80

Leu Glu Leu Ser Arg Leu Arg Ser Asp Asp Thr Ala Val Tyr Tyr Cys
                85                  90                  95

Asn Ala Pro Tyr Tyr Ser Gly Ser Ser His Phe Asp Tyr Trp Gly Gln
            100                 105                 110

Gly Thr Thr Val Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 23

Glu Val Gln Leu Val Gln Ser Gly Ala Glu Val Lys Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Trp Ile Asp Pro Gly Asn Gly Asp Thr Glu Cys Ala Pro Lys Phe
    50                  55                  60

Gln Gly Arg Ala Thr Leu Thr Ala Asp Thr Ser Ile Asn Thr Ala Tyr
65                  70                  75                  80

Leu Glu Leu Ser Arg Leu Arg Ser Asp Asp Thr Ala Val Tyr Tyr Cys
                85                  90                  95

Asn Ala Pro Tyr Tyr Ser Gly Ser Ser His Phe Asp Tyr Trp Gly Gln
            100                 105                 110

Gly Thr Thr Val Thr Val Ser Ser
        115                 120

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Gln Ser Gly Ala Glu Val Lys Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Trp Ile Asp Pro Gly Asn Gly Asp Thr Glu Cys Ala Pro Lys Phe
    50                  55                  60

Gln Gly Arg Ala Thr Leu Thr Ala Asp Thr Ser Ile Ser Thr Ala Tyr
65                  70                  75                  80

Leu Glu Leu Ser Arg Leu Arg Ser Asp Asp Thr Ala Val Tyr Tyr Cys
                85                  90                  95

Asn Ala Pro Tyr Tyr Ser Gly Ser Ser His Phe Asp Tyr Trp Gly Gln
            100                 105                 110

Gly Thr Thr Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Tyr
            20                  25                  30

```
Tyr Met His Trp Val Arg Gln Ala Pro Gly Gln Gly Leu Glu Trp Ile
        35                  40                  45

Gly Trp Ile Asp Pro Gly Asn Gly Asp Thr Glu Cys Ala Pro Lys Phe
 50                  55                  60

Gln Gly Arg Ala Thr Ile Thr Ala Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Asn Ala Pro Tyr Tyr Ser Gly Ser Ser His Phe Asp Tyr Trp Gly Gln
                100                 105                 110

Gly Thr Thr Val Thr Val Ser Ser
                115                 120

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Ser Ala Ser
                20                  25                  30

Gly Tyr Ser Phe Leu His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
 50                 55                  60

Arg Phe Ser Gly Ser Gly Ser Gly Thr Asp Phe Thr Leu Thr Ile Ser
65                  70                  75                  80

Ser Leu Gln Glu Glu Asp Val Ala Thr Tyr Tyr Cys Gln His Ser Arg
                85                  90                  95

Glu Leu Arg Thr Phe Gly Gln Gly Thr Lys Leu Glu Ile Lys
                100                 105                 110

<210> SEQ ID NO 27
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Ser Ala Ser
                20                  25                  30

Gly Tyr Ser Phe Leu His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
 50                 55                  60

Arg Phe Ser Gly Ser Gly Ser Gly Thr Asp Phe Thr Leu Thr Ile Ser
65                  70                  75                  80

Ser Leu Gln Ala Glu Asp Val Ala Thr Tyr Tyr Cys Gln His Ser Arg
                85                  90                  95
```

```
Glu Leu Arg Thr Phe Gly Gln Gly Thr Lys Leu Glu Ile Lys
            100                 105                 110
```

<210> SEQ ID NO 28
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Ala Ser
            20                  25                  30

Gly Tyr Ser Phe Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Arg Thr Phe Gly Gln Gly Thr Lys Leu Glu Ile Lys
            100                 105                 110
```

<210> SEQ ID NO 29
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 29

```
cag gtc cag ctg gtg cag tct ggg cct gag ctg aag aag cct ggg gcc      48
Gln Val Gln Leu Val Gln Ser Gly Pro Glu Leu Lys Lys Pro Gly Ala
1               5                   10                  15 tca gtg aag gtg tcc tgc aag ggt tcc ggc tac cca ttc act gat tat      96
Ser Val Lys Val Ser Cys Lys Gly Ser Gly Tyr Pro Phe Thr Asp Tyr
            20                  25                  30 act ata cac tgg gtg agg cag gcc cat ggc cag ggc cta gag tgg att     144
Thr Ile His Trp Val Arg Gln Ala His Gly Gln Gly Leu Glu Trp Ile
        35                  40                  45 gga cat att agt acc tac tct ggt aac acc aac aac aac cag aag ttt     192
Gly His Ile Ser Thr Tyr Ser Gly Asn Thr Asn Asn Asn Gln Lys Phe
    50                  55                  60 aag ggc agg gcc aca atg act gta gac aaa tcc acc agc aca gcc tat     240
Lys Gly Arg Ala Thr Met Thr Val Asp Lys Ser Thr Ser Thr Ala Tyr
65                  70                  75                  80 atg gaa ctt agg agc ttg agg tct gac gat tct acc gtg tat tac tgt     288
Met Glu Leu Arg Ser Leu Arg Ser Asp Asp Ser Thr Val Tyr Tyr Cys
                85                  90                  95 gca aga ggg gat tac tac ggt agt ttc tac aaa ttt gaa tac tgg ggc     336
Ala Arg Gly Asp Tyr Tyr Gly Ser Phe Tyr Lys Phe Glu Tyr Trp Gly
            100                 105                 110 caa ggc acc act gtg aca gtc tcc tca                                 363
```

```
Gln Gly Thr Thr Val Thr Val Ser Ser
        115                 120
```

```
<210> SEQ ID NO 30
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 30 cag gtc cag ctg gtg cag tct ggg gcc gag gtg aag aag cct ggg gcc       48
Gln Val Gln Leu Val Gln Ser Gly Ala Glu Val Lys Lys Pro Gly Ala
1               5                   10                  15 tca gtg aag gtg tcc tgc aag ggt tcc ggc tac cca ttc act gat tat       96
Ser Val Lys Val Ser Cys Lys Gly Ser Gly Tyr Pro Phe Thr Asp Tyr
            20                  25                  30 act ata cac tgg gtg agg cag gcc cat ggc cag ggc cta gag tgg att      144
Thr Ile His Trp Val Arg Gln Ala His Gly Gln Gly Leu Glu Trp Ile
        35                  40                  45 gga cat att agt acc tac tct ggt aac acc aac aac aac cag aag ttt      192
Gly His Ile Ser Thr Tyr Ser Gly Asn Thr Asn Asn Asn Gln Lys Phe
    50                  55                  60 aag ggc agg gcc aca atg act gta gac aaa tcc acc agc aca gcc tat      240
Lys Gly Arg Ala Thr Met Thr Val Asp Lys Ser Thr Ser Thr Ala Tyr
65                  70                  75                  80 atg gaa ctt agg agc ttg agg tct gac gat tct acc gtg tat tac tgt      288
Met Glu Leu Arg Ser Leu Arg Ser Asp Asp Ser Thr Val Tyr Tyr Cys
                85                  90                  95 gca aga ggg gat tac tac ggt agt ttc tac aaa ttt gaa tac tgg ggc      336
Ala Arg Gly Asp Tyr Tyr Gly Ser Phe Tyr Lys Phe Glu Tyr Trp Gly
            100                 105                 110 caa ggc acc act gtg aca gtc tcc tca                                   363
Gln Gly Thr Thr Val Thr Val Ser Ser
        115                 120
```

```
<210> SEQ ID NO 31
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 31 cag gtc cag ctg gtg cag tct ggg gcc gag gtg aag aag cct ggg gcc       48
Gln Val Gln Leu Val Gln Ser Gly Ala Glu Val Lys Lys Pro Gly Ala
1               5                   10                  15 tca gtg aag gtg tcc tgc aag ggt tcc ggc tac cca ttc act gat tat       96
Ser Val Lys Val Ser Cys Lys Gly Ser Gly Tyr Pro Phe Thr Asp Tyr
            20                  25                  30 act ata cac tgg gtg agg cag gcc cct ggc cag ggc cta gag tgg att      144
Thr Ile His Trp Val Arg Gln Ala Pro Gly Gln Gly Leu Glu Trp Ile
        35                  40                  45 gga cat att agt acc tac tct ggt aac acc aac aac aac cag aag ttt      192
Gly His Ile Ser Thr Tyr Ser Gly Asn Thr Asn Asn Asn Gln Lys Phe
    50                  55                  60
```

```
aag ggc agg gcc aca atg act gta gac aaa tcc acc agc aca gcc tat    240
Lys Gly Arg Ala Thr Met Thr Val Asp Lys Ser Thr Ser Thr Ala Tyr
 65                  70                  75                  80 atg gaa ctt agg agc ttg agg tct gac gat acc acc gtg tat tac tgt    288
Met Glu Leu Arg Ser Leu Arg Ser Asp Asp Thr Thr Val Tyr Tyr Cys
                 85                  90                  95 gca aga ggg gat tac tac ggt agt ttc tac aaa ttt gaa tac tgg ggc    336
Ala Arg Gly Asp Tyr Tyr Gly Ser Phe Tyr Lys Phe Glu Tyr Trp Gly
            100                 105                 110 caa ggc acc act gtg aca gtc tcc tca                                363
Gln Gly Thr Thr Val Thr Val Ser Ser
        115                 120

<210> SEQ ID NO 32
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 32 cag gtc cag ctg gtg cag tct ggg gcc gag gtg aag aag cct ggg gcc     48
Gln Val Gln Leu Val Gln Ser Gly Ala Glu Val Lys Lys Pro Gly Ala
 1               5                  10                  15 tca gtg aag gtg tcc tgc aag ggt tcc ggc tac cca ttc act gat tat     96
Ser Val Lys Val Ser Cys Lys Gly Ser Gly Tyr Pro Phe Thr Asp Tyr
                20                  25                  30 act ata cac tgg gtg agg cag gcc cct ggc cag ggc cta gag tgg att    144
Thr Ile His Trp Val Arg Gln Ala Pro Gly Gln Gly Leu Glu Trp Ile
            35                  40                  45 gga cat att agt acc tac tct ggt aac acc aac aac aac cag aag ttt    192
Gly His Ile Ser Thr Tyr Ser Gly Asn Thr Asn Asn Asn Gln Lys Phe
        50                  55                  60 aag ggc agg gcc aca atg act gta gac aaa tcc acc agc aca gcc tat    240
Lys Gly Arg Ala Thr Met Thr Val Asp Lys Ser Thr Ser Thr Ala Tyr
 65                  70                  75                  80 atg gaa ctt agg agc ttg agg tct gac gat acc gcc gtg tat tac tgt    288
Met Glu Leu Arg Ser Leu Arg Ser Asp Asp Thr Ala Val Tyr Tyr Cys
                 85                  90                  95 gca aga ggg gat tac tac ggt agt ttc tac aaa ttt gaa tac tgg ggc    336
Ala Arg Gly Asp Tyr Tyr Gly Ser Phe Tyr Lys Phe Glu Tyr Trp Gly
            100                 105                 110 caa ggc acc act gtg aca gtc tcc tca                                363
Gln Gly Thr Thr Val Thr Val Ser Ser
        115                 120

<210> SEQ ID NO 33
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 33 cag gtc cag ctg gtg cag tct ggg gcc gag gtg aag aag cct ggg gcc     48
Gln Val Gln Leu Val Gln Ser Gly Ala Glu Val Lys Lys Pro Gly Ala
 1               5                  10                  15
```

```
tca gtg aag gtg tcc tgc aag ggt tcc ggc tac cca ttc act gat tat    96
Ser Val Lys Val Ser Cys Lys Gly Ser Gly Tyr Pro Phe Thr Asp Tyr
         20                  25                  30 act ata cac tgg gtg agg cag gcc cct ggc cag ggc cta gag tgg att   144
Thr Ile His Trp Val Arg Gln Ala Pro Gly Gln Gly Leu Glu Trp Ile
     35                  40                  45 gga cat att agt acc tac tct ggt aac acc aac aac cag aag ttt       192
Gly His Ile Ser Thr Tyr Ser Gly Asn Thr Asn Asn Gln Lys Phe
 50                  55                  60 aag ggc agg gtg aca atg act gta gac aaa tcc acc agc aca gcc tat   240
Lys Gly Arg Val Thr Met Thr Val Asp Lys Ser Thr Ser Thr Ala Tyr
65                  70                  75                  80 atg gaa ctt agg agc ttg agg tct gac gat acc gcc gtg tat tac tgt   288
Met Glu Leu Arg Ser Leu Arg Ser Asp Asp Thr Ala Val Tyr Tyr Cys
                 85                  90                  95 gca aga ggg gat tac tac ggt agt ttc tac aaa ttt gaa tac tgg ggc   336
Ala Arg Gly Asp Tyr Tyr Gly Ser Phe Tyr Lys Phe Glu Tyr Trp Gly
            100                 105                 110 caa ggc acc act gtg aca gtc tcc tca                                363
Gln Gly Thr Thr Val Thr Val Ser Ser
        115                 120

<210> SEQ ID NO 34
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(321)

<400> SEQUENCE: 34 gac atc aag atg act cag tct cca agc tca ctg tct gca tct gtg gga    48
Asp Ile Lys Met Thr Gln Ser Pro Ser Ser Leu Ser Ala Ser Val Gly
1               5                  10                  15 gac agg gtc acc atc aca tgt gga gca agt gag aat att tac ggt gct    96
Asp Arg Val Thr Ile Thr Cys Gly Ala Ser Glu Asn Ile Tyr Gly Ala
             20                  25                  30 tta aat tgg ttc cag cgg aaa cag gga aaa gcc cct aag ctc ctg atc   144
Leu Asn Trp Phe Gln Arg Lys Gln Gly Lys Ala Pro Lys Leu Leu Ile
         35                  40                  45 tat ggt gca acc aac ttg gca gat ggc atg cct tcg agg ttc agt ggc   192
Tyr Gly Ala Thr Asn Leu Ala Asp Gly Met Pro Ser Arg Phe Ser Gly
 50                  55                  60 agt gga tct ggt aga gac ttc acc ctc acc atc agc agc ctg cag cct   240
Ser Gly Ser Gly Arg Asp Phe Thr Leu Thr Ile Ser Ser Leu Gln Pro
65                  70                  75                  80 gag gat ttc gca acg tat ttc tgt caa aat gtg tta agt atc cct tac   288
Glu Asp Phe Ala Thr Tyr Phe Cys Gln Asn Val Leu Ser Ile Pro Tyr
                 85                  90                  95 act ttt ggc cag ggg acc cag ctg gag atc aaa                       321
Thr Phe Gly Gln Gly Thr Gln Leu Glu Ile Lys
            100                 105

<210> SEQ ID NO 35
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
```

<220> FEATURE:
<221> NAME/KEY: CDS
<222> LOCATION: (1)..(321)

<400> SEQUENCE: 35

```
gac atc aag atg act cag tct cca agc tca ctg tct gca tct gtg gga      48
Asp Ile Lys Met Thr Gln Ser Pro Ser Ser Leu Ser Ala Ser Val Gly
1               5                   10                  15 gac agg gtc acc atc aca tgt gga gca agt gag aat att tac ggt gct      96
Asp Arg Val Thr Ile Thr Cys Gly Ala Ser Glu Asn Ile Tyr Gly Ala
            20                  25                  30 tta aat tgg ttc cag cgg aaa cct gga aaa gcc cct aag ctc ctg atc     144
Leu Asn Trp Phe Gln Arg Lys Pro Gly Lys Ala Pro Lys Leu Leu Ile
        35                  40                  45 tat ggt gca acc aac ttg gca gat ggc atg cct tcg agg ttc agt ggc     192
Tyr Gly Ala Thr Asn Leu Ala Asp Gly Met Pro Ser Arg Phe Ser Gly
    50                  55                  60 agt gga tct ggt aga gac ttc acc ctc acc atc agc agc ctg cag cct     240
Ser Gly Ser Gly Arg Asp Phe Thr Leu Thr Ile Ser Ser Leu Gln Pro
65                  70                  75                  80 gag gat ttc gca acg tat ttc tgt caa aat gtg tta agt atc cct tac     288
Glu Asp Phe Ala Thr Tyr Phe Cys Gln Asn Val Leu Ser Ile Pro Tyr
                85                  90                  95 act ttt ggc cag ggg acc aag ctg gag atc aaa                         321
Thr Phe Gly Gln Gly Thr Lys Leu Glu Ile Lys
                100                 105
```

<210> SEQ ID NO 36
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(321)

<400> SEQUENCE: 36

```
gac atc cag atg act cag tct cca agc tca ctg tct gca tct gtg gga      48
Asp Ile Gln Met Thr Gln Ser Pro Ser Ser Leu Ser Ala Ser Val Gly
1               5                   10                  15 gac agg gtc acc atc aca tgt gga gca agt gag aat att tac ggt gct      96
Asp Arg Val Thr Ile Thr Cys Gly Ala Ser Glu Asn Ile Tyr Gly Ala
            20                  25                  30 tta aat tgg ttc cag cgg aaa cct gga aaa gcc cct aag ctc ctg atc     144
Leu Asn Trp Phe Gln Arg Lys Pro Gly Lys Ala Pro Lys Leu Leu Ile
        35                  40                  45 tat ggt gca acc aac ttg gca gat ggc atg cct tcg agg ttc agt ggc     192
Tyr Gly Ala Thr Asn Leu Ala Asp Gly Met Pro Ser Arg Phe Ser Gly
    50                  55                  60 agt gga tct ggt aga gac ttc acc ctc acc atc agc agc ctg cag cct     240
Ser Gly Ser Gly Arg Asp Phe Thr Leu Thr Ile Ser Ser Leu Gln Pro
65                  70                  75                  80 gag gat ttc gca acg tat ttc tgt caa aat gtg tta agt atc cct tac     288
Glu Asp Phe Ala Thr Tyr Phe Cys Gln Asn Val Leu Ser Ile Pro Tyr
                85                  90                  95 act ttt ggc cag ggg acc aag ctg gag atc aaa                         321
Thr Phe Gly Gln Gly Thr Lys Leu Glu Ile Lys
                100                 105
```

<210> SEQ ID NO 37
<211> LENGTH: 360

<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 37

```
gag gtt cag ctg gtg cag tct ggg gca gag ctt aag aag cct ggg gcc      48
Glu Val Gln Leu Val Gln Ser Gly Ala Glu Leu Lys Lys Pro Gly Ala
1               5                   10                  15 tca gtc aag ttg tcc tgc aca gct tct ggc ttc aac att aaa gac tac      96
Ser Val Lys Leu Ser Cys Thr Ala Ser Gly Phe Asn Ile Lys Asp Tyr
            20                  25                  30 tat atg cac tgg gtg aag cag gcc cct ggc cag ggc ctg gag tgg att     144
Tyr Met His Trp Val Lys Gln Ala Pro Gly Gln Gly Leu Glu Trp Ile
        35                  40                  45 gga tgg att gat cct ggg aat ggt gat act gaa tgt gcc ccg aag ttc     192
Gly Trp Ile Asp Pro Gly Asn Gly Asp Thr Glu Cys Ala Pro Lys Phe
    50                  55                  60 cag ggc agg gcc act ttg act gca gac aca tcc atc aac aca gcc tac     240
Gln Gly Arg Ala Thr Leu Thr Ala Asp Thr Ser Ile Asn Thr Ala Tyr
65                  70                  75                  80 ctg gag ctc agc agg ctg agg tct gac gac act gcc gtc tat tac tgt     288
Leu Glu Leu Ser Arg Leu Arg Ser Asp Asp Thr Ala Val Tyr Tyr Cys
                85                  90                  95 aat gct cct tat tac tcc ggt agt agc cac ttt gac tac tgg ggc caa     336
Asn Ala Pro Tyr Tyr Ser Gly Ser Ser His Phe Asp Tyr Trp Gly Gln
            100                 105                 110 ggc acc act gtg aca gtc tcc tca                                     360
Gly Thr Thr Val Thr Val Ser Ser
        115                 120
```

<210> SEQ ID NO 38
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 38

```
gag gtt cag ctg gtg cag tct ggg gca gag gtg aag aag cct ggg gcc      48
Glu Val Gln Leu Val Gln Ser Gly Ala Glu Val Lys Lys Pro Gly Ala
1               5                   10                  15 tca gtc aag ttg tcc tgc aca gct tct ggc ttc aac att aaa gac tac      96
Ser Val Lys Leu Ser Cys Thr Ala Ser Gly Phe Asn Ile Lys Asp Tyr
            20                  25                  30 tat atg cac tgg gtg aag cag gcc cct ggc cag ggc ctg gag tgg att     144
Tyr Met His Trp Val Lys Gln Ala Pro Gly Gln Gly Leu Glu Trp Ile
        35                  40                  45 gga tgg att gat cct ggg aat ggt gat act gaa tgt gcc ccg aag ttc     192
Gly Trp Ile Asp Pro Gly Asn Gly Asp Thr Glu Cys Ala Pro Lys Phe
    50                  55                  60 cag ggc agg gcc act ttg act gca gac aca tcc atc aac aca gcc tac     240
Gln Gly Arg Ala Thr Leu Thr Ala Asp Thr Ser Ile Asn Thr Ala Tyr
65                  70                  75                  80 ctg gag ctc agc agg ctg agg tct gac gac act gcc gtc tat tac tgt     288
Leu Glu Leu Ser Arg Leu Arg Ser Asp Asp Thr Ala Val Tyr Tyr Cys
```

```
aat gct cct tat tac tcc ggt agt agc cac ttt gac tac tgg ggc caa     336
Asn Ala Pro Tyr Tyr Ser Gly Ser Ser His Phe Asp Tyr Trp Gly Gln
            100                 105                 110 ggc acc act gtg aca gtc tcc tca                                     360
Gly Thr Thr Val Thr Val Ser Ser
        115                 120

<210> SEQ ID NO 39
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 39 gag gtt cag ctg gtg cag tct ggg gca gag gtg aag aag cct ggg gcc     48
Glu Val Gln Leu Val Gln Ser Gly Ala Glu Val Lys Lys Pro Gly Ala
1               5                   10                  15 tca gtc aag ttg tcc tgc aca gct tct ggc ttc aac att aaa gac tac     96
Ser Val Lys Leu Ser Cys Thr Ala Ser Gly Phe Asn Ile Lys Asp Tyr
            20                  25                  30 tat atg cac tgg gtg agg cag gcc cct ggc cag ggc ctg gag tgg att     144
Tyr Met His Trp Val Arg Gln Ala Pro Gly Gln Gly Leu Glu Trp Ile
        35                  40                  45 gga tgg att gat cct ggg aat ggt gat act gaa tgt gcc ccg aag ttc     192
Gly Trp Ile Asp Pro Gly Asn Gly Asp Thr Glu Cys Ala Pro Lys Phe
    50                  55                  60 cag ggc agg gcc act ttg act gca gac aca tcc atc aac aca gcc tac     240
Gln Gly Arg Ala Thr Leu Thr Ala Asp Thr Ser Ile Asn Thr Ala Tyr
65                  70                  75                  80 ctg gag ctc agc agg ctg agg tct gac gac act gcc gtc tat tac tgt     288
Leu Glu Leu Ser Arg Leu Arg Ser Asp Asp Thr Ala Val Tyr Tyr Cys
                85                  90                  95 aat gct cct tat tac tcc ggt agt agc cac ttt gac tac tgg ggc caa     336
Asn Ala Pro Tyr Tyr Ser Gly Ser Ser His Phe Asp Tyr Trp Gly Gln
            100                 105                 110 ggc acc act gtg aca gtc tcc tca                                     360
Gly Thr Thr Val Thr Val Ser Ser
        115                 120

<210> SEQ ID NO 40
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 40 gag gtt cag ctg gtg cag tct ggg gca gag gtg aag aag cct ggg gcc     48
Glu Val Gln Leu Val Gln Ser Gly Ala Glu Val Lys Lys Pro Gly Ala
1               5                   10                  15 tca gtc aag ttg tcc tgc aca gct tct ggc ttc aac att aaa gac tac     96
Ser Val Lys Leu Ser Cys Thr Ala Ser Gly Phe Asn Ile Lys Asp Tyr
            20                  25                  30 tat atg cac tgg gtg agg cag gcc cct ggc cag ggc ctg gag tgg att     144
```

```
                Tyr Met His Trp Val Arg Gln Ala Pro Gly Gln Gly Leu Glu Trp Ile
                         35                  40                  45 gga tgg att gat cct ggg aat ggt gat act gaa tgt gcc ccg aag ttc        192
Gly Trp Ile Asp Pro Gly Asn Gly Asp Thr Glu Cys Ala Pro Lys Phe
 50                  55                  60 cag ggc agg gcc act ttg act gca gac aca tcc atc agc aca gcc tac        240
Gln Gly Arg Ala Thr Leu Thr Ala Asp Thr Ser Ile Ser Thr Ala Tyr
 65                  70                  75                  80 ctg gag ctc agc agg ctg agg tct gac gac act gcc gtc tat tac tgt        288
Leu Glu Leu Ser Arg Leu Arg Ser Asp Asp Thr Ala Val Tyr Tyr Cys
                 85                  90                  95 aat gct cct tat tac tcc ggt agt agc cac ttt gac tac tgg ggc caa        336
Asn Ala Pro Tyr Tyr Ser Gly Ser Ser His Phe Asp Tyr Trp Gly Gln
                100                 105                 110 ggc acc act gtg aca gtc tcc tca                                        360
Gly Thr Thr Val Thr Val Ser Ser
                115                 120

<210> SEQ ID NO 41
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 41 gag gtt cag ctg gtg cag tct ggg gca gag gtg aag aag cct ggg gcc         48
Glu Val Gln Leu Val Gln Ser Gly Ala Glu Val Lys Lys Pro Gly Ala
 1               5                  10                  15 tca gtc aag gtg tcc tgc aca gct tct ggc ttc aac att aaa gac tac         96
Ser Val Lys Val Ser Cys Thr Ala Ser Gly Phe Asn Ile Lys Asp Tyr
                 20                  25                  30 tat atg cac tgg gtg agg cag gcc cct ggc cag ggc ctg gag tgg att        144
Tyr Met His Trp Val Arg Gln Ala Pro Gly Gln Gly Leu Glu Trp Ile
                 35                  40                  45 gga tgg att gat cct ggg aat ggt gat act gaa tgt gcc ccg aag ttc        192
Gly Trp Ile Asp Pro Gly Asn Gly Asp Thr Glu Cys Ala Pro Lys Phe
 50                  55                  60 cag ggc agg gcc act atc act gca gac aca tcc atc agc aca gcc tac        240
Gln Gly Arg Ala Thr Ile Thr Ala Asp Thr Ser Ile Ser Thr Ala Tyr
 65                  70                  75                  80 atg gag ctc agc agg ctg agg tct gac gac act gcc gtc tat tac tgt        288
Met Glu Leu Ser Arg Leu Arg Ser Asp Asp Thr Ala Val Tyr Tyr Cys
                 85                  90                  95 aat gct cct tat tac tcc ggt agt agc cac ttt gac tac tgg ggc caa        336
Asn Ala Pro Tyr Tyr Ser Gly Ser Ser His Phe Asp Tyr Trp Gly Gln
                100                 105                 110 ggc acc act gtg aca gtc tcc tca                                        360
Gly Thr Thr Val Thr Val Ser Ser
                115                 120

<210> SEQ ID NO 42
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
```

<222> LOCATION: (1)..(330)

<400> SEQUENCE: 42

```
gac att gtg ctg aca cag tct cct gac tcc tta gct gta tct ctg ggg      48
Asp Ile Val Leu Thr Gln Ser Pro Asp Ser Leu Ala Val Ser Leu Gly
1               5                   10                  15 gag agg gcc acc atc aac tgc agg gcc agc aaa agt gtc agt gca tct      96
Glu Arg Ala Thr Ile Asn Cys Arg Ala Ser Lys Ser Val Ser Ala Ser
            20                  25                  30 ggc tat agt ttt ttg cac tgg tac caa cag aaa cca gga cag cca ccc     144
Gly Tyr Ser Phe Leu His Trp Tyr Gln Gln Lys Pro Gly Gln Pro Pro
        35                  40                  45 aaa ctc ctc atc tat ctt gca tcc aac ctg gag tct ggg gtc cct gac     192
Lys Leu Leu Ile Tyr Leu Ala Ser Asn Leu Glu Ser Gly Val Pro Asp
    50                  55                  60 agg ttc agt ggc agt ggg tct ggg aca gac ttc acc ctc acc atc agc     240
Arg Phe Ser Gly Ser Gly Ser Gly Thr Asp Phe Thr Leu Thr Ile Ser
65                  70                  75                  80 agc ctg cag gag gag gat gtg gca acc tat tac tgt cag cac agt agg     288
Ser Leu Gln Glu Glu Asp Val Ala Thr Tyr Tyr Cys Gln His Ser Arg
                85                  90                  95 gag ctt cgg acg ttc ggt cag ggc acc aag ctg gaa atc aaa             330
Glu Leu Arg Thr Phe Gly Gln Gly Thr Lys Leu Glu Ile Lys
            100                 105                 110
```

<210> SEQ ID NO 43
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(330)

<400> SEQUENCE: 43

```
gac att gtg ctg aca cag tct cct gac tcc tta gct gta tct ctg ggg      48
Asp Ile Val Leu Thr Gln Ser Pro Asp Ser Leu Ala Val Ser Leu Gly
1               5                   10                  15 gag agg gcc acc atc aac tgc agg gcc agc aaa agt gtc agt gca tct      96
Glu Arg Ala Thr Ile Asn Cys Arg Ala Ser Lys Ser Val Ser Ala Ser
            20                  25                  30 ggc tat agt ttt ttg cac tgg tac caa cag aaa cca gga cag cca ccc     144
Gly Tyr Ser Phe Leu His Trp Tyr Gln Gln Lys Pro Gly Gln Pro Pro
        35                  40                  45 aaa ctc ctc atc tat ctt gca tcc aac ctg gag tct ggg gtc cct gac     192
Lys Leu Leu Ile Tyr Leu Ala Ser Asn Leu Glu Ser Gly Val Pro Asp
    50                  55                  60 agg ttc agt ggc agt ggg tct ggg aca gac ttc acc ctc acc atc agc     240
Arg Phe Ser Gly Ser Gly Ser Gly Thr Asp Phe Thr Leu Thr Ile Ser
65                  70                  75                  80 agc ctg cag gcc gag gat gtg gca acc tat tac tgt cag cac agt agg     288
Ser Leu Gln Ala Glu Asp Val Ala Thr Tyr Tyr Cys Gln His Ser Arg
                85                  90                  95 gag ctt cgg acg ttc ggt cag ggc acc aag ctg gaa atc aaa             330
Glu Leu Arg Thr Phe Gly Gln Gly Thr Lys Leu Glu Ile Lys
            100                 105                 110
```

<210> SEQ ID NO 44
<211> LENGTH: 330
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(330)

<400> SEQUENCE: 44 gac att gtg atg aca cag tct cct gac tcc tta gct gta tct ctg ggg    48
Asp Ile Val Met Thr Gln Ser Pro Asp Ser Leu Ala Val Ser Leu Gly
1               5                  10                  15 gag agg gcc acc atc aac tgc agg gcc agc aaa agt gtc agt gca tct    96
Glu Arg Ala Thr Ile Asn Cys Arg Ala Ser Lys Ser Val Ser Ala Ser
            20                  25                  30 ggc tat agt ttt ttg cac tgg tac caa cag aaa cca gga cag cca ccc   144
Gly Tyr Ser Phe Leu His Trp Tyr Gln Gln Lys Pro Gly Gln Pro Pro
        35                  40                  45 aaa ctc ctc atc tat ctt gca tcc aac ctg gag tct ggg gtc cct gac   192
Lys Leu Leu Ile Tyr Leu Ala Ser Asn Leu Glu Ser Gly Val Pro Asp
    50                  55                  60 agg ttc agt ggc agt ggg tct ggg aca gac ttc acc ctc acc atc agc   240
Arg Phe Ser Gly Ser Gly Ser Gly Thr Asp Phe Thr Leu Thr Ile Ser
65                  70                  75                  80 agc ctg cag gcc gag gat gtg gca gtg tat tac tgt cag cac agt agg   288
Ser Leu Gln Ala Glu Asp Val Ala Val Tyr Tyr Cys Gln His Ser Arg
                85                  90                  95 gag ctt cgg acg ttc ggt cag ggc acc aag ctg gaa atc aaa           330
Glu Leu Arg Thr Phe Gly Gln Gly Thr Lys Leu Glu Ile Lys
            100                 105                 110

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 45

His His His His His His
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Gly Gly Ser
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Glu Trp Ile Gly
1               5
```

```
<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Tyr Cys Ala Arg
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Tyr Cys Asn Ala
1               5

<210> SEQ ID NO 50
<211> LENGTH: 344
<212> TYPE: PRT
<213> ORGANISM: Homo sapiens

<400> SEQUENCE: 50

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Ser Val Lys Arg Asn
            195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
```

```
                225                 230                 235                 240
Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
                260                 265                 270

Ile Asn Gly Thr Phe Gln Gln Ser Thr Gln Glu Leu Phe Ile Pro Asn
                275                 280                 285

Ile Thr Val Asn Asn Ser Gly Ser Tyr Met Cys Gln Ala His Asn Ser
                290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
                340

<210> SEQ ID NO 51
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Leu Val Asn Glu Glu Ala Thr Gly Gln Phe His Val Tyr Pro Glu Leu
1               5                   10                  15

Pro Lys Pro Ser Ile Ser Ser Asn Asn Ser Asn Pro Val Glu Asp Lys
                20                  25                  30

Asp Ala Val Ala Phe Thr Cys Glu Pro Glu Val Gln Asn Thr Thr Tyr
            35                  40                  45

Leu Trp Trp Val Asn Gly Gln Ser Leu Pro Val Ser Pro Arg Leu Gln
        50                  55                  60

Leu Ser Asn Gly Asn Met Thr Leu Thr Leu Leu Ser Val Lys Arg Asn
65                  70                  75                  80

Asp Ala Gly Ser Tyr Glu Cys Glu Ile Gln Asn Pro Ala Ser Ala Asn
                85                  90                  95

Arg Ser Asp Pro Val Thr Leu Asn Val Leu Tyr Gly Pro Asp Gly Pro
                100                 105                 110

Thr Ile Ser Pro Ser Lys Ala Asn Tyr Arg Pro Gly Glu Asn Leu Asn
                115                 120                 125

Leu Ser Cys His Ala Ala Ser Asn Pro Pro Ala Gln Tyr Ser Trp Phe
                130                 135                 140

Ile Asn Gly Thr Phe Gln Gln Ser Thr Gln Glu Leu Phe Ile Pro Asn
145                 150                 155                 160

Ile Thr Val Asn Asn Ser Gly Ser Tyr Met Cys Gln Ala His Asn Ser
                165                 170                 175

Ala Thr Gly Leu Asn Arg Thr Thr Val Thr Met Ile Thr Val
                180                 185                 190

<210> SEQ ID NO 52
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 52

Leu Val Asn Glu Glu Ala Thr Gly Gln Phe His Val Tyr Pro Glu Leu
1               5                   10                  15

Pro Lys Pro Ser Ile Ser Ser Asn Asn Ser Asn Pro Val Glu Asp Lys
                20                  25                  30

Asp Ala Val Ala Phe Thr Cys Glu Pro Glu Val Gln Asn Thr Thr Tyr
                35                  40                  45

Leu Trp Trp Val Asn Gly Gln Ser Leu Pro Val Ser Pro Arg Leu Gln
        50                  55                  60

<210> SEQ ID NO 53
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Leu Ser Asn Gly Asn Met Thr Leu Thr Leu Leu Ser Val Lys Arg Asn
1               5                   10                  15

Asp Ala Gly Ser Tyr Glu Cys Glu Ile Gln Pro Ala Ser Ala Asn
                20                  25                  30

Arg Ser Asp Pro Val Thr Leu Asn Val Leu Tyr Gly Pro Asp Gly Pro
                35                  40                  45

Thr Ile Ser Pro Ser Lys Ala Asn Tyr Arg Pro Gly Glu Asn Leu
        50                  55                  60

<210> SEQ ID NO 54
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asn Leu Ser Cys His Ala Ala Ser Asn Pro Pro Ala Gln Tyr Ser Trp
1               5                   10                  15

Phe Ile Asn Gly Thr Phe Gln Gln Ser Thr Gln Glu Leu Phe Ile Pro
                20                  25                  30

Asn Ile Thr Val Asn Asn Ser Gly Ser Tyr Met Cys Gln Ala His Asn
                35                  40                  45

Ser Ala Thr Gly Leu Asn Arg Thr Thr Val Thr Met Ile Thr Val
        50                  55                  60

<210> SEQ ID NO 55
<211> LENGTH: 128
<212> TYPE: PRT
<213> ORGANISM: Homo sapiens

<400> SEQUENCE: 55

Leu Gln Leu Ser Asn Gly Asn Arg Thr Leu Thr Leu Phe Asn Val Thr
1               5                   10                  15

Arg Asn Asp Ser Ala Ser Tyr Lys Cys Glu Thr Gln Asn Pro Val Ser
                20                  25                  30

Ala Arg Arg Ser Asp Ser Val Ile Leu Asn Val Leu Tyr Gly Pro Asp
                35                  40                  45

Ala Pro Thr Ile Ser Pro Leu Asn Thr Ser Tyr Arg Ser Gly Glu Asn
        50                  55                  60
```

Leu Asn Leu Ser Cys His Ala Ala Ser Asn Pro Pro Ala Gln Tyr Ser
 65                  70                  75                  80

Trp Phe Val Asn Gly Thr Phe Gln Gln Ser Thr Gln Glu Leu Phe Ile
                 85                  90                  95

Pro Asn Ile Thr Val Asn Asn Ser Gly Ser Tyr Thr Cys Gln Ala His
            100                 105                 110

Asn Ser Asp Thr Gly Leu Asn Arg Thr Thr Val Thr Thr Ile Thr Val
        115                 120                 125

<210> SEQ ID NO 56
<211> LENGTH: 128
<212> TYPE: PRT
<213> ORGANISM: Homo sapiens

<400> SEQUENCE: 56

Leu Gln Leu Ser Asn Gly Asn Met Thr Leu Thr Leu Ser Val Lys
 1               5                  10                  15

Arg Asn Asp Ala Gly Ser Tyr Glu Cys Glu Ile Gln Asn Pro Ala Ser
                 20                  25                  30

Ala Asn Arg Ser Asp Pro Val Thr Leu Asn Val Leu Tyr Gly Pro Asp
             35                  40                  45

Gly Pro Thr Ile Ser Pro Ser Lys Ala Asn Tyr Arg Pro Gly Glu Asn
 50                  55                  60

Leu Asn Leu Ser Cys His Ala Ala Ser Asn Pro Pro Ala Gln Tyr Ser
 65                  70                  75                  80

Trp Phe Ile Asn Gly Thr Phe Gln Gln Ser Thr Gln Glu Leu Phe Ile
                 85                  90                  95

Pro Asn Ile Thr Val Asn Asn Ser Gly Ser Tyr Met Cys Gln Ala His
            100                 105                 110

Asn Ser Ala Thr Gly Leu Asn Arg Thr Thr Val Thr Met Ile Thr Val
        115                 120                 125

<210> SEQ ID NO 57
<211> LENGTH: 128
<212> TYPE: PRT
<213> ORGANISM: Homo sapiens

<400> SEQUENCE: 57

Leu Gln Leu Ser Asn Gly Asn Arg Thr Leu Thr Leu Ser Val Thr
 1               5                  10                  15

Arg Asn Asp Val Gly Pro Tyr Glu Cys Glu Ile Gln Asn Pro Ala Ser
                 20                  25                  30

Ala Asn Phe Ser Asp Pro Val Thr Leu Asn Val Leu Tyr Gly Pro Asp
             35                  40                  45

Ala Pro Thr Ile Ser Pro Ser Asp Thr Tyr Tyr His Ala Gly Val Asn
 50                  55                  60

Leu Asn Leu Ser Cys His Ala Ala Ser Asn Pro Pro Ser Gln Tyr Ser
 65                  70                  75                  80

Trp Ser Val Asn Gly Thr Phe Gln Gln Tyr Thr Gln Lys Leu Phe Ile
                 85                  90                  95

Pro Asn Ile Thr Thr Lys Asn Ser Gly Ser Tyr Ala Cys His Thr Thr
            100                 105                 110

Asn Ser Ala Thr Gly Arg Asn Arg Thr Thr Val Arg Met Ile Thr Val
        115                 120                 125

<210> SEQ ID NO 58

```
<211> LENGTH: 4
<212> TYPE: PRT
<213> ORGANISM: Homo sapiens

<400> SEQUENCE: 58

Asn Ser Ala Thr
1

<210> SEQ ID NO 59
<211> LENGTH: 4
<212> TYPE: PRT
<213> ORGANISM: Homo sapiens

<400> SEQUENCE: 59

Asn Ser Ala Ala
1

<210> SEQ ID NO 60
<211> LENGTH: 4
<212> TYPE: PRT
<213> ORGANISM: Homo sapiens

<400> SEQUENCE: 60

Leu Asn Arg Thr
1

<210> SEQ ID NO 61
<211> LENGTH: 4
<212> TYPE: PRT
<213> ORGANISM: Homo sapiens

<400> SEQUENCE: 61

Arg Asn Arg Thr
1

<210> SEQ ID NO 62
<211> LENGTH: 4
<212> TYPE: PRT
<213> ORGANISM: Homo sapiens

<400> SEQUENCE: 62

Met Ile Thr Val
1

<210> SEQ ID NO 63
<211> LENGTH: 4
<212> TYPE: PRT
<213> ORGANISM: Homo sapiens

<400> SEQUENCE: 63

Ala Ile Thr Val
1

<210> SEQ ID NO 64
<211> LENGTH: 4
<212> TYPE: PRT
<213> ORGANISM: Homo sapiens

<400> SEQUENCE: 64

Met Ala Thr Val
1

<210> SEQ ID NO 65
<211> LENGTH: 4
<212> TYPE: PRT
```

<213> ORGANISM: Homo sapiens

<400> SEQUENCE: 65

Met Ile Ala Val
1

<210> SEQ ID NO 66
<211> LENGTH: 4
<212> TYPE: PRT
<213> ORGANISM: Homo sapiens

<400> SEQUENCE: 66

Met Ile Thr Ala
1

<210> SEQ ID NO 67
<211> LENGTH: 4
<212> TYPE: PRT
<213> ORGANISM: Homo sapiens

<400> SEQUENCE: 67

Ala Ala Ala Ala
1

<210> SEQ ID NO 68
<211> LENGTH: 4
<212> TYPE: PRT
<213> ORGANISM: Homo sapiens

<400> SEQUENCE: 68

Ala Ala Ala Val
1

<210> SEQ ID NO 69
<211> LENGTH: 4
<212> TYPE: PRT
<213> ORGANISM: Homo sapiens

<400> SEQUENCE: 69

Ala Ala Thr Val
1

<210> SEQ ID NO 70
<211> LENGTH: 4
<212> TYPE: PRT
<213> ORGANISM: Homo sapiens

<400> SEQUENCE: 70

Cys Gln Ala His
1

<210> SEQ ID NO 71
<211> LENGTH: 4
<212> TYPE: PRT
<213> ORGANISM: Homo sapiens

<400> SEQUENCE: 71

Ala Gln Ala His
1

<210> SEQ ID NO 72
<211> LENGTH: 5
<212> TYPE: PRT
<213> ORGANISM: Homo sapiens

```
<400> SEQUENCE: 72

Met Cys Gln Ala His
1               5

<210> SEQ ID NO 73
<211> LENGTH: 5
<212> TYPE: PRT
<213> ORGANISM: Homo sapiens

<400> SEQUENCE: 73

Ala Cys Gln Ala His
1               5

<210> SEQ ID NO 74
<211> LENGTH: 6
<212> TYPE: PRT
<213> ORGANISM: Homo sapiens

<400> SEQUENCE: 74

Tyr Met Cys Gln Ala His
1               5

<210> SEQ ID NO 75
<211> LENGTH: 6
<212> TYPE: PRT
<213> ORGANISM: Homo sapiens

<400> SEQUENCE: 75

Ala Met Cys Gln Ala His
1               5

<210> SEQ ID NO 76
<211> LENGTH: 5
<212> TYPE: PRT
<213> ORGANISM: Homo sapiens

<400> SEQUENCE: 76

Ala Ala Gln Ala His
1               5

<210> SEQ ID NO 77
<211> LENGTH: 19
<212> TYPE: PRT
<213> ORGANISM: Homo sapiens

<400> SEQUENCE: 77

Gln Ala His Asn Ser Ala Thr Gly Leu Asn Arg Thr Thr Val Thr Met
1               5                   10                  15

Ile Thr Val

<210> SEQ ID NO 78
<211> LENGTH: 19
<212> TYPE: PRT
<213> ORGANISM: Homo sapiens

<400> SEQUENCE: 78

Gln Ala His Asn Ser Ala Thr Gly Leu Gln Arg Thr Thr Val Thr Met
1               5                   10                  15

Ile Thr Val

<210> SEQ ID NO 79
<211> LENGTH: 19
<212> TYPE: PRT
```

<213> ORGANISM: Homo sapiens

<400> SEQUENCE: 79

Gln Ala His Asn Ser Ala Thr Gly Leu Ala Arg Thr Thr Val Thr Met
1               5                   10                  15

Ile Thr Val

<210> SEQ ID NO 80
<211> LENGTH: 19
<212> TYPE: PRT
<213> ORGANISM: Homo sapiens

<400> SEQUENCE: 80

His Ala His Asn Ser Ala Thr Gly Leu Asn Arg Thr Thr Val Thr Met
1               5                   10                  15

Ile Thr Val

<210> SEQ ID NO 81
<211> LENGTH: 19
<212> TYPE: PRT
<213> ORGANISM: Homo sapiens

<400> SEQUENCE: 81

Gln Ala Thr Asn Ser Ala Thr Gly Leu Asn Arg Thr Thr Val Thr Met
1               5                   10                  15

Ile Thr Val

<210> SEQ ID NO 82
<211> LENGTH: 19
<212> TYPE: PRT
<213> ORGANISM: Homo sapiens

<400> SEQUENCE: 82

Gln Ala His Gln Ser Ala Thr Gly Leu Asn Arg Thr Thr Val Thr Met
1               5                   10                  15

Ile Thr Val

<210> SEQ ID NO 83
<211> LENGTH: 19
<212> TYPE: PRT
<213> ORGANISM: Homo sapiens

<400> SEQUENCE: 83

Gln Ala His Asn Ala Ala Thr Gly Leu Asn Arg Thr Thr Val Thr Met
1               5                   10                  15

Ile Thr Val

<210> SEQ ID NO 84
<211> LENGTH: 19
<212> TYPE: PRT
<213> ORGANISM: Homo sapiens

<400> SEQUENCE: 84

Gln Ala His Asn Ser Ala Ala Gly Leu Asn Arg Thr Thr Val Thr Met
1               5                   10                  15

Ile Thr Val

<210> SEQ ID NO 85
<211> LENGTH: 19
<212> TYPE: PRT

<400> SEQUENCE: 85

Gln Ala His Asn Ser Ala Thr Gly Arg Asn Arg Thr Thr Val Thr Met
1               5                   10                  15

Ile Thr Val

<210> SEQ ID NO 86
<211> LENGTH: 19
<212> TYPE: PRT
<213> ORGANISM: Homo sapiens

<400> SEQUENCE: 86

Gln Ala His Asn Ser Ala Thr Gly Leu Asn Ala Thr Thr Val Thr Met
1               5                   10                  15

Ile Thr Val

<210> SEQ ID NO 87
<211> LENGTH: 19
<212> TYPE: PRT
<213> ORGANISM: Homo sapiens

<400> SEQUENCE: 87

Gln Ala His Asn Ser Ala Thr Gly Leu Asn Arg Ser Thr Val Thr Met
1               5                   10                  15

Ile Thr Val

<210> SEQ ID NO 88
<211> LENGTH: 19
<212> TYPE: PRT
<213> ORGANISM: Homo sapiens

<400> SEQUENCE: 88

Gln Ala His Asn Ser Ala Thr Gly Leu Asn Arg Ala Thr Val Thr Met
1               5                   10                  15

Ile Thr Val

<210> SEQ ID NO 89
<211> LENGTH: 19
<212> TYPE: PRT
<213> ORGANISM: Homo sapiens

<400> SEQUENCE: 89

Gln Ala His Asn Ser Ala Thr Gly Leu Asn Arg Thr Thr Val Ala Met
1               5                   10                  15

Ile Thr Val

<210> SEQ ID NO 90
<211> LENGTH: 19
<212> TYPE: PRT
<213> ORGANISM: Homo sapiens

<400> SEQUENCE: 90

Gln Ala His Asn Ser Ala Thr Gly Leu Asn Arg Thr Ala Ala Ala Met
1               5                   10                  15

Ile Thr Val

<210> SEQ ID NO 91
<211> LENGTH: 19
<212> TYPE: PRT
<213> ORGANISM: Homo sapiens

```
<400> SEQUENCE: 91

Gln Ala His Asn Ser Ala Thr Gly Leu Asn Arg Thr Thr Val Thr Ala
1               5                   10                  15

Ile Thr Val

<210> SEQ ID NO 92
<211> LENGTH: 19
<212> TYPE: PRT
<213> ORGANISM: Homo sapiens

<400> SEQUENCE: 92

Gln Ala His Asn Ser Ala Thr Gly Leu Asn Arg Thr Thr Val Thr Met
1               5                   10                  15

Ala Thr Val

<210> SEQ ID NO 93
<211> LENGTH: 19
<212> TYPE: PRT
<213> ORGANISM: Homo sapiens

<400> SEQUENCE: 93

Gln Ala His Asn Ser Ala Thr Gly Leu Asn Arg Thr Thr Val Thr Met
1               5                   10                  15

Ile Ala Val

<210> SEQ ID NO 94
<211> LENGTH: 19
<212> TYPE: PRT
<213> ORGANISM: Homo sapiens

<400> SEQUENCE: 94

Gln Ala His Asn Ser Ala Thr Gly Leu Asn Arg Thr Thr Val Thr Met
1               5                   10                  15

Ile Thr Ala

<210> SEQ ID NO 95
<211> LENGTH: 19
<212> TYPE: PRT
<213> ORGANISM: Homo sapiens

<400> SEQUENCE: 95

His Thr Thr Asn Ser Ala Thr Gly Leu Asn Arg Thr Thr Val Thr Met
1               5                   10                  15

Ile Thr Val

<210> SEQ ID NO 96
<211> LENGTH: 20
<212> TYPE: PRT
<213> ORGANISM: Homo sapiens

<400> SEQUENCE: 96

Cys Gln Ala His Asn Ser Ala Thr Gly Leu Asn Arg Thr Thr Val Thr
1               5                   10                  15

Met Ile Thr Val
            20

<210> SEQ ID NO 97
<211> LENGTH: 20
<212> TYPE: PRT
<213> ORGANISM: Homo sapiens
```

```
<400> SEQUENCE: 97

Ala Gln Ala His Asn Ser Ala Thr Gly Leu Asn Arg Thr Thr Val Thr
1               5                   10                  15

Met Ile Thr Val
            20

<210> SEQ ID NO 98
<211> LENGTH: 21
<212> TYPE: PRT
<213> ORGANISM: Homo sapiens

<400> SEQUENCE: 98

Met Cys Gln Ala His Asn Ser Ala Thr Gly Leu Asn Arg Thr Thr Val
1               5                   10                  15

Thr Met Ile Thr Val
            20

<210> SEQ ID NO 99
<211> LENGTH: 21
<212> TYPE: PRT
<213> ORGANISM: Homo sapiens

<400> SEQUENCE: 99

Ala Cys Gln Ala His Asn Ser Ala Thr Gly Leu Asn Arg Thr Thr Val
1               5                   10                  15

Thr Met Ile Thr Val
            20

<210> SEQ ID NO 100
<211> LENGTH: 22
<212> TYPE: PRT
<213> ORGANISM: Homo sapiens

<400> SEQUENCE: 100

Ala Met Cys Gln Ala His Asn Ser Ala Thr Gly Leu Asn Arg Thr Thr
1               5                   10                  15

Val Thr Met Ile Thr Val
            20

<210> SEQ ID NO 101
<211> LENGTH: 22
<212> TYPE: PRT
<213> ORGANISM: Homo sapiens

<400> SEQUENCE: 101

Tyr Met Cys Gln Ala His Asn Ser Ala Thr Gly Leu Asn Arg Thr Thr
1               5                   10                  15

Val Thr Met Ile Thr Val
            20

<210> SEQ ID NO 102
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Ala His Asn Ser Ala Thr Gly Leu Asn Arg Thr Thr Val Thr Met
1               5                   10                  15

Ile Thr Val Ser Gly Ser Ala Pro Val Leu Arg
```

```
                    20                  25

<210> SEQ ID NO 103
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Pro Thr Ile Ser Pro Ser Lys Ala Asn Tyr Arg Pro Gly Glu Asn
1               5                   10                  15

Leu Asn Leu Ser Cys His Ala Ala Ser Asn Pro Pro Ala Gln Tyr Ser
            20                  25                  30

Trp Phe Ile Asn Gly Thr Phe Gln Gln Ser Thr Gln Glu Leu Phe Ile
        35                  40                  45

Pro Asn Ile Thr Val Asn Asn Ser Gly Ser Tyr Met Cys Gln Ala His
    50                  55                  60

Asn Ser Ala Thr Gly Leu Asn Arg Thr Thr Val Thr Met Ile Thr Val
65                  70                  75                  80

<210> SEQ ID NO 104
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gly Pro Thr Ile Ser Pro Ser Lys Ala Asn Tyr Arg Pro Gly Glu Asn
1               5                   10                  15

Leu Asn Leu Ser Ala His Ala Ala Ser Asn Pro Pro Ala Gln Tyr Ser
            20                  25                  30

Trp Phe Ile Asn Gly Thr Phe Gln Gln Ser Thr Gln Glu Leu Phe Ile
        35                  40                  45

Pro Asn Ile Thr Val Asn Asn Ser Gly Ser Tyr Met Cys Gln Ala His
    50                  55                  60

Asn Ser Ala Thr Gly Leu Asn Arg Thr Thr Val Thr Met Ile Thr Val
65                  70                  75                  80

<210> SEQ ID NO 105
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gly Thr Phe Gln Gln Ser Thr Gln Glu Leu Phe Ile Pro Asn Ile Thr
1               5                   10                  15

Val Asn Asn Ser Gly Ser Tyr Met Cys Gln Ala His Asn Ser Ala Thr
            20                  25                  30

Gly Leu Asn Arg Thr Thr Val Thr Met Ile Thr Val
        35                  40

<210> SEQ ID NO 106
<211> LENGTH: 25
<212> TYPE: DNA
<213> ORGANISM: Artificial Sequence
```

```
<220> FEATURE:
<223> OTHER INFORMATION: Ig1F primer

<400> SEQUENCE: 106
gaattcaaag ccctccatct ccagc                                    25

<210> SEQ ID NO 107
<211> LENGTH: 24
<212> TYPE: DNA
<213> ORGANISM: Artificial Sequence
<220> FEATURE:
<223> OTHER INFORMATION: Ig1R primer

<400> SEQUENCE: 107
agatctattc agggtgactg ggtc                                     24

<210> SEQ ID NO 108
<211> LENGTH: 25
<212> TYPE: DNA
<213> ORGANISM: Artificial Sequence
<220> FEATURE:
<223> OTHER INFORMATION: Ig2F primer

<400> SEQUENCE: 108
gaattcagat ggccccacca tttgg                                    25

<210> SEQ ID NO 109
<211> LENGTH: 24
<212> TYPE: DNA
<213> ORGANISM: Artificial Sequence
<220> FEATURE:
<223> OTHER INFORMATION: Ig2R primer

<400> SEQUENCE: 109
agatctggtg actgtggtcc tatt                                     24

<210> SEQ ID NO 110
<211> LENGTH: 25
<212> TYPE: DNA
<213> ORGANISM: Artificial Sequence
<220> FEATURE:
<223> OTHER INFORMATION: peptide3F primer

<400> SEQUENCE: 110
gaattcactg cagctgtcca atggc                                    25

<210> SEQ ID NO 111
<211> LENGTH: 24
<212> TYPE: DNA
<213> ORGANISM: Artificial Sequence
<220> FEATURE:
<223> OTHER INFORMATION: peptide3R primer

<400> SEQUENCE: 111
agatcttttg acgctgagta gagt                                     24

<210> SEQ ID NO 112
<211> LENGTH: 40
<212> TYPE: DNA
<213> ORGANISM: Artificial Sequence
<220> FEATURE:
<223> OTHER INFORMATION: C6f1 300 HTT302 forward primer

<400> SEQUENCE: 112
gcggatccta tatgtgccac accactaact cagccactgg                    40
```

```
<210> SEQ ID NO 113
<211> LENGTH: 44
<212> TYPE: DNA
<213> ORGANISM: Artificial Sequence
<220> FEATURE:
<223> OTHER INFORMATION: C6f1 300 HTT302 reverse primer

<400> SEQUENCE: 113
gaggccagtg gctgagttag tggtgtggca catataggat ccgc                    44

<210> SEQ ID NO 114
<211> LENGTH: 39
<212> TYPE: DNA
<213> ORGANISM: Artificial Sequence
<220> FEATURE:
<223> OTHER INFORMATION: C8f1 300 QAH302 forward primer

<400> SEQUENCE: 114
ggatcctatg cctgccaagc ccataactca gccactggc                          39

<210> SEQ ID NO 115
<211> LENGTH: 39
<212> TYPE: DNA
<213> ORGANISM: Artificial Sequence
<220> FEATURE:
<223> OTHER INFORMATION: C8f1 300 QAH302 reverse primer

<400> SEQUENCE: 115
gccagtggct gagttatggg cttggcaggc ataggatcc                          39
```

What is claimed:

1. An isolated antibody that binds to human CEACAM 6, comprising three heavy chain complementarity determining regions (CDRs) and three light chain CDRs, wherein the CDRs comprise:
   (i) a heavy chain CDR1 having the amino acid sequence of SEQ ID NO: 1;
   (ii) a heavy chain CDR2 having the amino acid sequence of SEQ ID NO: 2;
   (iii) a heavy chain CDR3 having the amino acid sequence of SEQ ID NO: 3;
   (iv) a light chain CDR1 having the amino acid sequence of SEQ ID NO: 4;
   (v) a light chain CDR2 having the amino acid sequence of SEQ ID NO: 5; and
   (vi) a light chain CDR3 having the amino acid sequence of SEQ ID NO: 6.

2. The isolated antibody of claim 1, wherein the antibody comprises a heavy chain variable region having the amino acid sequence of one of SEQ ID NOs:13-17, and a light chain variable region having the amino acid sequence of one of SEQ ID NOs:18-20.

3. The isolated antibody of claim 1, wherein said antibody is a monoclonal antibody, a chimeric antibody, a humanized antibody, a CDR-grafted antibody, a Fab, a Fab', a F(ab')2, a Fv, a disulfide linked Fv, a scFv, a diabody, a multispecific antibody, a bi-specific T cell engager, an anti-idiotypic antibody, or a bispecific antibody.

4. A pharmaceutical composition comprising the isolated antibody of claim 1 and a pharmaceutically acceptable carrier.

5. An isolated polynucleotide sequence encoding the isolated antibody of claim 1, or fragment thereof.

6. An expression vector comprising the polynucleotide sequence of claim 5.

7. An isolated host cell comprising the expression vector of claim 6.

8. A method of treating cancer or pancreatitis in a subject in need thereof, comprising administering to the subject a composition comprising the polynucleotide sequence of claim 5.

9. The method of claim 8, wherein the cancer is pancreatic cancer, lung cancer, non-small cell lung cancer, colon cancer, breast cancer, ovarian cancer, gastric cancer, chronic myeloid leukemia, acute B lymphoblastic leukemia, liver cancer, or prostate cancer.

10. A method of treating cancer or pancreatitis in a subject in need thereof, comprising administering to the subject the pharmaceutical composition of claim 4.

11. The method of claim 10, wherein the cancer is pancreatic cancer, lung cancer, non-small cell lung cancer, colon cancer, breast cancer, ovarian cancer, gastric cancer, chronic myeloid leukemia, acute B lymphoblastic leukemia, liver cancer, or prostate cancer.

12. A humanized anti-CEACAM 6 antibody comprising (i) a human framework (FR) having one or more constant region that is at least 85%-100% identical to a human immunoglobulin constant region, and (ii) three heavy chain complementarity determining regions (CDRs) and three light chain CDRs, wherein the CDRs comprise:
   (a) a heavy chain CDR1 having the amino acid sequence of SEQ ID NO: 1;
   (b) a heavy chain CDR2 having the amino acid sequence of SEQ ID NO: 2;
   (c) a heavy chain CDR3 having the amino acid sequence of SEQ ID NO: 3;

(d) a light chain CDR1 having the amino acid sequence of SEQ ID NO: 4;
(e) a light chain CDR2 having the amino acid sequence of SEQ ID NO: 5; and
(f) a light chain CDR3 having the amino acid sequence of SEQ ID NO: 6.

13. The humanized anti-CEACAM 6 antibody of claim 12, wherein the antibody comprises a heavy chain variable region having the amino acid sequence of one of SEQ ID NOs:13-17, and a light chain variable region having the amino acid sequence of one of SEQ ID NOs:18-20.

14. The humanized anti-CEACAM 6 antibody of claim 12, wherein the constant region is at least 95% identical to a human immunoglobulin constant region.

15. The humanized anti-CEACAM 6 antibody of claim 12, wherein the human FR comprises FR sequences encoded by human VH1-18*01 germline; and FR sequences encoded by human VK1-39*01 germline.

16. The humanized anti-CEACAM 6 antibody of claim 12, wherein the antibody binds to human or mouse CEACAM 5 and CEACAM 6.

17. The humanized anti-CEACAM 6 antibody of claim 12, wherein the antibody binds to at least one epitope comprising a glycopeptide on CEACAM 6.

18. The humanized anti-CEACAM 6 antibody of claim 17, wherein the glycopeptide epitope comprises amino acids 300-318 of human CEACAM 6.

19. A method of treating cancer or pancreatitis in a subject in need thereof, comprising administering to the subject a composition comprising the humanized anti-CEACAM 6 antibody of claim 12.

20. The method of claim 19, wherein the cancer is pancreatic cancer, lung cancer, non-small cell lung cancer, colon cancer, breast cancer, liver cancer, or prostate cancer.

* * * * *